United States Patent
Bown et al.

(10) Patent No.: US 10,004,875 B2
(45) Date of Patent: Jun. 26, 2018

(54) STYLET APPARATUSES AND METHODS OF MANUFACTURE

(71) Applicant: C. R. Bard, Inc., Murray Hill, NJ (US)

(72) Inventors: Matthew W. Bown, West Bountiful, UT (US); Mark A. Christensen, Salt Lake City, UT (US); Guy Rome, Herriman, UT (US); Bret Hamatake, Grantsville, UT (US)

(73) Assignee: C. R. Bard, Inc., Murray Hill, CA (US)

( * ) Notice: Subject to any disclaimer, the term of this patent is extended or adjusted under 35 U.S.C. 154(b) by 418 days.

(21) Appl. No.: 14/317,501

(22) Filed: Jun. 27, 2014

(65) Prior Publication Data

US 2014/0309624 A1    Oct. 16, 2014

Related U.S. Application Data

(62) Division of application No. 11/466,602, filed on Aug. 23, 2006, now Pat. No. 8,784,336.
(Continued)

(51) Int. Cl.
*A61M 25/01* (2006.01)
*A61M 25/00* (2006.01)

(52) U.S. Cl.
CPC .... *A61M 25/0102* (2013.01); *A61M 25/0043* (2013.01); *A61M 25/0127* (2013.01)

(58) Field of Classification Search
CPC .................................................. A61M 25/09
(Continued)

(56) References Cited

U.S. PATENT DOCUMENTS

| 3,133,244 A | 5/1964 | Wojtulewicz |
| 3,297,020 A | 1/1967 | Mathiesen |

(Continued)

FOREIGN PATENT DOCUMENTS

| AU | 642647 | 11/1990 |
| AU | 1860597 B2 | 6/1999 |

(Continued)

OTHER PUBLICATIONS

Zaidi, Naveed A., et al. "Room temperature magnetic order in an organic magnet derived from polyaniline." 2004, Polymer, vol. 45, pp. 5683-5689.*

(Continued)

*Primary Examiner* — Sean Dougherty
*Assistant Examiner* — Patrick Fernandes
(74) *Attorney, Agent, or Firm* — Rutan & Tucker, LLP

(57) ABSTRACT

An elongated medical device includes a core element, a polymer member, a closure element, and a permanent magnetic element. The core element may have a distal region including a first region with a diameter greater than a diameter of a second region, the second region distal of the first region and terminating at a core element distal end. The polymer member may be circumferentially disposed about an entire length of the core element and extending distal of the core element distal end. The closure element may be affixed to a distal end of the polymer member. The permanent magnetic element may be disposed along the second region proximal to the core element distal end, and may include a plurality of permanent magnetic elements spaced apart along the second region.

19 Claims, 20 Drawing Sheets

Related U.S. Application Data

(60) Provisional application No. 60/745,109, filed on Apr. 19, 2006, provisional application No. 60/710,760, filed on Aug. 24, 2005.

(58) Field of Classification Search
USPC .......................... 600/434, 585; 604/164.13
See application file for complete search history.

(56) References Cited

U.S. PATENT DOCUMENTS

| | | |
|---|---|---|
| 3,625,200 A | 12/1971 | Muller |
| 3,674,014 A | 7/1972 | Tillander et al. |
| 3,795,855 A | 3/1974 | Browning |
| 3,817,241 A | 6/1974 | Grausz |
| 3,847,157 A | 11/1974 | Caillouette et al. |
| 3,868,565 A | 2/1975 | Kuipers |
| 3,896,373 A | 7/1975 | Zelby |
| 3,902,501 A | 9/1975 | Citron et al. |
| 3,986,373 A | 10/1976 | Goodlaxson |
| 3,995,623 A | 12/1976 | Blake et al. |
| 4,003,369 A | 1/1977 | Heilman et al. |
| 4,063,561 A | 12/1977 | McKenna |
| 4,072,146 A | 2/1978 | Howes |
| 4,114,601 A | 9/1978 | Abels |
| 4,149,535 A | 4/1979 | Volder et al. |
| 4,173,228 A | 11/1979 | Steenwyk et al. |
| 4,175,566 A | 11/1979 | Millar |
| 4,181,120 A | 1/1980 | Kunii et al. |
| 4,224,949 A | 9/1980 | Scott et al. |
| 4,244,362 A | 1/1981 | Anderson |
| 4,289,139 A | 9/1981 | Enjoji et al. |
| 4,317,078 A | 2/1982 | Weed et al. |
| 4,327,722 A | 5/1982 | Groshong et al. |
| 4,327,723 A | 5/1982 | Frankhouser |
| 4,362,166 A | 12/1982 | Furler et al. |
| 4,365,639 A | 12/1982 | Goldreyer |
| 4,380,237 A | 4/1983 | Newbower |
| 4,407,294 A | 10/1983 | Vilkomerson |
| 4,417,886 A | 11/1983 | Frankhouser et al. |
| 4,429,693 A | 2/1984 | Blake et al. |
| 4,431,005 A | 2/1984 | McCormick |
| 4,431,214 A | 2/1984 | Buffington |
| 4,445,501 A | 5/1984 | Bresler |
| 4,459,854 A | 7/1984 | Richardson et al. |
| 4,469,106 A | 9/1984 | Harui |
| 4,483,343 A | 11/1984 | Beyer et al. |
| 4,491,137 A | 1/1985 | Jingu |
| 4,565,201 A | 1/1986 | Lass |
| 4,572,198 A | 2/1986 | Codrington |
| 4,577,634 A | 3/1986 | Gessman |
| 4,582,067 A | 4/1986 | Silverstein et al. |
| 4,587,975 A | 5/1986 | Salo et al. |
| 4,588,394 A | 5/1986 | Schulte et al. |
| 4,593,687 A | 6/1986 | Gray |
| 4,595,012 A | 6/1986 | Webler et al. |
| 4,601,706 A | 7/1986 | Aillon |
| 4,608,989 A | 9/1986 | Drue |
| 4,608,992 A | 9/1986 | Hakim et al. |
| 4,619,247 A | 10/1986 | Inoue et al. |
| 4,622,644 A | 11/1986 | Hansen |
| 4,644,960 A | 2/1987 | Johans |
| 4,652,820 A | 3/1987 | Maresca |
| 4,660,571 A | 4/1987 | Hess et al. |
| 4,665,925 A | 5/1987 | Millar |
| 4,667,230 A | 5/1987 | Arakawa et al. |
| 4,674,518 A | 6/1987 | Salo |
| 4,676,249 A | 6/1987 | Arenas et al. |
| 4,681,106 A | 7/1987 | Kensey et al. |
| 4,681,117 A | 7/1987 | Brodman et al. |
| 4,688,578 A | 8/1987 | Takano et al. |
| 4,692,148 A | 9/1987 | Kantrowitz et al. |
| 4,697,595 A | 10/1987 | Breyer et al. |
| 4,700,997 A | 10/1987 | Strand |
| 4,706,681 A | 11/1987 | Breyer et al. |
| 4,710,708 A | 12/1987 | Rorden et al. |
| 4,733,669 A | 3/1988 | Segal |
| 4,737,794 A | 4/1988 | Jones |
| 4,741,356 A | 5/1988 | Letzo et al. |
| 4,742,356 A | 5/1988 | Kuipers |
| 4,753,247 A | 6/1988 | Kirsner et al. |
| 4,770,185 A | 9/1988 | Silverstein et al. |
| 4,771,788 A | 9/1988 | Millar |
| 4,781,685 A | 11/1988 | Lehmann et al. |
| 4,784,646 A | 11/1988 | Feingold |
| 4,787,070 A | 11/1988 | Suzuki et al. |
| 4,787,396 A | 11/1988 | Pidorenko |
| 4,790,809 A * | 12/1988 | Kuntz ............................ 604/8 |
| 4,793,361 A | 12/1988 | DuFault |
| 4,794,930 A | 1/1989 | Machida et al. |
| 4,796,632 A | 1/1989 | Boyd et al. |
| 4,798,588 A | 1/1989 | Aillon |
| 4,798,598 A | 1/1989 | Bonello et al. |
| 4,809,681 A | 3/1989 | Kantrowitz et al. |
| 4,809,713 A | 3/1989 | Grayzel |
| 4,813,729 A | 3/1989 | Speckhart |
| 4,821,731 A | 4/1989 | Martinelli et al. |
| 4,836,214 A | 6/1989 | Sramek |
| 4,840,182 A | 6/1989 | Carlson |
| 4,840,622 A | 6/1989 | Hardy |
| 4,841,977 A | 6/1989 | Griffith et al. |
| 4,849,692 A | 7/1989 | Blood |
| 4,850,358 A | 7/1989 | Millar |
| 4,852,580 A | 8/1989 | Wood |
| 4,856,317 A | 8/1989 | Pidorenko et al. |
| 4,856,529 A | 8/1989 | Segal |
| 4,860,757 A | 8/1989 | Lynch et al. |
| 4,867,169 A | 9/1989 | Machida et al. |
| 4,869,263 A | 9/1989 | Segal et al. |
| 4,869,718 A | 9/1989 | Brader |
| 4,873,987 A | 10/1989 | Djordjevich et al. |
| 4,887,606 A | 12/1989 | Yock et al. |
| 4,887,615 A | 12/1989 | Taylor |
| 4,889,128 A | 12/1989 | Millar |
| 4,899,756 A | 2/1990 | Sonek |
| 4,901,725 A | 2/1990 | Nappholz et al. |
| 4,905,698 A | 3/1990 | Strohl, Jr. et al. |
| 4,911,173 A | 3/1990 | Terwilliger |
| 4,911,174 A | 3/1990 | Pederson et al. |
| 4,917,669 A | 4/1990 | Bonaldo |
| 4,924,870 A | 5/1990 | Wlodarczyk et al. |
| 4,943,770 A | 7/1990 | Ashley-Rollman et al. |
| 4,945,305 A | 7/1990 | Blood |
| 4,947,852 A | 8/1990 | Nassi et al. |
| 4,957,110 A | 9/1990 | Vogel et al. |
| 4,957,111 A | 9/1990 | Millar |
| 4,961,433 A | 10/1990 | Christian |
| 4,966,148 A | 10/1990 | Millar |
| 4,967,753 A | 11/1990 | Haase et al. |
| 4,977,886 A | 12/1990 | Takehana et al. |
| 4,989,608 A | 2/1991 | Ratner |
| 4,989,610 A | 2/1991 | Patton et al. |
| 4,995,396 A | 2/1991 | Inaba et al. |
| 4,998,916 A | 3/1991 | Hammerslag et al. |
| 5,004,456 A | 4/1991 | Botterbusch et al. |
| 5,005,592 A | 4/1991 | Cartmell |
| 5,016,173 A | 5/1991 | Kenet et al. |
| 5,025,799 A | 6/1991 | Wilson |
| 5,029,585 A | 7/1991 | Lieber et al. |
| 5,040,548 A | 8/1991 | Yock |
| 5,042,486 A | 8/1991 | Pfeiler et al. |
| 5,045,071 A | 9/1991 | McCormick et al. |
| 5,046,497 A | 9/1991 | Millar |
| 5,050,607 A | 9/1991 | Bradley et al. |
| 5,057,095 A | 10/1991 | Fabian |
| 5,058,583 A | 10/1991 | Geddes et al. |
| 5,058,595 A | 10/1991 | Kern |
| 5,067,489 A | 11/1991 | Lind |
| 5,076,278 A | 12/1991 | Vilkomerson et al. |
| 5,078,140 A | 1/1992 | Kwoh |
| 5,078,148 A | 1/1992 | Nassi et al. |
| 5,078,149 A | 1/1992 | Katsumata et al. |
| 5,078,678 A | 1/1992 | Katims |
| 5,078,714 A | 1/1992 | Katims |
| 5,084,022 A | 1/1992 | Claude |

(56) References Cited

U.S. PATENT DOCUMENTS

| | | |
|---|---|---|
| 5,092,341 A | 3/1992 | Kelen |
| 5,099,845 A | 3/1992 | Besz et al. |
| 5,099,850 A | 3/1992 | Matsui et al. |
| 5,100,387 A | 3/1992 | Ng |
| 5,105,829 A | 4/1992 | Fabian et al. |
| 5,109,862 A | 5/1992 | Kelen et al. |
| 5,114,401 A | 5/1992 | Stuart et al. |
| 5,121,750 A | 6/1992 | Katims |
| 5,125,410 A | 6/1992 | Misono et al. |
| 5,134,370 A | 7/1992 | Jefferts et al. |
| 5,144,955 A | 9/1992 | O'Hara |
| 5,146,151 A | 9/1992 | Korn |
| 5,156,151 A | 10/1992 | Imran |
| 5,158,086 A | 10/1992 | Brown et al. |
| 5,160,342 A | 11/1992 | Reger et al. |
| 5,161,536 A | 11/1992 | Vilkomerson et al. |
| 5,174,295 A | 12/1992 | Christian et al. |
| 5,174,299 A | 12/1992 | Nelson |
| 5,184,601 A | 2/1993 | Putman |
| 5,190,045 A | 3/1993 | Frazin |
| 5,202,985 A | 4/1993 | Goyal |
| 5,205,830 A | 4/1993 | Dassa et al. |
| 5,211,165 A | 5/1993 | Dumoulin et al. |
| 5,211,636 A | 5/1993 | Mische |
| 5,212,988 A | 5/1993 | White et al. |
| 5,214,615 A | 5/1993 | Bauer et al. |
| 5,217,026 A | 6/1993 | Stoy et al. |
| 5,220,924 A | 6/1993 | Frazin |
| 5,233,994 A | 8/1993 | Shmulewitz |
| 5,235,987 A | 8/1993 | Wolfe |
| 5,239,464 A | 8/1993 | Blair et al. |
| 5,240,004 A | 8/1993 | Walinsky et al. |
| 5,243,995 A | 9/1993 | Maier |
| 5,246,007 A | 9/1993 | Frisbie et al. |
| 5,246,426 A | 9/1993 | Lewis et al. |
| 5,247,171 A | 9/1993 | Wlodarczyk et al. |
| 5,251,635 A | 10/1993 | Dumoulin et al. |
| 5,255,680 A | 10/1993 | Darrow et al. |
| 5,257,636 A | 11/1993 | White |
| 5,257,979 A | 11/1993 | Jagpal |
| 5,261,409 A | 11/1993 | Dardel |
| 5,265,610 A | 11/1993 | Darrow et al. |
| 5,265,614 A | 11/1993 | Hayakawa et al. |
| 5,267,569 A | 12/1993 | Lienhard |
| 5,270,810 A | 12/1993 | Nishimura |
| 5,271,404 A | 12/1993 | Corl et al. |
| 5,273,025 A | 12/1993 | Sakiyama et al. |
| 5,273,042 A | 12/1993 | Lynch et al. |
| 5,274,551 A | 12/1993 | Corby, Jr. |
| 5,275,053 A | 1/1994 | Wlodarczyk et al. |
| 5,279,129 A | 1/1994 | Ito |
| 5,279,607 A | 1/1994 | Schentag et al. |
| 5,280,786 A | 1/1994 | Wlodarczyk et al. |
| 5,287,331 A | 2/1994 | Schindel et al. |
| 5,289,373 A | 2/1994 | Zarge et al. |
| 5,292,342 A | 3/1994 | Nelson et al. |
| 5,307,072 A | 4/1994 | Jones, Jr. |
| 5,311,871 A | 5/1994 | Yock |
| 5,313,949 A | 5/1994 | Yock |
| 5,318,025 A | 6/1994 | Dumoulin et al. |
| 5,325,860 A | 7/1994 | Seward et al. |
| 5,325,873 A | 7/1994 | Hirschi et al. |
| 5,330,496 A | 7/1994 | Alferness |
| 5,331,966 A | 7/1994 | Bennett et al. |
| 5,333,614 A | 8/1994 | Feiring |
| 5,337,678 A | 8/1994 | Grout et al. |
| 5,341,807 A | 8/1994 | Nardella |
| 5,343,865 A | 9/1994 | Gardineer et al. |
| 5,345,940 A | 9/1994 | Seward et al. |
| 5,348,020 A | 9/1994 | Hutson |
| 5,350,352 A | 9/1994 | Buchholtz et al. |
| 5,357,961 A | 10/1994 | Fields et al. |
| 5,365,935 A | 11/1994 | Righter et al. |
| 5,366,443 A | 11/1994 | Eggers et al. |
| 5,368,048 A * | 11/1994 | Stoy et al. .............. 600/585 |
| 5,375,596 A | 12/1994 | Twiss et al. |
| 5,376,083 A | 12/1994 | Mische |
| 5,377,678 A | 1/1995 | Dumoulin et al. |
| 5,385,053 A | 1/1995 | Wlodarczyk et al. |
| 5,385,146 A | 1/1995 | Goldreyer |
| 5,391,199 A | 2/1995 | Ben-Haim |
| 5,394,876 A | 3/1995 | Ma |
| 5,394,877 A | 3/1995 | Orr et al. |
| 5,395,366 A | 3/1995 | D'Andrea et al. |
| 5,398,683 A | 3/1995 | Edwards et al. |
| 5,398,691 A | 3/1995 | Martin et al. |
| 5,411,485 A | 5/1995 | Tennican et al. |
| 5,413,107 A | 5/1995 | Oakley et al. |
| 5,417,208 A | 5/1995 | Winkler |
| 5,417,701 A | 5/1995 | Holmes |
| 5,422,478 A | 6/1995 | Wlodarczyk et al. |
| 5,423,334 A | 6/1995 | Jordan |
| 5,423,877 A | 6/1995 | Mackey |
| 5,425,367 A | 6/1995 | Shapiro et al. |
| 5,425,370 A | 6/1995 | Vilkomerson |
| 5,425,382 A | 6/1995 | Golden et al. |
| 5,427,114 A | 6/1995 | Colliver et al. |
| 5,429,132 A | 7/1995 | Guy et al. |
| 5,429,617 A | 7/1995 | Hammersmark et al. |
| 5,431,641 A | 7/1995 | Grozinger et al. |
| 5,433,729 A | 7/1995 | Adams et al. |
| 5,437,276 A | 8/1995 | Takada et al. |
| 5,437,277 A | 8/1995 | Dumoulin et al. |
| 5,438,873 A | 8/1995 | Wlodarczyk et al. |
| 5,443,066 A | 8/1995 | Dumoulin et al. |
| 5,443,489 A | 8/1995 | Ben-Haim |
| 5,445,150 A | 8/1995 | Dumoulin et al. |
| 5,445,166 A | 8/1995 | Taylor |
| 5,450,846 A | 9/1995 | Goldreyer |
| 5,453,575 A | 9/1995 | O'Donnell et al. |
| 5,453,576 A | 9/1995 | Krivitski |
| 5,456,256 A | 10/1995 | Schneider |
| 5,456,718 A | 10/1995 | Szymaitis |
| 5,464,016 A | 11/1995 | Nicholas et al. |
| 5,474,065 A | 12/1995 | Meathrel et al. |
| 5,476,090 A | 12/1995 | Kishi |
| 5,480,422 A | 1/1996 | Ben-Haim |
| 5,487,729 A | 1/1996 | Avellanet et al. |
| 5,490,522 A | 2/1996 | Dardel |
| 5,492,538 A * | 2/1996 | Johlin, Jr. .............. 604/264 |
| 5,494,038 A | 2/1996 | Wang et al. |
| 5,500,011 A | 3/1996 | Desai |
| 5,500,012 A | 3/1996 | Brucker et al. |
| 5,505,205 A | 4/1996 | Solomon et al. |
| 5,509,822 A | 4/1996 | Negus et al. |
| 5,513,637 A | 5/1996 | Twiss et al. |
| 5,515,160 A | 5/1996 | Schulz et al. |
| 5,515,853 A | 5/1996 | Smith et al. |
| 5,517,989 A | 5/1996 | Frisbie et al. |
| 5,522,878 A | 6/1996 | Montecalvo et al. |
| 5,522,880 A | 6/1996 | Barone et al. |
| 5,526,812 A | 6/1996 | Dumoulin et al. |
| 5,531,664 A | 7/1996 | Adachi et al. |
| 5,536,248 A | 7/1996 | Weaver et al. |
| 5,540,230 A | 7/1996 | Vilkomerson |
| 5,540,681 A | 7/1996 | Strul et al. |
| 5,542,938 A | 8/1996 | Avellanet et al. |
| 5,546,949 A | 8/1996 | Frazin et al. |
| 5,546,951 A | 8/1996 | Ben-Haim |
| 5,555,618 A | 9/1996 | Winkler |
| 5,558,091 A | 9/1996 | Acker et al. |
| 5,568,809 A | 10/1996 | Ben-haim |
| D375,450 S | 11/1996 | Bidwell et al. |
| 5,570,671 A | 11/1996 | Hickey |
| 5,575,291 A | 11/1996 | Hayakawa et al. |
| 5,588,442 A | 12/1996 | Scovil et al. |
| 5,592,939 A | 1/1997 | Martinelli |
| 5,598,846 A | 2/1997 | Peszynski |
| 5,599,299 A | 2/1997 | Weaver et al. |
| 5,600,330 A | 2/1997 | Blood |
| 5,603,333 A | 2/1997 | Konings |
| 5,610,967 A | 3/1997 | Moorman et al. |
| 5,617,866 A | 4/1997 | Marian, Jr. |
| 5,622,169 A | 4/1997 | Golden et al. |

(56) References Cited

U.S. PATENT DOCUMENTS

| | | |
|---|---|---|
| 5,622,170 A | 4/1997 | Schulz |
| 5,622,184 A * | 4/1997 | Ashby et al. ............... 600/585 |
| 5,623,931 A | 4/1997 | Wung et al. |
| 5,624,430 A | 4/1997 | Eton et al. |
| 5,626,554 A | 5/1997 | Ryaby et al. |
| 5,626,870 A | 5/1997 | Monshipouri et al. |
| 5,630,419 A | 5/1997 | Ranalletta |
| 5,638,819 A | 6/1997 | Manwaring et al. |
| 5,644,612 A | 7/1997 | Moorman et al. |
| 5,645,065 A | 7/1997 | Shapiro et al. |
| 5,651,047 A | 7/1997 | Moorman et al. |
| 5,654,864 A | 8/1997 | Ritter et al. |
| D383,968 S | 9/1997 | Bidwell et al. |
| 5,662,115 A | 9/1997 | Torp et al. |
| 5,665,103 A | 9/1997 | Lafontaine et al. |
| 5,665,477 A | 9/1997 | Meathrel et al. |
| 5,666,473 A | 9/1997 | Wallace |
| 5,666,958 A | 9/1997 | Rothenberg et al. |
| 5,669,383 A | 9/1997 | Johnson |
| 5,669,388 A | 9/1997 | Vilkomerson |
| 5,676,159 A | 10/1997 | Navis |
| 5,676,673 A | 10/1997 | Ferre et al. |
| 5,682,890 A | 11/1997 | Kormos et al. |
| 5,691,898 A | 11/1997 | Rosenberg et al. |
| 5,694,945 A | 12/1997 | Ben-Haim |
| 5,695,479 A | 12/1997 | Jagpal |
| 5,697,377 A | 12/1997 | Wittkampf |
| 5,699,801 A | 12/1997 | Atalar et al. |
| 5,700,889 A | 12/1997 | Blair |
| 5,701,898 A | 12/1997 | Adam et al. |
| 5,702,433 A | 12/1997 | Taylor et al. |
| 5,711,299 A | 1/1998 | Manwaring et al. |
| 5,713,362 A | 2/1998 | Vilkomerson |
| 5,713,363 A | 2/1998 | Seward et al. |
| 5,713,858 A | 2/1998 | Heruth et al. |
| 5,713,946 A | 2/1998 | Ben-Haim |
| 5,715,817 A | 2/1998 | Stevens-Wright et al. |
| 5,716,389 A | 2/1998 | Walinsky et al. |
| 5,718,241 A | 2/1998 | Ben-Haim et al. |
| D391,838 S | 3/1998 | Bidwell et al. |
| 5,722,412 A | 3/1998 | Pflugrath et al. |
| 5,727,550 A | 3/1998 | Montecalvo |
| 5,727,552 A | 3/1998 | Ryan |
| 5,727,553 A | 3/1998 | Saad |
| 5,729,055 A | 3/1998 | Manning |
| 5,729,129 A | 3/1998 | Acker |
| 5,729,584 A | 3/1998 | Moorman et al. |
| 5,730,129 A | 3/1998 | Darrow et al. |
| 5,731,996 A | 3/1998 | Gilbert |
| 5,733,323 A | 3/1998 | Buck et al. |
| 5,738,096 A | 4/1998 | Ben-Haim |
| 5,740,808 A | 4/1998 | Panescu et al. |
| 5,742,394 A | 4/1998 | Hansen |
| 5,744,953 A | 4/1998 | Hansen |
| 5,748,767 A | 5/1998 | Raab |
| 5,749,835 A | 5/1998 | Glantz |
| 5,749,938 A | 5/1998 | Coombs |
| 5,751,785 A | 5/1998 | Moorman et al. |
| 5,752,513 A | 5/1998 | Acker et al. |
| 5,758,650 A | 6/1998 | Miller et al. |
| 5,762,064 A | 6/1998 | Polvani |
| 5,767,669 A | 6/1998 | Hansen et al. |
| 5,767,960 A | 6/1998 | Orman et al. |
| 5,769,786 A | 6/1998 | Wiegel |
| 5,769,843 A | 6/1998 | Abela et al. |
| 5,769,881 A | 6/1998 | Schroeppel et al. |
| 5,771,896 A | 6/1998 | Sliwa, Jr. et al. |
| 5,775,322 A | 7/1998 | Silverstein et al. |
| 5,775,332 A | 7/1998 | Goldman |
| 5,776,064 A | 7/1998 | Kalfas et al. |
| 5,776,080 A * | 7/1998 | Thome et al. ............... 600/585 |
| 5,779,638 A | 7/1998 | Vesely et al. |
| 5,782,767 A | 7/1998 | Pretlow, III |
| 5,782,773 A | 7/1998 | Kuo et al. |
| 5,785,657 A | 7/1998 | Breyer et al. |
| 5,792,055 A | 8/1998 | McKinnon et al. |
| 5,795,297 A | 8/1998 | Daigle |
| 5,795,298 A | 8/1998 | Vesely et al. |
| 5,795,632 A | 8/1998 | Buchalter |
| 5,797,849 A | 8/1998 | Vesely et al. |
| 5,800,352 A | 9/1998 | Ferre et al. |
| 5,800,410 A | 9/1998 | Gawreluk |
| 5,800,497 A | 9/1998 | Bakels et al. |
| 5,803,089 A | 9/1998 | Ferre et al. |
| 5,810,733 A | 9/1998 | Van Creveld et al. |
| RE35,924 E | 10/1998 | Winkler |
| 5,817,022 A | 10/1998 | Vesely |
| 5,817,024 A | 10/1998 | Ogle et al. |
| 5,820,549 A | 10/1998 | Marian, Jr. |
| 5,824,031 A | 10/1998 | Cookston et al. |
| 5,827,192 A | 10/1998 | Gopakumaran et al. |
| 5,829,444 A | 11/1998 | Ferre et al. |
| 5,830,145 A | 11/1998 | Tenhoff |
| 5,831,260 A | 11/1998 | Hansen |
| 5,833,608 A | 11/1998 | Acker |
| 5,833,622 A | 11/1998 | Meathrel et al. |
| 5,835,561 A | 11/1998 | Moorman et al. |
| 5,836,882 A | 11/1998 | Frazin |
| 5,836,990 A | 11/1998 | Li |
| 5,840,024 A | 11/1998 | Taniguchi et al. |
| 5,840,025 A | 11/1998 | Ben-Haim |
| 5,840,030 A | 11/1998 | Ferek-Petric et al. |
| 5,840,031 A | 11/1998 | Crowley |
| 5,842,986 A | 12/1998 | Avrin et al. |
| 5,842,998 A | 12/1998 | Gopakumaran et al. |
| 5,843,076 A | 12/1998 | Webster, Jr. et al. |
| 5,843,153 A | 12/1998 | Johnston et al. |
| 5,844,140 A | 12/1998 | Seale |
| 5,846,198 A | 12/1998 | Killmann |
| 5,855,553 A | 1/1999 | Tajima et al. |
| 5,859,893 A | 1/1999 | Moorman et al. |
| 5,865,748 A | 2/1999 | Co et al. |
| 5,868,673 A | 2/1999 | Vesely |
| 5,873,822 A | 2/1999 | Ferre et al. |
| 5,876,328 A | 3/1999 | Fox et al. |
| 5,879,297 A | 3/1999 | Haynor et al. |
| 5,893,363 A | 4/1999 | Little et al. |
| 5,897,495 A | 4/1999 | Aida et al. |
| 5,899,860 A | 5/1999 | Pfeiffer et al. |
| 5,902,238 A | 5/1999 | Golden et al. |
| 5,907,487 A | 5/1999 | Rosenberg et al. |
| 5,908,385 A | 6/1999 | Chechelski et al. |
| 5,910,113 A | 6/1999 | Pruter |
| 5,910,120 A | 6/1999 | Kim et al. |
| 5,913,820 A | 6/1999 | Bladen et al. |
| 5,913,830 A | 6/1999 | Miles |
| 5,919,141 A | 7/1999 | Money et al. |
| 5,919,170 A | 7/1999 | Woessner |
| 5,924,998 A * | 7/1999 | Cornelius et al. ............ 600/585 |
| 5,928,145 A | 7/1999 | Ocali et al. |
| 5,929,607 A | 7/1999 | Rosenberg et al. |
| 5,931,788 A | 8/1999 | Keen et al. |
| 5,931,818 A | 8/1999 | Werp et al. |
| 5,931,863 A | 8/1999 | Griffin, III et al. |
| 5,941,858 A | 8/1999 | Johnson |
| 5,941,889 A | 8/1999 | Cermak |
| 5,941,904 A | 8/1999 | Johnston et al. |
| 5,944,022 A | 8/1999 | Nardella et al. |
| 5,944,023 A | 8/1999 | Johnson et al. |
| 5,951,472 A | 9/1999 | Van Vaals et al. |
| 5,951,598 A | 9/1999 | Bishay et al. |
| 5,953,683 A | 9/1999 | Hansen et al. |
| 5,957,857 A | 9/1999 | Hartley |
| 5,961,923 A | 10/1999 | Nova et al. |
| 5,967,978 A | 10/1999 | Littmann et al. |
| 5,967,980 A | 10/1999 | Ferre et al. |
| 5,967,991 A | 10/1999 | Gardineer et al. |
| 5,969,722 A | 10/1999 | Palm |
| 5,971,933 A | 10/1999 | Gopakumaran et al. |
| 5,978,705 A | 11/1999 | KenKnight et al. |
| 5,983,126 A | 11/1999 | Wittkampf |
| 5,984,908 A | 11/1999 | Davis et al. |
| 5,991,693 A | 11/1999 | Zalewski |
| 5,997,473 A | 12/1999 | Taniguchi et al. |

(56) References Cited

U.S. PATENT DOCUMENTS

| | | |
|---|---|---|
| 5,997,481 A | 12/1999 | Adams et al. |
| 6,006,123 A | 12/1999 | Nguyen et al. |
| 6,011,988 A | 1/2000 | Lynch et al. |
| 6,014,473 A | 1/2000 | Hossack et al. |
| 6,014,580 A | 1/2000 | Blume et al. |
| 6,015,414 A | 1/2000 | Werp et al. |
| 6,017,496 A | 1/2000 | Nova et al. |
| 6,019,724 A | 2/2000 | Gronningsaeter et al. |
| 6,019,725 A | 2/2000 | Vesely et al. |
| 6,022,342 A | 2/2000 | Mukherjee |
| 6,023,638 A | 2/2000 | Swanson |
| 6,026,312 A | 2/2000 | Shemwell et al. |
| 6,031,765 A | 2/2000 | Lee et al. |
| 6,032,070 A | 2/2000 | Flock et al. |
| 6,039,694 A | 3/2000 | Larson et al. |
| 6,050,718 A | 4/2000 | Schena et al. |
| 6,052,610 A | 4/2000 | Koch |
| 6,052,618 A | 4/2000 | Dahlke et al. |
| D424,693 S | 5/2000 | Pruter |
| 6,059,718 A | 5/2000 | Taniguchi et al. |
| 6,063,032 A | 5/2000 | Grunwald |
| 6,064,905 A | 5/2000 | Webster, Jr. et al. |
| 6,066,094 A | 5/2000 | Ben-Haim |
| 6,068,599 A | 5/2000 | Saito et al. |
| 6,073,043 A | 6/2000 | Schneider |
| 6,074,367 A | 6/2000 | Hubbell |
| 6,075,442 A | 6/2000 | Welch |
| 6,076,007 A | 6/2000 | England et al. |
| 6,081,737 A | 6/2000 | Shah |
| 6,082,366 A | 7/2000 | Andra et al. |
| 6,083,170 A | 7/2000 | Ben-Haim |
| 6,099,524 A | 8/2000 | Lipson et al. |
| 6,100,026 A | 8/2000 | Nova et al. |
| 6,102,044 A | 8/2000 | Naidyhorski |
| 6,107,699 A | 8/2000 | Swanson |
| 6,112,111 A | 8/2000 | Glantz |
| 6,112,115 A | 8/2000 | Feldman et al. |
| 6,113,504 A | 9/2000 | Kuesters |
| 6,115,624 A | 9/2000 | Lewis et al. |
| 6,120,445 A | 9/2000 | Grunwald |
| 6,128,174 A | 10/2000 | Ritter et al. |
| 6,129,668 A | 10/2000 | Haynor et al. |
| 6,132,378 A | 10/2000 | Marino |
| 6,132,379 A | 10/2000 | Patacsil et al. |
| 6,135,961 A | 10/2000 | Pflugrath et al. |
| 6,136,274 A | 10/2000 | Nova et al. |
| 6,138,681 A | 10/2000 | Chen et al. |
| 6,139,496 A | 10/2000 | Chen et al. |
| 6,139,502 A | 10/2000 | Fredriksen |
| 6,139,540 A | 10/2000 | Rost et al. |
| 6,144,300 A | 11/2000 | Dames et al. |
| 6,148,823 A | 11/2000 | Hastings |
| 6,152,933 A | 11/2000 | Werp et al. |
| 6,157,853 A | 12/2000 | Blume et al. |
| 6,165,144 A | 12/2000 | Talish et al. |
| 6,165,977 A | 12/2000 | Mochly-Rosen |
| 6,166,496 A | 12/2000 | Lys et al. |
| 6,166,806 A | 12/2000 | Tjin |
| 6,167,765 B1 | 1/2001 | Weitzel |
| 6,172,499 B1 | 1/2001 | Ashe |
| 6,173,199 B1 | 1/2001 | Gabriel |
| 6,173,715 B1 | 1/2001 | Sinanan et al. |
| 6,175,756 B1 | 1/2001 | Ferre et al. |
| 6,176,829 B1 | 1/2001 | Vilkomerson |
| 6,187,744 B1 | 2/2001 | Rooney |
| 6,190,370 B1 | 2/2001 | Tsui |
| 6,191,136 B1 | 2/2001 | Marban |
| 6,193,743 B1 | 2/2001 | Brayton et al. |
| 6,197,001 B1 | 3/2001 | Wilson et al. |
| 6,200,305 B1 | 3/2001 | Berthiaume et al. |
| 6,203,499 B1 | 3/2001 | Imling et al. |
| 6,208,884 B1 | 3/2001 | Kumar et al. |
| 6,211,626 B1 | 4/2001 | Lys et al. |
| 6,211,666 B1 | 4/2001 | Acker |
| 6,212,426 B1 | 4/2001 | Swanson |
| 6,216,027 B1 | 4/2001 | Willis et al. |
| 6,216,028 B1 | 4/2001 | Haynor et al. |
| 6,216,029 B1 | 4/2001 | Paltieli |
| 6,223,087 B1 | 4/2001 | Williams |
| 6,226,547 B1 | 5/2001 | Lockhart et al. |
| 6,230,042 B1 | 5/2001 | Slettenmark |
| 6,230,046 B1 | 5/2001 | Crane et al. |
| 6,231,518 B1 | 5/2001 | Grabek et al. |
| 6,233,476 B1 | 5/2001 | Strommer et al. |
| 6,233,994 B1 | 5/2001 | Roy et al. |
| 6,236,883 B1 | 5/2001 | Ciaccio et al. |
| 6,238,344 B1 | 5/2001 | Gamelsky et al. |
| 6,241,673 B1 | 6/2001 | Williams |
| 6,246,231 B1 | 6/2001 | Ashe |
| 6,246,898 B1 | 6/2001 | Vesely et al. |
| 6,248,072 B1 | 6/2001 | Murkin |
| 6,248,074 B1 | 6/2001 | Ohno et al. |
| 6,248,075 B1 | 6/2001 | McGee et al. |
| 6,253,770 B1 | 7/2001 | Acker et al. |
| 6,258,035 B1 | 7/2001 | Hoeksel et al. |
| 6,259,938 B1 | 7/2001 | Zarychta et al. |
| 6,259,941 B1 | 7/2001 | Chia et al. |
| 6,261,231 B1 | 7/2001 | Damphousse et al. |
| 6,263,230 B1 | 7/2001 | Haynor et al. |
| 6,266,550 B1 | 7/2001 | Selmon et al. |
| 6,266,551 B1 | 7/2001 | Osadchy et al. |
| 6,266,552 B1 | 7/2001 | Slettenmark |
| 6,266,563 B1 | 7/2001 | KenKnight et al. |
| 6,270,493 B1 | 8/2001 | Lalonde et al. |
| 6,271,833 B1 | 8/2001 | Rosenberg et al. |
| 6,272,371 B1 | 8/2001 | Shlomo |
| 6,272,374 B1 | 8/2001 | Flock et al. |
| 6,275,258 B1 | 8/2001 | Chim |
| 6,275,724 B1 | 8/2001 | Dickinson et al. |
| 6,277,077 B1 | 8/2001 | Brisken et al. |
| 6,284,459 B1 | 9/2001 | Nova et al. |
| 6,285,898 B1 | 9/2001 | Ben-Haim |
| 6,287,260 B1 | 9/2001 | Hascoet et al. |
| 6,288,704 B1 | 9/2001 | Flack et al. |
| 6,292,678 B1 | 9/2001 | Hall et al. |
| 6,292,680 B1 | 9/2001 | Somogyi et al. |
| 6,292,901 B1 | 9/2001 | Lys et al. |
| 6,293,955 B1 | 9/2001 | Houser et al. |
| 6,296,604 B1 | 10/2001 | Garibaldi et al. |
| 6,298,261 B1 | 10/2001 | Rex |
| 6,304,768 B1 | 10/2001 | Blume et al. |
| 6,306,097 B1 | 10/2001 | Park et al. |
| 6,306,105 B1 * | 10/2001 | Rooney et al. ............... 600/585 |
| 6,311,082 B1 | 10/2001 | Creighton, IV et al. |
| 6,315,709 B1 | 11/2001 | Garibaldi et al. |
| 6,315,727 B1 | 11/2001 | Coleman et al. |
| 6,319,668 B1 | 11/2001 | Nova et al. |
| 6,323,769 B1 | 11/2001 | Dames et al. |
| 6,323,770 B1 | 11/2001 | Dames et al. |
| 6,324,416 B1 | 11/2001 | Seibert |
| 6,325,540 B1 | 12/2001 | Lounsberry et al. |
| 6,325,762 B1 | 12/2001 | Tjin |
| 6,329,139 B1 | 12/2001 | Nova et al. |
| 6,329,916 B1 | 12/2001 | Dames et al. |
| 6,330,467 B1 | 12/2001 | Creighton, IV et al. |
| 6,332,089 B1 | 12/2001 | Acker et al. |
| 6,332,874 B1 | 12/2001 | Eliasen et al. |
| 6,340,588 B1 | 1/2002 | Nova et al. |
| 6,340,868 B1 | 1/2002 | Lys et al. |
| 6,341,231 B1 | 1/2002 | Ferre et al. |
| 6,346,081 B1 | 2/2002 | Vilkomerson |
| 6,348,911 B1 | 2/2002 | Rosenberg et al. |
| 6,350,160 B1 | 2/2002 | Feuersanger et al. |
| 6,352,363 B1 | 3/2002 | Munger et al. |
| 6,354,999 B1 | 3/2002 | Dgany et al. |
| 6,355,026 B1 | 3/2002 | Mick |
| 6,360,123 B1 | 3/2002 | Kimchi et al. |
| 6,361,499 B1 | 3/2002 | Bates et al. |
| 6,364,823 B1 | 4/2002 | Garibaldi et al. |
| 6,364,839 B1 | 4/2002 | Little et al. |
| 6,366,804 B1 | 4/2002 | Mejia |
| 6,368,285 B1 | 4/2002 | Osadchy et al. |
| 6,370,411 B1 | 4/2002 | Osadchy et al. |
| 6,373,240 B1 | 4/2002 | Govari |

(56) References Cited

U.S. PATENT DOCUMENTS

| | | |
|---|---|---|
| 6,373,388 B1 | 4/2002 | Dames et al. |
| 6,374,134 B1 | 4/2002 | Bladen et al. |
| 6,374,670 B1 | 4/2002 | Spelman et al. |
| 6,375,606 B1 | 4/2002 | Garibaldi et al. |
| 6,375,639 B1 | 4/2002 | Duplessie et al. |
| 6,377,857 B1 | 4/2002 | Brayton et al. |
| 6,379,302 B1 | 4/2002 | Kessman et al. |
| 6,379,303 B1 | 4/2002 | Seitz et al. |
| 6,379,307 B1 | 4/2002 | Filly et al. |
| 6,381,485 B1 | 4/2002 | Hunter et al. |
| 6,385,472 B1 | 5/2002 | Hall et al. |
| 6,385,476 B1 | 5/2002 | Osadchy et al. |
| 6,398,736 B1 | 6/2002 | Seward |
| 6,398,738 B1 | 6/2002 | Millar |
| 6,401,723 B1 | 6/2002 | Garibaldi et al. |
| 6,406,422 B1 | 6/2002 | Landesberg |
| 6,406,442 B1 | 6/2002 | McFann et al. |
| 6,412,978 B1 | 7/2002 | Watanabe et al. |
| 6,412,980 B1 | 7/2002 | Lounsberry et al. |
| 6,417,839 B1 | 7/2002 | Odell |
| 6,418,332 B1 | 7/2002 | Mastrototaro et al. |
| 6,418,335 B2 | 7/2002 | Avrin et al. |
| 6,423,002 B1 | 7/2002 | Hossack |
| 6,423,050 B1 | 7/2002 | Twardowski |
| 6,427,079 B1 | 7/2002 | Schneider et al. |
| 6,428,551 B1 | 8/2002 | Hall et al. |
| 6,430,315 B1 | 8/2002 | Makram-Ebeid |
| 6,432,069 B1 | 8/2002 | Godo et al. |
| 6,438,411 B1 | 8/2002 | Guttman et al. |
| 6,442,416 B1 | 8/2002 | Schultz |
| 6,445,943 B1 | 9/2002 | Ferre et al. |
| 6,456,874 B1 | 9/2002 | Hafer et al. |
| 6,459,919 B1 | 10/2002 | Lys et al. |
| 6,463,121 B1 | 10/2002 | Milnes |
| 6,466,815 B1 | 10/2002 | Saito et al. |
| 6,471,656 B1 | 10/2002 | Shalman et al. |
| 6,471,658 B1 | 10/2002 | Daniels et al. |
| 6,471,700 B1 | 10/2002 | Burbank et al. |
| 6,473,167 B1 | 10/2002 | Odell |
| 6,474,341 B1 | 11/2002 | Hunter et al. |
| 6,475,152 B1 | 11/2002 | Kelly, Jr. et al. |
| 6,475,223 B1 | 11/2002 | Werp et al. |
| 6,477,402 B1 | 11/2002 | Lynch et al. |
| 6,484,118 B1 | 11/2002 | Govari et al. |
| 6,487,916 B1 | 12/2002 | Gomm et al. |
| 6,491,671 B1 | 12/2002 | Larson, III et al. |
| 6,493,573 B1 | 12/2002 | Martinelli et al. |
| 6,494,832 B1 | 12/2002 | Feldman et al. |
| 6,496,715 B1 | 12/2002 | Lee et al. |
| 6,498,944 B1 | 12/2002 | Ben-Haim et al. |
| 6,500,141 B1 | 12/2002 | Irion et al. |
| 6,505,062 B1 | 1/2003 | Ritter et al. |
| 6,506,159 B2 | 1/2003 | Hascoet et al. |
| 6,507,751 B2 | 1/2003 | Blume et al. |
| 6,508,802 B1 | 1/2003 | Rosengart et al. |
| 6,511,413 B2 | 1/2003 | Landesberg |
| 6,512,958 B1 | 1/2003 | Swoyer et al. |
| 6,514,226 B1 | 2/2003 | Levin et al. |
| 6,514,249 B1 | 2/2003 | Maguire et al. |
| 6,515,657 B1 | 2/2003 | Zanelli |
| 6,516,212 B1 | 2/2003 | Bladen et al. |
| 6,516,231 B1 | 2/2003 | Flammang |
| 6,516,807 B1 | 2/2003 | Panescu et al. |
| 6,517,520 B2 | 2/2003 | Chang et al. |
| 6,522,906 B1 | 2/2003 | Salisbury, Jr. et al. |
| 6,522,907 B1 | 2/2003 | Bladen et al. |
| 6,522,909 B1 | 2/2003 | Garibaldi et al. |
| 6,524,303 B1 | 2/2003 | Garibaldi |
| 6,528,954 B1 | 3/2003 | Lys et al. |
| 6,528,991 B2 | 3/2003 | Ashe |
| 6,529,761 B2 | 3/2003 | Creighton, IV et al. |
| 6,529,766 B1 | 3/2003 | Guendel |
| 6,534,982 B1 | 3/2003 | Jakab |
| 6,535,625 B1 | 3/2003 | Chang et al. |
| 6,537,192 B1 | 3/2003 | Elliott et al. |
| 6,537,196 B1 | 3/2003 | Creighton, IV et al. |
| 6,538,634 B1 | 3/2003 | Chui et al. |
| 6,540,699 B1 | 4/2003 | Smith et al. |
| 6,542,766 B2 | 4/2003 | Hall et al. |
| 6,544,251 B1 | 4/2003 | Crawford |
| 6,545,678 B1 | 4/2003 | Ohazama |
| 6,546,270 B1 | 4/2003 | Goldin et al. |
| 6,546,279 B1 | 4/2003 | Bova et al. |
| 6,546,787 B1 | 4/2003 | Schiller et al. |
| 6,552,841 B1 | 4/2003 | Lasser et al. |
| 6,556,858 B1 | 4/2003 | Zeman |
| 6,562,019 B1 | 5/2003 | Sell |
| 6,564,087 B1 | 5/2003 | Pitris et al. |
| 6,569,101 B2 | 5/2003 | Quistgaard et al. |
| 6,569,103 B2 | 5/2003 | Hoeksel et al. |
| 6,569,160 B1 | 5/2003 | Goldin et al. |
| 6,569,862 B1 | 5/2003 | Marban |
| 6,571,004 B1 | 5/2003 | Florent et al. |
| 6,574,518 B1 | 6/2003 | Lounsberry et al. |
| 6,575,908 B2 | 6/2003 | Barnes et al. |
| 6,577,080 B2 | 6/2003 | Lys et al. |
| 6,577,896 B2 | 6/2003 | Werner et al. |
| 6,584,343 B1 | 6/2003 | Ransbury et al. |
| 6,593,754 B1 | 7/2003 | Steber et al. |
| 6,593,884 B1 | 7/2003 | Gilboa et al. |
| 6,597,943 B2 | 7/2003 | Taha et al. |
| 6,599,249 B1 | 7/2003 | Nordgren et al. |
| 6,607,488 B1 | 8/2003 | Jackson et al. |
| 6,610,058 B2 | 8/2003 | Flores |
| 6,611,141 B1 | 8/2003 | Schulz et al. |
| 6,615,071 B1 | 9/2003 | Casscells, III et al. |
| 6,615,155 B2 | 9/2003 | Gilboa |
| 6,616,610 B2 | 9/2003 | Steininger et al. |
| 6,618,612 B1 | 9/2003 | Acker et al. |
| 6,626,832 B1 | 9/2003 | Paltieli et al. |
| 6,626,834 B2 | 9/2003 | Dunne et al. |
| 6,626,902 B1 | 9/2003 | Kucharczyk et al. |
| 6,630,879 B1 | 10/2003 | Creighton, IV et al. |
| 6,635,027 B1 | 10/2003 | Cragg et al. |
| 6,645,148 B2 | 11/2003 | Nguyen-Dinh et al. |
| 6,648,875 B2 | 11/2003 | Simpson et al. |
| 6,649,914 B1 | 11/2003 | Moorman et al. |
| 6,652,505 B1 | 11/2003 | Tsugita |
| 6,652,506 B2 | 11/2003 | Bowe et al. |
| 6,660,024 B1 | 12/2003 | Flaherty et al. |
| 6,662,034 B2 | 12/2003 | Segner et al. |
| 6,663,661 B2 | 12/2003 | Boneau |
| 6,666,828 B2 | 12/2003 | Greco et al. |
| 6,672,308 B1 | 1/2004 | Gaspari |
| 6,677,752 B1 | 1/2004 | Creighton, IV et al. |
| 6,679,857 B1 | 1/2004 | Bastia et al. |
| 6,684,176 B2 | 1/2004 | Willins et al. |
| 6,685,644 B2 | 2/2004 | Seo |
| 6,687,531 B1 | 2/2004 | Ferre et al. |
| 6,689,119 B1 | 2/2004 | Di Caprio et al. |
| 6,690,963 B2 | 2/2004 | Ben-Haim et al. |
| 6,690,964 B2 | 2/2004 | Bieger et al. |
| 6,690,968 B2 | 2/2004 | Mejia |
| 6,694,167 B1 | 2/2004 | Ferre et al. |
| 6,695,786 B2 | 2/2004 | Wang et al. |
| 6,701,179 B1 | 3/2004 | Martinelli et al. |
| 6,701,918 B2 | 3/2004 | Fariss et al. |
| 6,702,804 B1 | 3/2004 | Ritter et al. |
| 6,704,590 B2 | 3/2004 | Haldeman |
| 6,709,390 B1 | 3/2004 | Marie Pop |
| 6,711,429 B1 | 3/2004 | Gilboa et al. |
| 6,711,431 B2 | 3/2004 | Sarin et al. |
| 6,719,699 B2 | 4/2004 | Smith |
| 6,719,724 B1 | 4/2004 | Walker et al. |
| 6,719,756 B1 | 4/2004 | Muntermann |
| 6,720,745 B2 | 4/2004 | Lys et al. |
| 6,733,458 B1 | 5/2004 | Steins et al. |
| 6,733,511 B2 | 5/2004 | Hall et al. |
| 6,736,782 B2 | 5/2004 | Pfeiffer et al. |
| 6,738,656 B1 | 5/2004 | Ferre et al. |
| 6,740,103 B2 | 5/2004 | Hall et al. |
| 6,743,177 B2 | 6/2004 | Ito et al. |
| 6,754,596 B2 | 6/2004 | Ashe |
| 6,755,789 B2 | 6/2004 | Stringer et al. |

(56) References Cited

U.S. PATENT DOCUMENTS

| | | |
|---|---|---|
| 6,755,816 B2 | 6/2004 | Ritter et al. |
| 6,755,822 B2 | 6/2004 | Reu et al. |
| 6,757,557 B1 | 6/2004 | Bladen et al. |
| 6,763,261 B2 | 7/2004 | Casscells, III et al. |
| 6,764,449 B2 | 7/2004 | Lee et al. |
| 6,768,496 B2 | 7/2004 | Bieger et al. |
| 6,772,001 B2 | 8/2004 | Maschke et al. |
| 6,774,624 B2 | 8/2004 | Anderson et al. |
| 6,783,536 B2 | 8/2004 | Vilsmeier et al. |
| 6,784,660 B2 | 8/2004 | Ashe |
| 6,785,571 B2 | 8/2004 | Glossop et al. |
| 6,786,219 B2 | 9/2004 | Garibaldi et al. |
| 6,786,870 B2 | 9/2004 | Miyaki et al. |
| 6,788,967 B2 | 9/2004 | Ben-Haim et al. |
| 6,794,667 B2 | 9/2004 | Noshi |
| 6,799,066 B2 | 9/2004 | Steines et al. |
| 6,815,651 B2 | 11/2004 | Odell |
| 6,816,266 B2 | 11/2004 | Varshneya et al. |
| 6,817,364 B2 | 11/2004 | Garibaldi |
| 6,834,201 B2 | 12/2004 | Gillies et al. |
| 6,844,713 B2 | 1/2005 | Steber et al. |
| 6,845,142 B2 | 1/2005 | Ohishi |
| 6,856,823 B2 | 2/2005 | Ashe |
| 6,860,422 B2 | 3/2005 | Hull et al. |
| 6,862,467 B2 | 3/2005 | Moore et al. |
| 6,869,390 B2 | 3/2005 | Elliott et al. |
| 6,875,179 B2 | 4/2005 | Ferguson et al. |
| 6,879,160 B2 | 4/2005 | Jakab |
| 6,887,206 B2 | 5/2005 | Hoeksel et al. |
| 6,889,091 B2 | 5/2005 | Hine et al. |
| 6,895,268 B1 | 5/2005 | Rahn et al. |
| 6,902,528 B1 | 6/2005 | Garibaldi et al. |
| 6,905,469 B2 | 6/2005 | Hascoet et al. |
| 6,908,433 B1 | 6/2005 | Pruter |
| 6,911,026 B1 | 6/2005 | Hall et al. |
| 6,923,782 B2 | 8/2005 | O'Mahony et al. |
| 6,926,673 B2 | 8/2005 | Roberts et al. |
| 6,926,674 B2 | 8/2005 | Tenerz et al. |
| 6,934,575 B2 | 8/2005 | Ferre et al. |
| 6,936,010 B2 | 8/2005 | Fang et al. |
| 6,939,313 B2 | 9/2005 | Saadat et al. |
| 6,940,379 B2 | 9/2005 | Creighton |
| 6,941,166 B2 | 9/2005 | MacAdam et al. |
| 6,947,788 B2 | 9/2005 | Gilboa et al. |
| 6,950,689 B1 | 9/2005 | Willis et al. |
| 6,953,754 B2 | 10/2005 | Machida et al. |
| 6,958,677 B1 | 10/2005 | Carter |
| 6,959,214 B2 | 10/2005 | Pape et al. |
| 6,962,566 B2 | 11/2005 | Quistgaard et al. |
| 6,968,846 B2 | 11/2005 | Viswanathan |
| 6,975,197 B2 | 12/2005 | Creighton, IV |
| 6,976,962 B2 | 12/2005 | Bullis |
| 6,976,987 B2 | 12/2005 | Flores |
| 6,980,843 B2 | 12/2005 | Eng et al. |
| 6,980,852 B2 | 12/2005 | Jersey-Willuhn et al. |
| 6,980,921 B2 | 12/2005 | Anderson et al. |
| 6,986,739 B2 | 1/2006 | Warren et al. |
| 6,986,744 B1 | 1/2006 | Krivitski |
| 6,999,821 B2 | 2/2006 | Jenney et al. |
| 7,001,355 B2 | 2/2006 | Nunomura et al. |
| 7,008,418 B2 | 3/2006 | Hall et al. |
| 7,010,338 B2 | 3/2006 | Ritter et al. |
| 7,015,393 B2 | 3/2006 | Weiner et al. |
| 7,017,584 B2 | 3/2006 | Garibaldi et al. |
| 7,019,610 B2 | 3/2006 | Creighton, IV et al. |
| 7,020,512 B2 | 3/2006 | Ritter et al. |
| D518,574 S | 4/2006 | Chaggares |
| 7,022,075 B2 | 4/2006 | Grunwald et al. |
| 7,022,082 B2 | 4/2006 | Sonek |
| 7,026,927 B2 | 4/2006 | Wright et al. |
| 7,027,634 B2 | 4/2006 | Odell |
| 7,028,387 B1 | 4/2006 | Huynh et al. |
| 7,029,446 B2 | 4/2006 | Wendelken et al. |
| 7,033,603 B2 | 4/2006 | Nelson et al. |
| D520,139 S | 5/2006 | Chaggares |
| D520,140 S | 5/2006 | Chaggares |
| 7,038,398 B1 | 5/2006 | Lys et al. |
| 7,038,657 B2 | 5/2006 | Rosenberg et al. |
| 7,043,293 B1 | 5/2006 | Baura |
| 7,048,733 B2 | 5/2006 | Hartley et al. |
| 7,054,228 B1 | 5/2006 | Hickling |
| 7,065,403 B1 | 6/2006 | Mouchawar et al. |
| 7,066,914 B2 | 6/2006 | Andersen |
| 7,066,924 B1 | 6/2006 | Garibaldi et al. |
| 7,069,072 B2 | 6/2006 | Jansen et al. |
| D525,363 S | 7/2006 | Chaggares |
| 7,070,565 B2 | 7/2006 | Vaezy et al. |
| 7,072,704 B2 | 7/2006 | Bucholz |
| 7,082,325 B2 | 7/2006 | Hashimshony et al. |
| 7,090,639 B2 | 8/2006 | Govari |
| 7,096,059 B2 | 8/2006 | Geddes et al. |
| 7,096,148 B2 | 8/2006 | Anderson et al. |
| 7,096,870 B2 | 8/2006 | Lamprich et al. |
| 7,098,907 B2 | 8/2006 | Houston et al. |
| 7,103,205 B2 | 9/2006 | Wang et al. |
| 7,104,980 B1 | 9/2006 | Laherty et al. |
| 7,106,043 B1 | 9/2006 | Da Silva et al. |
| 7,106,431 B2 | 9/2006 | Odell |
| 7,106,479 B2 | 9/2006 | Roy et al. |
| 7,107,105 B2 | 9/2006 | Bjorklund et al. |
| 7,112,197 B2 | 9/2006 | Hartley et al. |
| 7,128,734 B1 | 10/2006 | Wilson et al. |
| 7,132,804 B2 | 11/2006 | Lys et al. |
| 7,137,976 B2 | 11/2006 | Ritter et al. |
| 7,141,019 B2 | 11/2006 | Pearlman |
| 7,141,812 B2 | 11/2006 | Appleby et al. |
| 7,142,905 B2 | 11/2006 | Slayton et al. |
| 7,148,970 B2 | 12/2006 | de Boer |
| 7,153,291 B2 | 12/2006 | Bierman |
| 7,161,453 B2 | 1/2007 | Creighton, IV |
| 7,162,291 B1 | 1/2007 | Nachaliel |
| 7,167,738 B2 | 1/2007 | Schweikard et al. |
| 7,169,107 B2 | 1/2007 | Jersey-Willuhn et al. |
| 7,169,109 B2 | 1/2007 | Jansen et al. |
| 7,174,201 B2 | 2/2007 | Govari et al. |
| 7,175,646 B2 | 2/2007 | Brenneman et al. |
| 7,180,252 B2 | 2/2007 | Lys et al. |
| 7,184,820 B2 | 2/2007 | Jersey-Willuhn et al. |
| 7,189,198 B2 | 3/2007 | Harburn et al. |
| 7,189,205 B2 | 3/2007 | McMorrow et al. |
| 7,189,208 B1 | 3/2007 | Beatty et al. |
| 7,190,819 B2 | 3/2007 | Viswanathan |
| 7,194,295 B2 | 3/2007 | Vilsmeier |
| 7,204,798 B2 | 4/2007 | Zdeblick et al. |
| 7,206,064 B2 | 4/2007 | Rogers et al. |
| 7,207,941 B2 | 4/2007 | Sharf |
| 7,211,082 B2 | 5/2007 | Hall et al. |
| 7,214,191 B2 | 5/2007 | Stringer et al. |
| 7,215,326 B2 | 5/2007 | Rosenberg |
| 7,221,104 B2 | 5/2007 | Lys et al. |
| 7,223,256 B2 | 5/2007 | Bierman |
| 7,229,400 B2 | 6/2007 | Elliott et al. |
| 7,231,243 B2 | 6/2007 | Tearney et al. |
| 7,236,157 B2 | 6/2007 | Schena et al. |
| 7,236,816 B2 | 6/2007 | Kumar et al. |
| 7,236,820 B2 | 6/2007 | Mabary et al. |
| 7,237,313 B2 | 7/2007 | Skujins et al. |
| 7,241,267 B2 | 7/2007 | Furia |
| 7,244,234 B2 | 7/2007 | Ridley et al. |
| 7,248,032 B1 | 7/2007 | Hular et al. |
| 7,248,914 B2 | 7/2007 | Hastings et al. |
| 7,252,633 B2 | 8/2007 | Obata et al. |
| 7,264,584 B2 | 9/2007 | Ritter et al. |
| 7,270,662 B2 | 9/2007 | Visram et al. |
| 7,276,044 B2 | 10/2007 | Ferry et al. |
| 7,286,034 B2 | 10/2007 | Creighton |
| 7,291,146 B2 | 11/2007 | Steinke et al. |
| 7,297,140 B2 | 11/2007 | Orlu et al. |
| 7,300,430 B2 | 11/2007 | Wilson et al. |
| 7,302,288 B1 | 11/2007 | Schellenberg |
| 7,308,296 B2 | 12/2007 | Lys et al. |
| 7,310,150 B2 | 12/2007 | Guillermo et al. |
| 7,311,702 B2 | 12/2007 | Tallarida et al. |
| 7,321,228 B2 | 1/2008 | Govari |

(56) References Cited

U.S. PATENT DOCUMENTS

| | | |
|---|---|---|
| 7,326,241 B2 | 2/2008 | Jang |
| 7,327,872 B2 | 2/2008 | Vaillant et al. |
| 7,342,058 B2 | 3/2008 | Peppmoller et al. |
| 7,349,732 B1 | 3/2008 | Kil et al. |
| 7,355,716 B2 | 4/2008 | de Boer et al. |
| 7,360,427 B2 | 4/2008 | Drinkwater et al. |
| 7,366,376 B2 | 4/2008 | Shishkov et al. |
| 7,366,562 B2 | 4/2008 | Dukesherer et al. |
| 7,366,563 B2 | 4/2008 | Kleen et al. |
| 7,373,271 B1 | 5/2008 | Schneider |
| 7,381,204 B2 | 6/2008 | Wilson et al. |
| 7,382,949 B2 | 6/2008 | Bouma et al. |
| 7,384,407 B2 | 6/2008 | Rodriguez et al. |
| 7,418,169 B2 | 8/2008 | Tearney et al. |
| 7,447,408 B2 | 11/2008 | Bouma et al. |
| 7,452,331 B1 | 11/2008 | Pruter |
| 7,452,358 B2 | 11/2008 | Stern et al. |
| 7,454,244 B2 | 11/2008 | Kassab et al. |
| D585,556 S | 1/2009 | Kosaku |
| 7,479,141 B2 | 1/2009 | Kleen et al. |
| 7,519,424 B2 | 4/2009 | Dennis et al. |
| 7,534,223 B2 | 5/2009 | Boutilette et al. |
| 7,538,859 B2 | 5/2009 | Tearney et al. |
| 7,543,239 B2 | 6/2009 | Viswanathan et al. |
| 7,546,158 B2 | 6/2009 | Allison et al. |
| 7,547,282 B2 | 6/2009 | Lo et al. |
| 7,551,293 B2 | 6/2009 | Yelin et al. |
| D603,050 S | 10/2009 | Chen |
| 7,599,730 B2 | 10/2009 | Hunter et al. |
| 7,606,615 B2 | 10/2009 | Makower et al. |
| 7,616,992 B2 | 11/2009 | Dennis et al. |
| 7,627,376 B2 | 12/2009 | Dennis et al. |
| 7,635,336 B1 | 12/2009 | Pruter |
| 7,637,163 B2 | 12/2009 | Fetzer et al. |
| 7,640,053 B2 | 12/2009 | Verin |
| 7,651,469 B2 | 1/2010 | Osborne et al. |
| 7,652,080 B2 | 1/2010 | Peppmoller et al. |
| 7,660,623 B2 | 2/2010 | Hunter et al. |
| 7,665,893 B2 | 2/2010 | Buchalter |
| 7,668,583 B2 | 2/2010 | Fegert et al. |
| 7,697,972 B2 | 4/2010 | Verard et al. |
| 7,699,782 B2 | 4/2010 | Angelsen et al. |
| 7,699,829 B2 | 4/2010 | Harris et al. |
| 7,715,925 B2 | 5/2010 | Hafer et al. |
| 7,727,192 B2 | 6/2010 | Tokumoto et al. |
| 7,729,743 B2 | 6/2010 | Sabczynski et al. |
| 7,751,865 B2 | 7/2010 | Jascob et al. |
| 7,766,839 B2 | 8/2010 | Rogers et al. |
| 7,771,437 B2 | 8/2010 | Hogg et al. |
| 7,774,051 B2 | 8/2010 | Voth |
| 7,774,055 B1 | 8/2010 | Min |
| 7,794,407 B2 | 9/2010 | Rothenberg |
| 7,798,970 B2 | 9/2010 | Lo et al. |
| 7,819,810 B2 | 10/2010 | Stringer et al. |
| 7,828,528 B2 | 11/2010 | Estes et al. |
| 7,831,294 B2 | 11/2010 | Viswanathan |
| 7,833,168 B2 | 11/2010 | Taylor et al. |
| 7,833,214 B2 | 11/2010 | Wilson et al. |
| D629,526 S | 12/2010 | Ladwig et al. |
| D629,527 S | 12/2010 | Crunkilton |
| 7,846,157 B2 | 12/2010 | Kozel |
| 7,850,613 B2 | 12/2010 | Stribling |
| D630,756 S | 1/2011 | Kitayama |
| D630,757 S | 1/2011 | Kitayama |
| 7,869,854 B2 | 1/2011 | Shachar et al. |
| 7,873,402 B2 | 1/2011 | Shachar |
| 7,909,815 B2 | 3/2011 | Whitmore, III et al. |
| 7,931,596 B2 | 4/2011 | Rachlin et al. |
| 7,947,040 B2 | 5/2011 | Davies et al. |
| 7,976,469 B2 | 7/2011 | Bonde et al. |
| 7,976,518 B2 | 7/2011 | Shaughnessy et al. |
| 7,981,038 B2 | 7/2011 | Kanade et al. |
| 7,988,633 B2 | 8/2011 | Hossack et al. |
| 8,016,814 B2 | 9/2011 | Blakstvedt et al. |
| 8,046,052 B2 | 10/2011 | Verard et al. |
| 8,057,394 B2 | 11/2011 | Dala-Krishna |
| 8,060,185 B2 | 11/2011 | Hunter et al. |
| 8,078,274 B2 | 12/2011 | Kassab |
| 8,078,279 B2 | 12/2011 | Dennis et al. |
| 8,082,032 B2 | 12/2011 | Kassab et al. |
| 8,088,072 B2 | 1/2012 | Munrow et al. |
| 8,090,430 B2 | 1/2012 | Makower et al. |
| 8,099,161 B2 | 1/2012 | Kassab |
| 8,114,143 B2 | 2/2012 | Kassab et al. |
| 8,118,743 B2 | 2/2012 | Park et al. |
| 8,123,691 B2 | 2/2012 | Mine et al. |
| 8,133,698 B2 | 3/2012 | Silver |
| 8,142,417 B2 | 3/2012 | Pajunk et al. |
| 8,150,522 B2 | 4/2012 | Echauz et al. |
| 8,152,724 B2 | 4/2012 | Ridley et al. |
| 8,204,582 B2 | 6/2012 | Zantos et al. |
| 8,214,018 B2 | 7/2012 | Markowitz et al. |
| 8,221,402 B2 | 7/2012 | Francischelli et al. |
| 8,240,211 B2 | 8/2012 | Zeitner et al. |
| 8,241,274 B2 | 8/2012 | Keogh et al. |
| 8,244,339 B2 | 8/2012 | Shen et al. |
| 8,255,035 B2 | 8/2012 | Cao et al. |
| 8,260,395 B2 | 9/2012 | Markowitz et al. |
| 8,262,577 B2 | 9/2012 | Munrow et al. |
| 8,298,149 B2 | 10/2012 | Hastings et al. |
| 8,303,502 B2 | 11/2012 | Washburn et al. |
| 8,303,505 B2 | 11/2012 | Webler et al. |
| 8,326,419 B2 | 12/2012 | Rosenberg et al. |
| 8,340,751 B2 | 12/2012 | Markowitz et al. |
| 8,369,922 B2 | 2/2013 | Paul et al. |
| 8,388,541 B2 | 3/2013 | Messerly et al. |
| 8,388,546 B2 | 3/2013 | Rothenberg |
| 8,391,956 B2 | 3/2013 | Zellers et al. |
| 8,401,616 B2 | 3/2013 | Verard et al. |
| 8,409,103 B2 | 4/2013 | Grunwald et al. |
| 8,425,425 B2 | 4/2013 | Hagy et al. |
| 8,437,833 B2 | 5/2013 | Silverstein |
| 8,439,873 B1 | 5/2013 | Donovan |
| 8,442,621 B2 | 5/2013 | Gorek et al. |
| 8,447,384 B2 | 5/2013 | Xu et al. |
| D684,265 S | 6/2013 | Cadera |
| 8,456,182 B2 | 6/2013 | Bar-Tal et al. |
| 8,478,382 B2 | 7/2013 | Burnside et al. |
| 8,485,980 B2 | 7/2013 | Sinderby et al. |
| 8,494,608 B2 | 7/2013 | Markowitz et al. |
| 8,496,592 B2 | 7/2013 | Ridley et al. |
| 8,504,139 B2 | 8/2013 | Jacobsen et al. |
| 8,512,256 B2 | 8/2013 | Rothenberg |
| 8,527,036 B2 | 9/2013 | Jalde et al. |
| 8,538,509 B2 | 9/2013 | Harlev et al. |
| 8,597,193 B2 | 12/2013 | Grunwald et al. |
| 8,644,907 B2 | 2/2014 | Hartmann et al. |
| 8,690,776 B2 | 4/2014 | Razzaque et al. |
| 8,734,440 B2 | 5/2014 | Wu |
| 8,774,907 B2 | 7/2014 | Rothenberg |
| 8,781,555 B2 | 7/2014 | Burnside et al. |
| 8,784,336 B2 | 7/2014 | Bown et al. |
| 8,801,693 B2 | 8/2014 | He et al. |
| 8,849,382 B2 | 9/2014 | Cox et al. |
| 8,858,455 B2 | 10/2014 | Rothenberg |
| 8,934,961 B2 | 1/2015 | Lakin et al. |
| 9,125,578 B2 | 9/2015 | Grunwald |
| 9,339,206 B2 | 5/2016 | Grunwald |
| 9,456,766 B2 | 10/2016 | Cox et al. |
| 9,492,097 B2 | 11/2016 | Wilkes et al. |
| 9,521,961 B2 | 12/2016 | Silverstein et al. |
| 9,526,440 B2 | 12/2016 | Burnside et al. |
| 9,532,724 B2 | 1/2017 | Grunwald |
| 9,554,716 B2 | 1/2017 | Burnside et al. |
| 9,636,031 B2 | 5/2017 | Cox |
| 9,642,986 B2 | 5/2017 | Beasley |
| 9,649,048 B2 | 5/2017 | Cox et al. |
| 9,681,823 B2 | 6/2017 | Messerly et al. |
| 9,833,169 B2 | 12/2017 | Rothenberg |
| 9,839,372 B2 | 12/2017 | Bukhman et al. |
| 9,901,714 B2 | 2/2018 | Lemon et al. |
| 9,907,513 B2 | 3/2018 | Silverstein |
| 2002/0010392 A1 | 1/2002 | Desai |
| 2002/0016549 A1 | 2/2002 | Mejia |

(56) References Cited

U.S. PATENT DOCUMENTS

| | | |
|---|---|---|
| 2002/0019447 A1 | 2/2002 | Renn et al. |
| 2002/0022777 A1 | 2/2002 | Crieghton et al. |
| 2002/0032391 A1 | 3/2002 | McFann et al. |
| 2002/0049488 A1 | 4/2002 | Boneau |
| 2002/0055680 A1 | 5/2002 | Miele et al. |
| 2002/0082559 A1 | 6/2002 | Chang et al. |
| 2002/0113555 A1 | 8/2002 | Lys et al. |
| 2002/0123679 A1 | 9/2002 | Dominguez |
| 2002/0128554 A1 | 9/2002 | Seward |
| 2002/0129952 A1 | 9/2002 | Matsudate et al. |
| 2002/0133079 A1 | 9/2002 | Sandhu |
| 2002/0156363 A1 | 10/2002 | Hunter et al. |
| 2002/0156376 A1 | 10/2002 | Wang et al. |
| 2002/0165448 A1 | 11/2002 | Ben-Haim et al. |
| 2002/0165534 A1 | 11/2002 | Hayzelden et al. |
| 2002/0165537 A1 | 11/2002 | Kelley et al. |
| 2002/0173721 A1 | 11/2002 | Grunwald et al. |
| 2002/0193756 A1 | 12/2002 | Prindle |
| 2002/0198568 A1 | 12/2002 | Hafer et al. |
| 2003/0009132 A1 | 1/2003 | Schwartz et al. |
| 2003/0011359 A1 | 1/2003 | Ashe |
| 2003/0013966 A1 | 1/2003 | Barnes et al. |
| 2003/0013986 A1 | 1/2003 | Saadat |
| 2003/0018251 A1 | 1/2003 | Solomon |
| 2003/0036696 A1 | 2/2003 | Willis et al. |
| 2003/0040671 A1 | 2/2003 | Somogyi et al. |
| 2003/0040743 A1 | 2/2003 | Cosman et al. |
| 2003/0072805 A1 | 4/2003 | Miyazawa et al. |
| 2003/0073901 A1 | 4/2003 | Simon et al. |
| 2003/0076281 A1 | 4/2003 | Morgan et al. |
| 2003/0083698 A1 | 5/2003 | Whitehurst et al. |
| 2003/0088195 A1 | 5/2003 | Vardi et al. |
| 2003/0100849 A1 | 5/2003 | Jang |
| 2003/0114742 A1 | 6/2003 | Lewkowicz et al. |
| 2003/0114777 A1 | 6/2003 | Griffin et al. |
| 2003/0120150 A1 | 6/2003 | Govari |
| 2003/0120154 A1 | 6/2003 | Sauer et al. |
| 2003/0139661 A1 | 7/2003 | Kimchy et al. |
| 2003/0149328 A1 | 8/2003 | Elliott et al. |
| 2003/0149368 A1 | 8/2003 | Hennemann et al. |
| 2003/0152290 A1 | 8/2003 | Odell |
| 2003/0160721 A1 | 8/2003 | Gilboa et al. |
| 2003/0162414 A1 | 8/2003 | Schulz et al. |
| 2003/0163037 A1 | 8/2003 | Bladen et al. |
| 2003/0163142 A1 | 8/2003 | Paltieli et al. |
| 2003/0171691 A1 | 9/2003 | Casscells et al. |
| 2003/0173953 A1 | 9/2003 | Ashe |
| 2003/0181892 A1 | 9/2003 | Pajunk et al. |
| 2003/0184544 A1 | 10/2003 | Prudent |
| 2003/0191392 A1 | 10/2003 | Haldeman |
| 2003/0191460 A1 | 10/2003 | Hobbs et al. |
| 2003/0195420 A1 | 10/2003 | Mendlein et al. |
| 2003/0199746 A1 | 10/2003 | Fuimaono et al. |
| 2003/0208142 A1* | 11/2003 | Boudewijn et al. .......... 600/585 |
| 2003/0216639 A1 | 11/2003 | Gilboa et al. |
| 2003/0220557 A1 | 11/2003 | Cleary et al. |
| 2003/0220578 A1 | 11/2003 | Ho et al. |
| 2003/0229298 A1 | 12/2003 | Iwami et al. |
| 2003/0233042 A1 | 12/2003 | Ashe |
| 2003/0236445 A1 | 12/2003 | Couvillon |
| 2004/0010189 A1 | 1/2004 | van Sloun et al. |
| 2004/0015070 A1 | 1/2004 | Liang et al. |
| 2004/0024301 A1 | 2/2004 | Hockett et al. |
| 2004/0030319 A1 | 2/2004 | Korkor et al. |
| 2004/0054278 A1 | 3/2004 | Kimchy et al. |
| 2004/0059237 A1 | 3/2004 | Narayan et al. |
| 2004/0082916 A1 | 4/2004 | Jenkins |
| 2004/0087877 A1 | 5/2004 | Besz et al. |
| 2004/0088136 A1 | 5/2004 | Ashe |
| 2004/0092962 A1 | 5/2004 | Thornton et al. |
| 2004/0097803 A1 | 5/2004 | Panescu |
| 2004/0097804 A1 | 5/2004 | Sobe |
| 2004/0097805 A1 | 5/2004 | Verard et al. |
| 2004/0097806 A1 | 5/2004 | Hunter et al. |
| 2004/0116809 A1 | 6/2004 | Chow et al. |
| 2004/0127805 A1 | 7/2004 | MacAdam et al. |
| 2004/0131998 A1 | 7/2004 | Marom et al. |
| 2004/0133111 A1 | 7/2004 | Szczech et al. |
| 2004/0133130 A1 | 7/2004 | Ferry et al. |
| 2004/0135069 A1 | 7/2004 | Odell |
| 2004/0138557 A1 | 7/2004 | Le et al. |
| 2004/0138564 A1 | 7/2004 | Hwang et al. |
| 2004/0138570 A1 | 7/2004 | Nita et al. |
| 2004/0147837 A1 | 7/2004 | Macaulay et al. |
| 2004/0150963 A1 | 8/2004 | Holmberg et al. |
| 2004/0152972 A1 | 8/2004 | Hunter |
| 2004/0155609 A1 | 8/2004 | Lys et al. |
| 2004/0158140 A1 | 8/2004 | Fuimaono et al. |
| 2004/0171924 A1 | 9/2004 | Mire et al. |
| 2004/0176688 A1 | 9/2004 | Haldeman |
| 2004/0186461 A1 | 9/2004 | DiMatteo |
| 2004/0199069 A1 | 10/2004 | Connelly et al. |
| 2004/0210289 A1 | 10/2004 | Wang et al. |
| 2004/0225233 A1* | 11/2004 | Frankowski et al. ......... 600/585 |
| 2004/0230131 A1 | 11/2004 | Kassab et al. |
| 2004/0230271 A1 | 11/2004 | Wang et al. |
| 2004/0234453 A1 | 11/2004 | Smith |
| 2004/0243018 A1 | 12/2004 | Organ et al. |
| 2004/0243116 A1 | 12/2004 | Joye et al. |
| 2004/0243118 A1 | 12/2004 | Ayers et al. |
| 2004/0253365 A1 | 12/2004 | Warren et al. |
| 2004/0254470 A1 | 12/2004 | Drinkwater et al. |
| 2004/0254495 A1 | 12/2004 | Mabary et al. |
| 2004/0260174 A1 | 12/2004 | Keene |
| 2004/0267086 A1 | 12/2004 | Anstadt et al. |
| 2005/0004450 A1 | 1/2005 | Ben-Haim et al. |
| 2005/0021019 A1 | 1/2005 | Hashimshony et al. |
| 2005/0033150 A1 | 2/2005 | Takahashi et al. |
| 2005/0038355 A1 | 2/2005 | Gellman et al. |
| 2005/0043640 A1 | 2/2005 | Chang |
| 2005/0049486 A1 | 3/2005 | Urquhart et al. |
| 2005/0049510 A1 | 3/2005 | Haldeman et al. |
| 2005/0063194 A1 | 3/2005 | Lys et al. |
| 2005/0070788 A1 | 3/2005 | Wilson et al. |
| 2005/0075561 A1 | 4/2005 | Golden |
| 2005/0085715 A1 | 4/2005 | Dukesherer et al. |
| 2005/0085716 A1 | 4/2005 | Hamm et al. |
| 2005/0085718 A1 | 4/2005 | Shahidi |
| 2005/0085720 A1 | 4/2005 | Jascob et al. |
| 2005/0090746 A1 | 4/2005 | Ohtake |
| 2005/0101868 A1 | 5/2005 | Ridley et al. |
| 2005/0101869 A1 | 5/2005 | Burba et al. |
| 2005/0105081 A1 | 5/2005 | Odell |
| 2005/0105101 A1 | 5/2005 | Duling et al. |
| 2005/0112135 A1 | 5/2005 | Cormier et al. |
| 2005/0113669 A1 | 5/2005 | Helfer et al. |
| 2005/0113676 A1 | 5/2005 | Weiner et al. |
| 2005/0113700 A1 | 5/2005 | Yanagihara et al. |
| 2005/0113873 A1 | 5/2005 | Weiner et al. |
| 2005/0113874 A1 | 5/2005 | Connelly et al. |
| 2005/0113876 A1 | 5/2005 | Weiner et al. |
| 2005/0148836 A1 | 7/2005 | Kleen et al. |
| 2005/0148902 A1 | 7/2005 | Minar et al. |
| 2005/0149002 A1 | 7/2005 | Wang et al. |
| 2005/0151489 A1 | 7/2005 | Lys et al. |
| 2005/0154308 A1 | 7/2005 | Quistgaard et al. |
| 2005/0159644 A1 | 7/2005 | Takano |
| 2005/0159790 A1 | 7/2005 | Shalev |
| 2005/0165301 A1 | 7/2005 | Smith et al. |
| 2005/0165313 A1 | 7/2005 | Byron et al. |
| 2005/0175665 A1 | 8/2005 | Hunter et al. |
| 2005/0175703 A1 | 8/2005 | Hunter et al. |
| 2005/0178395 A1 | 8/2005 | Hunter et al. |
| 2005/0178396 A1 | 8/2005 | Hunter et al. |
| 2005/0182295 A1 | 8/2005 | Soper et al. |
| 2005/0182454 A1 | 8/2005 | Gharib et al. |
| 2005/0197674 A1 | 9/2005 | McCabe et al. |
| 2005/0203368 A1 | 9/2005 | Verin |
| 2005/0203396 A1 | 9/2005 | Angelsen et al. |
| 2005/0205081 A1 | 9/2005 | Barker et al. |
| 2005/0215901 A1 | 9/2005 | Anderson et al. |
| 2005/0215945 A1 | 9/2005 | Harris et al. |
| 2005/0222532 A1 | 10/2005 | Bertolero et al. |
| 2005/0240102 A1 | 10/2005 | Rachlin et al. |

(56) References Cited

U.S. PATENT DOCUMENTS

| | | |
|---|---|---|
| 2005/0245811 A1 | 11/2005 | Scheffler |
| 2005/0256398 A1 | 11/2005 | Hastings et al. |
| 2005/0256451 A1 | 11/2005 | Adams et al. |
| 2005/0256521 A1 | 11/2005 | Kozel |
| 2005/0256541 A1 | 11/2005 | Stypulkowski |
| 2005/0283210 A1 | 12/2005 | Blischak et al. |
| 2005/0283216 A1 | 12/2005 | Pyles |
| 2005/0288586 A1 | 12/2005 | Ferek-Petric |
| 2006/0009759 A1 | 1/2006 | Chrisitian et al. |
| 2006/0015003 A1 | 1/2006 | Moaddes et al. |
| 2006/0025677 A1 | 2/2006 | Verard et al. |
| 2006/0025697 A1 | 2/2006 | Kurzweil et al. |
| 2006/0058633 A1 | 3/2006 | Hoshino et al. |
| 2006/0068074 A1 | 3/2006 | Stefandl |
| 2006/0084867 A1 | 4/2006 | Tremblay et al. |
| 2006/0106306 A1 | 5/2006 | Essner et al. |
| 2006/0116571 A1 | 6/2006 | Maschke et al. |
| 2006/0116576 A1 | 6/2006 | McGee et al. |
| 2006/0116578 A1 | 6/2006 | Grunwald et al. |
| 2006/0142656 A1 | 6/2006 | Malackowski et al. |
| 2006/0149134 A1 | 7/2006 | Soper et al. |
| 2006/0173251 A1 | 8/2006 | Govari et al. |
| 2006/0173329 A1 | 8/2006 | Irioka et al. |
| 2006/0173407 A1 | 8/2006 | Shaughnessy et al. |
| 2006/0176242 A1 | 8/2006 | Jaramaz et al. |
| 2006/0184074 A1 | 8/2006 | Vaezy et al. |
| 2006/0206037 A1 | 9/2006 | Braxton |
| 2006/0211944 A1 | 9/2006 | Mauge et al. |
| 2006/0217655 A1 | 9/2006 | Vitullo et al. |
| 2006/0224188 A1 | 10/2006 | Libbus et al. |
| 2006/0241432 A1 | 10/2006 | Herline et al. |
| 2006/0247746 A1 | 11/2006 | Danek et al. |
| 2006/0253029 A1 | 11/2006 | Altmann et al. |
| 2006/0258895 A1 | 11/2006 | Maschke |
| 2006/0276867 A1 | 12/2006 | Viswanathan |
| 2006/0287595 A1 | 12/2006 | Maschke |
| 2007/0010753 A1 | 1/2007 | MacAdam |
| 2007/0016007 A1 | 1/2007 | Govari et al. |
| 2007/0016013 A1 | 1/2007 | Camus |
| 2007/0016068 A1 | 1/2007 | Grunwald et al. |
| 2007/0016069 A1 | 1/2007 | Grunwald et al. |
| 2007/0016070 A1 | 1/2007 | Grunwald et al. |
| 2007/0016072 A1 | 1/2007 | Grunwald et al. |
| 2007/0032746 A1* | 2/2007 | Sell ............................ 600/585 |
| 2007/0038113 A1 | 2/2007 | Oonuki et al. |
| 2007/0049822 A1 | 3/2007 | Bunce et al. |
| 2007/0049846 A1 | 3/2007 | Bown et al. |
| 2007/0055141 A1 | 3/2007 | Kruger et al. |
| 2007/0055142 A1 | 3/2007 | Webler |
| 2007/0055294 A1 | 3/2007 | Giap |
| 2007/0060992 A1 | 3/2007 | Pappone |
| 2007/0062544 A1 | 3/2007 | Rauk Bergstrom et al. |
| 2007/0066888 A1 | 3/2007 | Maschke |
| 2007/0073155 A1 | 3/2007 | Park et al. |
| 2007/0078343 A1 | 4/2007 | Kawashima et al. |
| 2007/0087038 A1 | 4/2007 | Richardson et al. |
| 2007/0093710 A1 | 4/2007 | Maschke |
| 2007/0100236 A1 | 5/2007 | McMorrow et al. |
| 2007/0100285 A1 | 5/2007 | Griffin et al. |
| 2007/0112282 A1 | 5/2007 | Skujins et al. |
| 2007/0123805 A1 | 5/2007 | Shireman et al. |
| 2007/0129770 A1 | 6/2007 | Younis |
| 2007/0135803 A1 | 6/2007 | Belson |
| 2007/0135886 A1 | 6/2007 | Maschke |
| 2007/0156205 A1 | 7/2007 | Larson et al. |
| 2007/0161853 A1 | 7/2007 | Yagi et al. |
| 2007/0161914 A1 | 7/2007 | Zdeblick et al. |
| 2007/0161915 A1 | 7/2007 | Desai |
| 2007/0167738 A1 | 7/2007 | Timinger et al. |
| 2007/0167762 A1 | 7/2007 | Kim et al. |
| 2007/0167769 A1 | 7/2007 | Ikuma et al. |
| 2007/0167801 A1 | 7/2007 | Webler et al. |
| 2007/0167997 A1 | 7/2007 | Forsberg et al. |
| 2007/0197891 A1 | 8/2007 | Shachar et al. |
| 2007/0197905 A1 | 8/2007 | Timinger et al. |
| 2007/0208255 A1 | 9/2007 | Ridley et al. |
| 2007/0219453 A1 | 9/2007 | Kremliovsky et al. |
| 2007/0225589 A1 | 9/2007 | Viswanathan |
| 2007/0225610 A1 | 9/2007 | Mickley et al. |
| 2007/0232882 A1 | 10/2007 | Glossop et al. |
| 2007/0232896 A1 | 10/2007 | Gilboa et al. |
| 2007/0238984 A1 | 10/2007 | Maschke et al. |
| 2007/0239018 A1 | 10/2007 | Fetzer et al. |
| 2007/0244413 A1 | 10/2007 | Biggins |
| 2007/0247454 A1 | 10/2007 | Rahn et al. |
| 2007/0249911 A1 | 10/2007 | Simon |
| 2007/0255270 A1 | 11/2007 | Carney |
| 2007/0265526 A1 | 11/2007 | Govari et al. |
| 2007/0280974 A1 | 12/2007 | Son et al. |
| 2007/0282196 A1 | 12/2007 | Birk et al. |
| 2007/0282197 A1 | 12/2007 | Bill et al. |
| 2007/0299352 A1 | 12/2007 | Harlev et al. |
| 2007/0299353 A1 | 12/2007 | Harlev et al. |
| 2008/0004652 A1 | 1/2008 | Abboud et al. |
| 2008/0008745 A1 | 1/2008 | Stinchcomb et al. |
| 2008/0009720 A1 | 1/2008 | Schefelker |
| 2008/0015442 A1 | 1/2008 | Watson et al. |
| 2008/0027320 A1 | 1/2008 | Bolorforosh et al. |
| 2008/0033283 A1 | 2/2008 | Dellaca et al. |
| 2008/0033316 A1 | 2/2008 | Kassab et al. |
| 2008/0033350 A1 | 2/2008 | Wilson et al. |
| 2008/0045908 A1 | 2/2008 | Gould et al. |
| 2008/0051626 A1 | 2/2008 | Sato et al. |
| 2008/0077158 A1 | 3/2008 | Haider et al. |
| 2008/0081958 A1 | 4/2008 | Denison et al. |
| 2008/0082136 A1 | 4/2008 | Gaudiani |
| 2008/0097232 A1 | 4/2008 | Rothenberg |
| 2008/0108949 A1 | 5/2008 | Beasley et al. |
| 2008/0114095 A1 | 5/2008 | Peppmoller et al. |
| 2008/0125772 A1 | 5/2008 | Stone et al. |
| 2008/0137927 A1 | 6/2008 | Altmann et al. |
| 2008/0139944 A1 | 6/2008 | Weymer et al. |
| 2008/0146939 A1 | 6/2008 | McMorrow et al. |
| 2008/0146940 A1 | 6/2008 | Jenkins et al. |
| 2008/0146941 A1 | 6/2008 | Dala-Krishna |
| 2008/0146942 A1 | 6/2008 | Dala-Krishna |
| 2008/0154100 A1 | 6/2008 | Thalmeier et al. |
| 2008/0166453 A1 | 7/2008 | Steele et al. |
| 2008/0171934 A1 | 7/2008 | Greenan et al. |
| 2008/0183075 A1 | 7/2008 | Govari et al. |
| 2008/0188830 A1 | 8/2008 | Rosenblatt et al. |
| 2008/0190438 A1 | 8/2008 | Harlev et al. |
| 2008/0195169 A1 | 8/2008 | Pinter et al. |
| 2008/0200754 A1 | 8/2008 | Buchalter |
| 2008/0228082 A1 | 9/2008 | Scheirer et al. |
| 2008/0236598 A1 | 10/2008 | Gobel |
| 2008/0255404 A1 | 10/2008 | Nogawa et al. |
| 2008/0255475 A1 | 10/2008 | Kondrosky et al. |
| 2008/0269581 A1 | 10/2008 | Wood et al. |
| 2008/0269611 A1 | 10/2008 | Pedrizzetti et al. |
| 2008/0275465 A1 | 11/2008 | Paul et al. |
| 2008/0275765 A1 | 11/2008 | Kuchar |
| 2008/0288038 A1 | 11/2008 | Paul et al. |
| 2008/0294041 A1 | 11/2008 | Kassab |
| 2008/0319350 A1 | 12/2008 | Wallace et al. |
| 2009/0005674 A1 | 1/2009 | Saadat et al. |
| 2009/0005675 A1 | 1/2009 | Grunwald et al. |
| 2009/0018497 A1 | 1/2009 | Birchard et al. |
| 2009/0024018 A1 | 1/2009 | Boyden et al. |
| 2009/0030380 A1 | 1/2009 | Binmoeller |
| 2009/0043205 A1 | 2/2009 | Pelissier et al. |
| 2009/0062646 A1 | 3/2009 | Creighton, IV et al. |
| 2009/0062684 A1 | 3/2009 | Gregersen et al. |
| 2009/0080738 A1 | 3/2009 | Zur et al. |
| 2009/0082661 A1 | 3/2009 | Saladin et al. |
| 2009/0084382 A1 | 4/2009 | Jalde et al. |
| 2009/0101577 A1 | 4/2009 | Fulkerson et al. |
| 2009/0118612 A1 | 5/2009 | Grunwald et al. |
| 2009/0118637 A1 | 5/2009 | Kassab et al. |
| 2009/0118706 A1 | 5/2009 | Schweikert et al. |
| 2009/0124901 A1 | 5/2009 | Fink et al. |
| 2009/0143736 A1 | 6/2009 | Mittermeyer et al. |
| 2009/0156926 A1 | 6/2009 | Messerly et al. |
| 2009/0163810 A1 | 6/2009 | Kanade et al. |

(56) References Cited

U.S. PATENT DOCUMENTS

| | | |
|---|---|---|
| 2009/0171217 A1 | 7/2009 | Kim et al. |
| 2009/0177083 A1 | 7/2009 | Matsumura |
| 2009/0177090 A1 | 7/2009 | Grunwald et al. |
| 2009/0203989 A1 | 8/2009 | Burnside et al. |
| 2009/0204113 A1 | 8/2009 | MacAdam et al. |
| 2009/0209872 A1 | 8/2009 | Pop |
| 2009/0209950 A1 | 8/2009 | Starksen |
| 2009/0221908 A1 | 9/2009 | Glossop |
| 2009/0227952 A1 | 9/2009 | Blakstvedt et al. |
| 2009/0234328 A1 | 9/2009 | Cox et al. |
| 2009/0258171 A1 | 10/2009 | Uang |
| 2009/0259124 A1 | 10/2009 | Rothenberg |
| 2009/0262982 A1 | 10/2009 | Markowitz et al. |
| 2009/0270729 A1 | 10/2009 | Corbucci et al. |
| 2009/0270746 A1 | 10/2009 | Min |
| 2009/0275828 A1 | 11/2009 | Shachar et al. |
| 2009/0297441 A1 | 12/2009 | Canham et al. |
| 2010/0004543 A1 | 1/2010 | Ahlund et al. |
| 2010/0004547 A1 | 1/2010 | Scholz et al. |
| 2010/0010355 A1 | 1/2010 | Kassab |
| 2010/0010444 A1 | 1/2010 | Bettuchi |
| 2010/0010612 A1 | 1/2010 | Gelbart et al. |
| 2010/0016726 A1 | 1/2010 | Meier |
| 2010/0036227 A1 | 2/2010 | Cox et al. |
| 2010/0036284 A1 | 2/2010 | Laynes et al. |
| 2010/0041973 A1 | 2/2010 | Vu et al. |
| 2010/0041984 A1 | 2/2010 | Shapland et al. |
| 2010/0049062 A1 | 2/2010 | Ziv |
| 2010/0055153 A1 | 3/2010 | Majmudar |
| 2010/0055184 A1 | 3/2010 | Zeitels et al. |
| 2010/0057157 A1 | 3/2010 | Govari et al. |
| 2010/0060472 A1 | 3/2010 | Kimura et al. |
| 2010/0063401 A1 | 3/2010 | Nishina et al. |
| 2010/0076305 A1 | 3/2010 | Maier-Hein et al. |
| 2010/0076328 A1 | 3/2010 | Matsumura et al. |
| 2010/0081934 A1 | 4/2010 | Soltani et al. |
| 2010/0083719 A1 | 4/2010 | Peppmoller et al. |
| 2010/0094116 A1 | 4/2010 | Silverstein |
| 2010/0106011 A1 | 4/2010 | Byrd et al. |
| 2010/0114573 A1 | 5/2010 | Huang et al. |
| 2010/0117659 A1 | 5/2010 | Osadchy et al. |
| 2010/0130858 A1 | 5/2010 | Arai et al. |
| 2010/0143119 A1 | 6/2010 | Kooijman et al. |
| 2010/0152596 A1 | 6/2010 | Griffiths et al. |
| 2010/0168557 A1 | 7/2010 | Deno et al. |
| 2010/0185097 A1 | 7/2010 | Hall |
| 2010/0198048 A1 | 8/2010 | Togawa |
| 2010/0198346 A1 | 8/2010 | Keogh et al. |
| 2010/0204569 A1 | 8/2010 | Burnside et al. |
| 2010/0204614 A1 | 8/2010 | Lindquist et al. |
| 2010/0210938 A1 | 8/2010 | Verard et al. |
| 2010/0210950 A1 | 8/2010 | Dunbar et al. |
| 2010/0217116 A1 | 8/2010 | Eck et al. |
| 2010/0222664 A1 | 9/2010 | Lemon et al. |
| 2010/0222786 A1 | 9/2010 | Kassab |
| 2010/0234724 A1 | 9/2010 | Jacobsen et al. |
| 2010/0234733 A1 | 9/2010 | Wahlheim |
| 2010/0249598 A1 | 9/2010 | Smith et al. |
| 2010/0258033 A1 | 10/2010 | Yang et al. |
| 2010/0268059 A1 | 10/2010 | Ryu et al. |
| 2010/0273895 A1 | 10/2010 | Stinchcomb et al. |
| 2010/0291521 A1 | 11/2010 | Simon |
| 2010/0298702 A1 | 11/2010 | Rogers et al. |
| 2010/0298704 A1 | 11/2010 | Pelissier et al. |
| 2010/0298705 A1 | 11/2010 | Pelissier et al. |
| 2010/0298712 A1 | 11/2010 | Pelissier et al. |
| 2010/0312086 A9 | 12/2010 | Beatty et al. |
| 2010/0317981 A1 | 12/2010 | Grunwald |
| 2010/0318026 A1 | 12/2010 | Grunwald |
| 2010/0331712 A1 | 12/2010 | Rothenberg |
| 2011/0015527 A1 | 1/2011 | Heasty et al. |
| 2011/0015533 A1 | 1/2011 | Cox et al. |
| 2011/0034823 A1 | 2/2011 | Gelbart et al. |
| 2011/0034940 A1 | 2/2011 | Payner |
| 2011/0040212 A1 | 2/2011 | Dietz et al. |
| 2011/0052694 A1 | 3/2011 | Stinchcomb et al. |
| 2011/0087105 A1 | 4/2011 | Ridley et al. |
| 2011/0087106 A1 | 4/2011 | Ridley et al. |
| 2011/0087107 A1 | 4/2011 | Lindekugel et al. |
| 2011/0106101 A1 | 5/2011 | Tortonese et al. |
| 2011/0112396 A1 | 5/2011 | Shachar et al. |
| 2011/0136242 A1 | 6/2011 | Marx et al. |
| 2011/0137156 A1 | 6/2011 | Razzaque et al. |
| 2011/0196235 A1 | 8/2011 | Dunbar et al. |
| 2011/0196248 A1 | 8/2011 | Grunwald |
| 2011/0196255 A1 | 8/2011 | Kassab |
| 2011/0237935 A1 | 9/2011 | Kalpin et al. |
| 2011/0245659 A1 | 10/2011 | Ma et al. |
| 2011/0282187 A1 | 11/2011 | Harlev et al. |
| 2011/0282188 A1 | 11/2011 | Burnside et al. |
| 2011/0282285 A1 | 11/2011 | Blanchard et al. |
| 2011/0295108 A1 | 12/2011 | Cox et al. |
| 2011/0306867 A1 | 12/2011 | Gopinathan et al. |
| 2011/0313293 A1 | 12/2011 | Lindekugel et al. |
| 2012/0004564 A1 | 1/2012 | Dobak, III |
| 2012/0035460 A1 | 2/2012 | Stangenes et al. |
| 2012/0046562 A1 | 2/2012 | Powers et al. |
| 2012/0059249 A1 | 3/2012 | Verard et al. |
| 2012/0059270 A1 | 3/2012 | Grunwald |
| 2012/0071751 A1 | 3/2012 | Sra et al. |
| 2012/0071759 A1 | 3/2012 | Hagy et al. |
| 2012/0071782 A1 | 3/2012 | Patil et al. |
| 2012/0078342 A1 | 3/2012 | Vollkron et al. |
| 2012/0095319 A1 | 4/2012 | Kondrosky et al. |
| 2012/0108950 A1 | 5/2012 | He et al. |
| 2012/0143029 A1 | 6/2012 | Silverstein et al. |
| 2012/0143078 A1 | 6/2012 | Kassab et al. |
| 2012/0172727 A1 | 7/2012 | Hastings et al. |
| 2012/0220854 A1 | 8/2012 | Messerly et al. |
| 2012/0283582 A1 | 11/2012 | Mahapatra et al. |
| 2012/0296200 A1 | 11/2012 | Shachar et al. |
| 2012/0310052 A1 | 12/2012 | Mahapatra et al. |
| 2012/0310066 A1 | 12/2012 | Shachar et al. |
| 2012/0316440 A1 | 12/2012 | Munrow et al. |
| 2013/0006102 A1 | 1/2013 | Wilkes et al. |
| 2013/0018248 A1 | 1/2013 | Hurezan |
| 2013/0035590 A1 | 2/2013 | Ma et al. |
| 2013/0041269 A1 | 2/2013 | Stahmann et al. |
| 2013/0060116 A1 | 3/2013 | Messerly et al. |
| 2013/0085416 A1 | 4/2013 | Mest |
| 2013/0102890 A1 | 4/2013 | Dib |
| 2013/0123597 A1 | 5/2013 | Rothenberg |
| 2013/0169272 A1 | 7/2013 | Eichler et al. |
| 2013/0217999 A1 | 8/2013 | Burnside et al. |
| 2013/0245434 A1 | 9/2013 | Messerly et al. |
| 2013/0296691 A1 | 11/2013 | Ashe |
| 2013/0303896 A1 | 11/2013 | Kalpin et al. |
| 2013/0317338 A1 | 11/2013 | Silverstein |
| 2013/0324841 A1 | 12/2013 | Kamen et al. |
| 2013/0338503 A1 | 12/2013 | Cohen et al. |
| 2013/0338517 A1 | 12/2013 | Rothenberg |
| 2013/0345555 A1 | 12/2013 | Kanade et al. |
| 2014/0031674 A1 | 1/2014 | Newman et al. |
| 2014/0046261 A1 | 2/2014 | Newman et al. |
| 2014/0094694 A1 | 4/2014 | Moctezuma de la Barrera |
| 2014/0094768 A1 | 4/2014 | Stangenes et al. |
| 2014/0107475 A1 | 4/2014 | Cox et al. |
| 2014/0163356 A2 | 6/2014 | Burnside et al. |
| 2014/0180074 A1 | 6/2014 | Green et al. |
| 2014/0187990 A1 | 7/2014 | Banet et al. |
| 2014/0188133 A1 | 7/2014 | Misener |
| 2014/0228689 A1 | 8/2014 | Ishikawa et al. |
| 2014/0243659 A1 | 8/2014 | Rothenberg |
| 2014/0249505 A1 | 9/2014 | Bukhman |
| 2014/0253270 A1 | 9/2014 | Nicholls et al. |
| 2014/0257080 A1 | 9/2014 | Dunbar et al. |
| 2014/0275957 A1 | 9/2014 | Lupotti |
| 2014/0275990 A1 | 9/2014 | Hagy et al. |
| 2014/0303492 A1 | 10/2014 | Burnside et al. |
| 2014/0343398 A1 | 11/2014 | He et al. |
| 2015/0005621 A1 | 1/2015 | Liu |
| 2015/0018701 A1 | 1/2015 | Cox et al. |
| 2015/0025402 A1 | 1/2015 | Rothenberg |
| 2015/0051489 A1 | 2/2015 | Caluser et al. |

(56) References Cited

U.S. PATENT DOCUMENTS

| | | | |
|---|---|---|---|
| 2015/0080716 A1 | 3/2015 | Powers et al. |
| 2015/0216446 A1 | 8/2015 | Bukhman et al. |
| 2015/0289781 A1 | 10/2015 | Grunwald et al. |
| 2016/0374589 A1 | 12/2016 | Misener et al. |
| 2017/0000367 A1 | 1/2017 | Grunwald |
| 2017/0020561 A1 | 1/2017 | Cox et al. |
| 2017/0079548 A1 | 3/2017 | Silverstein et al. |
| 2017/0079552 A1 | 3/2017 | Grunwald |
| 2017/0079615 A1 | 3/2017 | Burnside et al. |
| 2017/0079681 A1 | 3/2017 | Burnside et al. |
| 2017/0151022 A1 | 6/2017 | Jascob et al. |
| 2017/0231700 A1 | 8/2017 | Cox et al. |
| 2017/0281029 A1 | 10/2017 | Messerly et al. |
| 2018/0070856 A1 | 3/2018 | Grunwald |
| 2018/0103869 A1 | 4/2018 | Bukhman et al. |

FOREIGN PATENT DOCUMENTS

| | | |
|---|---|---|
| AU | 20009592 | 9/2000 |
| AU | 20015250 | 6/2001 |
| AU | 768362 B2 | 12/2003 |
| AU | 2001229024 B2 | 9/2005 |
| AU | 2001283703 B2 | 5/2006 |
| AU | 2006202149 | 6/2006 |
| AU | 2006904933 | 9/2006 |
| AU | 2006283022 B2 | 2/2012 |
| CA | 2420676 | 2/2002 |
| CA | 2619909 C | 1/2014 |
| CN | 2031655 U | 2/1989 |
| CN | 1672649 A | 9/2005 |
| CN | 1913833 A | 2/2007 |
| CN | 101854853 A | 10/2010 |
| CN | 102209490 A | 10/2011 |
| CN | 102802514 A | 11/2012 |
| CN | 102821679 A | 12/2012 |
| CN | 103037761 A | 4/2013 |
| CN | 103037762 A | 4/2013 |
| CN | 103118591 A | 5/2013 |
| CN | 103189009 A | 7/2013 |
| DE | 4319033 C1 | 6/1994 |
| EP | 0359697 | 3/1990 |
| EP | 0362821 | 4/1990 |
| EP | 0399536 A1 | 11/1990 |
| EP | 0823261 A2 | 2/1998 |
| EP | 0928976 A2 | 7/1999 |
| EP | 1025805 A1 | 8/2000 |
| EP | 1311226 A1 | 5/2003 |
| EP | 1504713 A1 | 2/2005 |
| EP | 1717601 A2 | 11/2006 |
| EP | 1932477 A1 | 6/2008 |
| EP | 2313143 A1 | 4/2011 |
| EP | 2440122 A1 | 4/2012 |
| EP | 2464407 A2 | 6/2012 |
| EP | 2482719 A1 | 8/2012 |
| EP | 2575610 A1 | 4/2013 |
| EP | 2575611 A1 | 4/2013 |
| EP | 2603145 A2 | 6/2013 |
| EP | 2605699 A2 | 6/2013 |
| EP | 2618727 A1 | 7/2013 |
| EP | 2632360 A1 | 9/2013 |
| EP | 2219526 B1 | 3/2014 |
| EP | 2712547 A1 | 4/2014 |
| EP | 2992825 B1 | 5/2017 |
| EP | 2265175 B1 | 8/2017 |
| FR | 2545349 | 11/1984 |
| IN | 9721/DELNP/2011 | 1/2013 |
| JP | 01097440 | 4/1989 |
| JP | 03173542 A | 7/1991 |
| JP | 4090741 | 8/1992 |
| JP | 9-503054 | 3/1997 |
| JP | 09-094298 A | 4/1997 |
| JP | 10043310 | 2/1998 |
| JP | 10290839 A | 11/1998 |
| JP | 11128237 A | 5/1999 |
| JP | 2001161683 | 6/2001 |
| JP | 2001-514533 A | 9/2001 |
| JP | 2001-524339 A | 12/2001 |
| JP | 2001340334 | 12/2001 |
| JP | 2002-224069 A | 8/2002 |
| JP | 2002-529133 A | 9/2002 |
| JP | 2002-541947 A | 12/2002 |
| JP | 2003-010138 A | 1/2003 |
| JP | 2003501127 A | 1/2003 |
| JP | 2003061752 A | 3/2003 |
| JP | 2003299654 | 10/2003 |
| JP | 2003334191 | 11/2003 |
| JP | 2002520893 | 2/2004 |
| JP | 2004505748 T | 2/2004 |
| JP | 2004515298 A | 5/2004 |
| JP | 2006508744 A | 3/2006 |
| JP | 2006-338526 A | 12/2006 |
| JP | 2007-000226 A | 1/2007 |
| JP | 2007-068989 A | 3/2007 |
| JP | 2007-105450 A | 4/2007 |
| JP | 2007-313122 A | 12/2007 |
| JP | 5010604 | 6/2012 |
| JP | 2012-529929 | 11/2012 |
| JP | 2013-518676 A | 5/2013 |
| JP | 2013-526959 A | 6/2013 |
| JP | 2013-526961 A | 6/2013 |
| RU | 2009101949 A | 7/2010 |
| WO | 1980002376 A1 | 11/1980 |
| WO | 1991012836 A1 | 9/1991 |
| WO | 1992003090 | 3/1992 |
| WO | 1994003159 A1 | 2/1994 |
| WO | 1994004938 | 3/1994 |
| WO | 1996005768 A1 | 2/1996 |
| WO | 1996007352 A1 | 3/1996 |
| WO | 1996041119 | 12/1996 |
| WO | 1997/22395 A1 | 6/1997 |
| WO | 1997029683 A1 | 8/1997 |
| WO | 1997043989 A1 | 11/1997 |
| WO | 1998025159 A1 | 6/1998 |
| WO | 1998035611 A1 | 8/1998 |
| WO | 1999016495 A1 | 4/1999 |
| WO | 1999027837 A2 | 6/1999 |
| WO | 1999049407 A1 | 9/1999 |
| WO | 2000019906 | 4/2000 |
| WO | 2000027281 A1 | 5/2000 |
| WO | 2000040155 | 7/2000 |
| WO | 2000063658 A2 | 10/2000 |
| WO | 2000074775 A1 | 12/2000 |
| WO | 2001013792 A1 | 3/2001 |
| WO | 2001039683 A1 | 6/2001 |
| WO | 2001076479 A1 | 10/2001 |
| WO | 02/07794 A2 | 1/2002 |
| WO | 2002015973 A1 | 2/2002 |
| WO | 2002019905 A1 | 3/2002 |
| WO | 2002025277 A1 | 3/2002 |
| WO | 2002085442 A1 | 10/2002 |
| WO | 2003061752 | 7/2003 |
| WO | 2003077759 A1 | 9/2003 |
| WO | 2003091495 A1 | 11/2003 |
| WO | 2004002303 A1 | 1/2004 |
| WO | 2004049970 A2 | 6/2004 |
| WO | 2005033524 A1 | 4/2005 |
| WO | 2005033574 A1 | 4/2005 |
| WO | 2005/089851 A1 | 9/2005 |
| WO | 2005117690 A1 | 12/2005 |
| WO | 2005117733 A2 | 12/2005 |
| WO | 2006074509 A1 | 7/2006 |
| WO | 2006074510 A1 | 7/2006 |
| WO | 2006078677 A2 | 7/2006 |
| WO | 2006103661 A2 | 10/2006 |
| WO | 2006111056 A1 | 10/2006 |
| WO | 2007002541 A2 | 1/2007 |
| WO | 2007005976 A1 | 1/2007 |
| WO | 2007014447 A1 | 2/2007 |
| WO | 2007034196 A2 | 3/2007 |
| WO | 2007067324 A1 | 6/2007 |
| WO | 2007069168 A2 | 6/2007 |
| WO | 2007109123 A2 | 9/2007 |
| WO | 2007126536 A2 | 11/2007 |
| WO | 2007144894 A1 | 12/2007 |

(56) References Cited

FOREIGN PATENT DOCUMENTS

| | | |
|---|---|---|
| WO | 2008005480 A1 | 1/2008 |
| WO | 2008024596 A2 | 2/2008 |
| WO | 2008028253 | 3/2008 |
| WO | 2008083111 | 7/2008 |
| WO | 2008097767 A2 | 8/2008 |
| WO | 2008118992 A1 | 10/2008 |
| WO | 2008126074 A2 | 10/2008 |
| WO | 2008129326 A1 | 10/2008 |
| WO | 2008131017 A2 | 10/2008 |
| WO | 2008136008 A2 | 11/2008 |
| WO | 2009000439 A1 | 12/2008 |
| WO | 2009002514 A2 | 12/2008 |
| WO | 2009003138 A1 | 12/2008 |
| WO | 2009009064 A1 | 1/2009 |
| WO | 2009057774 A1 | 5/2009 |
| WO | 2009063166 A1 | 5/2009 |
| WO | 2009067654 A1 | 5/2009 |
| WO | 2009070616 A2 | 6/2009 |
| WO | 2009100158 A1 | 8/2009 |
| WO | 2009123819 A2 | 10/2009 |
| WO | 2009126340 A1 | 10/2009 |
| WO | 2009129475 A1 | 10/2009 |
| WO | 2009129477 A1 | 10/2009 |
| WO | 2009134605 A2 | 11/2009 |
| WO | 2009137262 A2 | 11/2009 |
| WO | 2010002313 A1 | 1/2010 |
| WO | 2010018500 A1 | 2/2010 |
| WO | 2010022370 A1 | 2/2010 |
| WO | 2010027349 A1 | 3/2010 |
| WO | 2010027471 A2 | 3/2010 |
| WO | 2010029906 A1 | 3/2010 |
| WO | 2010030820 A1 | 3/2010 |
| WO | 2010132857 A1 | 11/2010 |
| WO | 2010132985 A1 | 11/2010 |
| WO | 2010143196 A1 | 12/2010 |
| WO | 2010144922 A1 | 12/2010 |
| WO | 2011019760 A2 | 2/2011 |
| WO | 2011041450 A1 | 4/2011 |
| WO | 2011044421 A1 | 4/2011 |
| WO | 2011057289 A2 | 5/2011 |
| WO | 2011064209 A1 | 6/2011 |
| WO | 2011084593 A2 | 7/2011 |
| WO | 2011097312 A1 | 8/2011 |
| WO | 2011128052 A2 | 10/2011 |
| WO | 2011150358 A1 | 12/2011 |
| WO | 2011150376 A1 | 12/2011 |
| WO | 2012021542 A2 | 2/2012 |
| WO | 2012024577 A2 | 2/2012 |
| WO | 2012039866 A1 | 3/2012 |
| WO | 2012040487 A1 | 3/2012 |
| WO | 2012058461 A1 | 5/2012 |
| WO | 2012083245 A1 | 6/2012 |
| WO | 2012088535 A1 | 6/2012 |
| WO | 2012110955 A1 | 8/2012 |
| WO | 2012173697 A1 | 12/2012 |
| WO | 2013006713 A2 | 1/2013 |
| WO | 2013006817 A1 | 1/2013 |
| WO | 2013034175 A1 | 3/2013 |
| WO | 2014052894 A2 | 4/2014 |
| WO | 2014062728 A1 | 4/2014 |
| WO | 2014138652 A1 | 9/2014 |
| WO | 2014138918 A1 | 9/2014 |
| WO | 2015/120256 A2 | 8/2015 |
| WO | 2016/210325 A1 | 12/2016 |

OTHER PUBLICATIONS

PCT/US2011/052793 filed Sep. 22, 2011 International Search Report dated Jan. 6, 2012.
PCT/US2011/052793 filed Sep. 22, 2011 Written Opinion dated Jan. 6, 2012.
PCT/US2011/058138 filed Oct. 27, 2011 International Preliminary Report on Patentability dated May 10, 2013.
PCT/US2011/058138 filed Oct. 27, 2011 International Search Report dated Feb. 7, 2012.
PCT/US2011/058138 filed Oct. 27, 2011 Written Opinion dated Feb. 7, 2012.
PCT/US2011/067268 filed Dec. 23, 2011 International Preliminary Report on Patentability dated Jul. 4, 2013.
PCT/US2011/067268 filed Dec. 23, 2011 International Search Report and Written Opinion dated Apr. 27, 2012.
PCT/US2012/045814 filed Jul. 6, 2012 International Search Report and Written Opinion dated Oct. 1, 2012.
PCT/US2013/065121 filed Oct. 15, 2013 International Search Report and Written Opinion dated Jan. 16, 2014.
PCT/US2014/022019 filed Mar. 7, 2014 International Search Report and Written Opinion dated Jun. 11, 2014.
Pennington, C.R., Right Atrial Thrombus: a Complication of Total Parenteral Nutrition, British Medical Journal, pp. 446-447, vol. 295, Aug. 15, 1987.
Petersen, J et al, Silicone Venous Access Devices Positioned with their Tip High in the Superior Vena Cava are More Likely to Malfunction, Am J Surg, pp. 38-41, vol. 178 No. 1, Jul. 1999.
Pittiruti, et al, Intracavitary EKG Monitoring: A reliable method for controlling tip position during and after PICC Insertion presentation in Catholic University, Rome, Italy in 2008.
Pittiruti, et al. "The EKG Method for Positioning the Tip of PICCs: Results from Two Preliminary Studies." JAVA, vol. 13, No. 4, pp. 179-185, 2008.
Polos, PG et al, Tips for Monitoring the Position of a Central Venous Catheter—How Placement can go awry—even when the anatomy is normal, J Crit Illn, pp. 660-674, vol. 8 No. 6, Jun. 1993 (Abstract only).
Pop, Gheorghe A. et al., Catheter-based impedance measurements in the right atrium for continuously monitoring hematocrit and estimating blood viscosity changes; an in vivo feasibility study in swine, Biosensors and Bioelectronics 19 (2004) 1685-1693.
Popp, M. B. et al., Accuracy of implanted port placement with the use of the electromagnetic CathTrack® catheter locator system, The Journal of Vascular Access 2005; 6: 9-12.
Randolph AG et al, Ultrasound guidance for placement of central venous catheters: a meta-analysis of the literature, Critcal Care Medicine, pp. 2053-2058, vol. 24, Dec. 1996.
Reece, A et al, Posititioning Long Lines: Contrast Versus Plain Radiography, Arch Dis Child Fetal Neonatal Ed, pp. 129-130, vol. 84 No. 2, Mar. 2001.
Reynolds, N et al, Assessment of Distal Tip Position of Long Term Central Venous Feeding Catheters using Transesophageal Echocardiology, JPEN J Parenter Enteral Nutr, pp. 39-41, vol. 25 No. 1, Jan.-Feb. 2001.
RU 2011150917 filed Dec. 15, 2011 First Office Action dated Apr. 24, 2014.
Ruschulte, Heiner et al, Prevention of Central Venous Catheter related infections with chlorhex idine gluconate impregnated wound dressings: A randomized controlled trial, presented as an abstract at the Annual meeting of the European Society of Anaesthesiologists (ESA) in Madrid, Spain in Jun. 2006, 12 pages, Annals of Hematology, Jul. 14, 2008.
Rutherford, J. S. et al., Depth of Central Venous Catheterization: An Audit of Practice in a Cardiac Surgical Unit, Anaesth Intens Care 1994; 22: 267-271.
Sacolick, et al. "Electromagnetically Tracked Placement of a Peripherally Inserted Central Catheter." SPIE Medical Imaging, 2004 Proceedings.
Salem, et al. "A New Peripherally Implanted Subcutaneous Permanent Central Venous Access Device for Patients Requiring Chemotherapy." Journal of Clinical Oncology, vol. 11, No. 11, pp. 2181-2185, Nov. 1993.
Savary, D et al, Intra-atrial Monitoring to Add Insertion of a Central Venous Line in Pre-Hospital Emergency Care Journal Europeen des Urgences, pp. 75-78, vol. 17 No. 2, 2004.
Schafer et al. "Incorrect placement of a vena cava catheter and its prevention by intra-atrial ECG." Anaesthesist. Jan. 1988;37(1):49-51.

(56) References Cited

OTHER PUBLICATIONS

Schummer, et al. "Central Venous Catheters—The inability of 'intra-atrial ECG' to prove adequate positioning." British Journal of Anaesthesia, vol. 93, No. 2, pp. 193-198, 2004.
Schummer, W et al, ECG-guided Central Venous Catheter Positioning: Does it detect the Pericardial Reflection rather than the Right Atrium?, Eur J Anaesthesiol, pp. 600-605, vol. 21 No. 8, Aug. 2004 (Abstract only).
Schummer, W et al, Intra-Atrial ECG is not a Reliable Method for Positioning Left Internal Jugular Vein Catheters, Br J Anaesth, pp. 481-486, vol. 91 No. 4, Oct. 2003.
Schummer, W, Central Venous Catheter—the Inability of "Intra-Atrial ECG" to prove Adequate Positioning, Br J Anaesth, pp. 193-198, vol. 93 No. 2, Aug. 2004.
Schuster, M. et al., The carina as a landmark in central venous catheter placement, British Journal of Anaesthesia 85 (2): 192-4 (2000).
Siela, Debra, Using Chest Radiography in the Intensive Care Unit, Crit Care Nurse Aug. 1, 2002 vol. 22 No. 4, pp. 18-27.
Simon, et al., "Central Venous Catheter Placement in Children: Evaluation of Electrocardiography Using J-Wire." Paediatric Anaesthesia vol. 9, pp. 501-504, 1999.
Smith, Brigham, et al., Intravenous electrocardiographic guidance for placement of peripherally inserted central catheters, Journal of Electrocardiology 43 (2010) 274-278.
Stark, DD et al, Radiographic Assessment of Venous Catheter Position in Children: Value of the Lateral View, Pediatric Radiology, pp. 76-80, vol. 14 No. 2, 1984.
Starkhammar et al. "Cath-Finder Catheter Tracking System: A New Device for Positioning of Central Venous Catheters. Early Experience from Implantation of Brachial portal Systems." Acta Anaesthesiol Scandinavia, vol. 34, No. 4 pp. 296-300, May 1990.
Starkhammer, H et al, Central Venous Catheter Placement using Electromagnetic Position Sensing: A Clinical Evaluation, Biomed. Instrum Technol, vol. 30 No. 2, pp. 164-170; Mar.-Apr. 1996.
Starr, David S et al, EKG Guided Placement of Subclavian CVP Catheters Using J-Wire, pp. 673-676, Ann. Surg, Dec. 1986.
Stas, M et al, Peroperative Intravasal Electrographic Control of Catheter Tip Position in Access Ports Placed by Venous Cut-Down Technique, EJSO, pp. 316-320, vol. 27, 2001.
Stereotaxis Magetic Navigation System with Navigant™ User Interface, 2005 Brochure.
Stereotaxis, Expanding the Possibilites of Interventional Medicine: Remote Navigation and Automation, pp. 1-8, Apr. 2011.
Tepa® Health Innovation PC based ECG System Introduction and Technical Specifications, EKG Master USB, 2 pages, Nov. 2003.
The FloWire Doppler Guide Wire located <http://www.volcanocorp.com/products/flowire-doppler-guide-wire.php>, 2011.
Traxal Technologies, Tracking Technology website overview: www.traxal.com/rd/rd_classroom_trackingtechnology.htm, last accessed Dec. 1, 2006.
UAB Health Systems, Arrhythmias, retrieved from http://www.health,uab.edu/14564/ on Nov. 15, 2007, 12 pages.
U.S. Appl. No. 11/466,602, filed Aug. 23, 2006 Advisory Action dated Jun. 22, 2009.
U.S. Appl. No. 11/466,602, filed Aug. 23, 2006 Appeal Board Decision dated Sep. 17, 2012.
U.S. Appl. No. 11/466,602 filed Aug. 23, 2006 Final Office Action dated Apr. 8, 2010.
U.S. Appl. No. 11/466,602, filed Aug. 23, 2006 Final Office Action dated Jan. 30, 2014.
GB Application 0800474.9 filed Aug. 24, 2006 Office Action dated Mar. 17, 2010.
Gebauer, B et al, Ultrasound and Fluoroscopy-guided Implantation of Peripherally Inserted Central Venous Catheters (PICCs), ROFO, pp. 386-391, vol. 176 No. 3, Mar. 2004 (Abstract only).
Gebhard, et al., "The accuracy of Electrocardiogram-Controlled Central Line Placement." The International Anesthesia Research Society, vol. 104, No. 1 Jan. 2007.
Gjendemsjo, Anders, et al., Energy and Power, The Connexions Project, Version 1.2, Feb. 20, 2004.
Gladwin, MT et al, Cannulation of the Internal Jugular Vein: is postpocedural chest radiography always necessary?, Crit Care Med, 33 pages, Oct. 2000.
Gonzales, et al. "Peripherally Inserted Central Catheter Placement in Swine Using Magnet Detection." Journal of Intravenous Nursing, vol. 22, No. 3, May/Jun. 1999.
Greenall, M.J. et al, Cardiac Tamponade and Central Venous Catheters, British Medical Journal, pp. 595-597, Jun. 14, 1975.
Guillory, "Basic Principles of Technologies for Catheter Localization." C.R. Bard internal paper, Oct. 20, 2004.
Guth, AA, Routine Chest X-rays after Insertion of Implantable Long-Term Venous Catheters: Necessary or Not?, Am Surg, pp. 26-29, vol. 67 No. 1, Jan. 2001 (Abstract only).
Hill, Bradley et al, Abstract of article discussing Vasallova VPS as guide for placement of PICCs. 2009.
Hill, Bradley, Identifying the Caval-Atrial Junction Using Smart-Catheter Technology presentation, 22nd Annual Scientific Meeting of the AVA in Savannah, Georgia, Sep. 13, 2008.
Hoffman, Thomas et al, Simultaneous Measurement of Pulmonary Venous Flow by Intravascular Catheter Doppler Velocimetry and Transesophageal Doppler Echocardiography: Relation to Left Atrial Pressure and Left Atrial and Left Ventricular Function, pp. 239-249, J Am Coll Cardiol, Jul. 1995.
Hoffmann, et al. "New Procedure in Transesophageal Echocardiography: Multiplane Transesophageal Echocardiography and Transesophageal Stress Echocardiography." Herz, vol. 18, No. 5, pp. 269-277, Oct. 1993.
Iacopino, Domenico Gerardo et al, Intraoperative Microvascular Doppler Monitoring of Blood Flow within a Spinal Dural Arteriovenous Fistula: A Precious Surgical Tool, vol. 10, 5 pages, Neurosurg. Focus, Feb. 2001.
Jeon, Yunseok et al., "Transesophageal Echocardiographic Evaluation of ECG-guided Central Venous Catheter Placement," Canadian Journal of Anesthesia, vol. 53, No. 10, Oct. 1, 2006, pp. 978-983.
Joosting, Jean-Pierre, "Dual-interface RFID-compatible EEPROM enables remote access to electronic device parameters," EE Times, Mar. 8, 2010.
JP 2008-528151 filed Aug. 24, 2006 Notice of Grant dated May 6, 2012.
JP 2010-504220 filed Sep. 3, 2009 Final Office Action dated Apr. 18, 2013.
JP 2010-504220 filed Sep. 3, 2009 Office Action dated May 21, 2012.
JP 2010-535117 filed May 26, 2011 First Office Action dated Aug. 5, 2013.
JP 2012-515222 filed Dec. 9, 2011 Office Action dated Mar. 24, 2014.
Kim, Ko et al, Positioning Internal Jugular Venous Catheters using the Right Third Intercostal Space in Children, Acta Anaesthesiol Scand, pp. 1284-1286, vol. 47 No. 10, Nov. 2003.
Kjelstrup T et al, Positioning of Central Venous Catheters using ECG, Tidssk Nor Laegeforen, pp. 599-601, vol. 111 No. 5, Feb. 1999 (Abstract only).
Kofler, Julia, et al., Epinephrine application via an endotracheal airway and via the Combitube in esophageal position, Critical Care Medicine: May 2000, vol. 28: Issue 5, pp. 1445-1449.
Konings, MK, et al., Development of an intravascular impedance catheter for detection of fatty lesions in arteries, IEEE Trans Med Imaging Aug. 1997; 16(4):439-46.
Kowalski, CM et al, Migration of Central Venous Catheters: Implications for Initial Catheter Tip Positioning, J Vasc Intery Radiol, pp. 443-447, vol. 8 No. 3, May-Jun. 1997.
Leowenthal, MR et al, The Peripherally Inserted Central Catheter (PICC): A Prospective Study of its Natural History after Fossa Insertion, Anaesth Intensive Care, pp. 21-24; vol. 30 No. 1, Feb. 2002.
Lepage Ronan et al. ECG Segmentation and P-wave Feature Extraction: Application to Patients Prone to Atrial Fibrillation, IEEE/EMBS Proceedings, 23rd Annual Conference, Istanbul, Turkey, Oct. 25-28, 2001.

(56) References Cited

OTHER PUBLICATIONS

Liu, Ji-Bin et al, Catheter-Based Intraluminal Sonography, J Ultrasound Med, pp. 145-160, vol. 23, 2004.
Lucey, B et al, Routine Chest Radiographs after Central Line Insertion: Mandatory Postprocedural Evaluation or Unnecessary Waste of Resources?, Cardiovasc Intervent Radiol, pp. 381-384, vol. 22 No. 5, Sep.-Oct. 1999.
Lum, Phillip, A New Formula-Based Measurement Guide for Optimal Positioning of Central Venous Catheters, JAVA, vol. 9, No. 2, pp. 80-85, 2004.
Lynch, RE et al, A Procedure for Placing Pediatric Femoral Venous Catheter Tips near the Right Atrium, Pediatr Emerg Care, pp. 130-132, vol. 18 No. 2, Apr. 2002.
Madan, et al. "Right Atrial Electrocardiography: A Technique for the Placement of Central Venous Catheters for Chemotherapy or Intravenous Nutrition." British Journal of Surgery, vol. B1, pp. 1604-1605, 1994.
Madias, John E, Intracardiac (Superior Vena Cava/Right Atrial) ECGs using Saline Solution as the Conductive Medium for the Proper Positioning of the Shiley Hemodialysis Catheter: Is it Not Time to Forego the Postinsertion Chest Radiograph?, pp. 2363-2367, Chest, 2003.
Markovich, Mary B., Central Venous Catheter Tip Placement: Determination of Posterior Malposition-A Case Study, JAVA, vol. 11, No. 2, pp. 85-89, 2006.
Martin, Roy W, An Ultrasoundic Catheter for Intravascular Measurement of Blood Flow: Technical Details, IEEE Transactions on Sonics and Ultrasonics, vol. SU-27, No. 6, pp. 277-286, Nov. 1980.
McDonnall, "Intra-Atrial Electrocardiography (ECG) for Catheter Placement." Literature review prepared for Bard Access Systems, Oct. 2007.
McGee et al., "Accurate Placement of Central Venous Catheters: A Prospective, Randomize, Multicenter Trail." Critical Care Medicine, vol. 21 No. 8, Aug. 1993.
MedGraphics, CardioPerfect® Resting/Stress ECG System, 3 pages, 2001.
Michenfelder, John et al, Air Embolism During Neurosurgery—An Evaluation of Right-Atrial Catheters for Diagnosis and Treatment, JAMA, pp. 1353-1358, vol. 208, No. 8, May 26, 1969.
Michenfelder, John et al, Air Embolism During Neurosurgery. A New Method of Treatment, Anesthesia and Analgesia. Current Researches, pp. 390-395, vol. 45, No. 4, Jul.-Aug. 1966.
Microbird™ Miniaturized DC Magnetic Sensors for Intra-body Navigation and Localization, Specifications, 2005.
Micron Ix CathRite™ Cardiac Access Device Brochure. Jun. 2004.
Micronix Pty Ltd "CathRite" Guiding Styled Core Manufacturing, Jun. 15, 2006.
Murthy, Vrudhula et al, Analysis of Power Spectral Densities of Electrocardiograms, Mathematical Biosciences, pp. 41-51, vol. 12 No. 1-2, Oct. 1971.
Nadroo, AM et al, Changes in Upper Extremity Position Cause Migration of Peripherally Inserted Central Catheters in Neonates, Pediatrics, pp. 131-136, vol. 110, Jul. 2002.
Nakatani, K et al, Accurate Placement of Central Venous Catheters—ECG-guided method vs Patient Height Method, MASUI, pp. 34-38, vol. 51 No. 1, Jan. 2002.
Nazarian, GK et al, Changes in Tunneled Catheter Tip Position when a patient is Upright, J Vasc Interv Radiol, pp. 437-441, vol. 8 No. 3, May-Jun. 1997.
Neurometer® CPT, Clinical Applications. Neurotron, Inc. website: www.neurotron.com/CLINAPS.html, last accessed Oct. 23, 2006.
Neurometer® CPT, Frequently Asked Questions. Neurotron, Inc. website: www.neurotron.com/CPTFAQ/html, last accessed Oct. 23, 2006.
U.S. Appl. No. 11/466,602, filed Aug. 23, 2006 Final Office Action dated Oct. 28, 2013.
U.S. Appl. No. 11/466,602, filed Aug. 23, 2006 Non-Final Office Action dated Mar. 28, 2013.
U.S. Appl. No. 11/466,602, filed Aug. 23, 2006 Non-Final Office Action dated Sep. 25, 2009.
U.S. Appl. No. 11/466,602, filed Aug. 23, 2006 Notice of Allowance dated Dec. 3, 2012.
U.S. Appl. No. 11/466,602, filed Aug. 23, 2006 Notice of Allowance dated Mar. 14, 2014.
U.S. Appl. No. 11/552,094, filed Oct. 23, 2006 Notice of Allowability dated Apr. 2, 2010.
U.S. Appl. No. 11/552,094 filed Oct. 23, 2006 Non-Final Office Action dated Apr. 27, 2009.
U.S. Appl. No. 11/552,094, filed Oct. 23, 2006 Notice of Allowance dated May 20, 2010.
U.S. Appl. No. 12/104,253, filed Apr. 16, 2008 Final Office Action dated Jul. 27, 2011.
U.S. Appl. No. 12/104,253, filed Apr. 16, 2008 Non-Final Office Action dated Nov. 29, 2010.
U.S. Appl. No. 12/323,273, filed Nov. 25, 2008 Non-Final Office Action dated Jun. 8, 2012.
U.S. Appl. No. 12/369,625, filed Feb. 11, 2009 Final Office Action dated Feb. 23, 2012.
U.S. Appl. No. 12/369,625, filed Feb. 11, 2009 Notice of Allowance dated Oct. 5, 2012.
U.S. Appl. No. 12/369,625, filed Feb. 11, 2009 Notice of Panel Decision dated Aug. 1, 2012.
U.S. Appl. No. 12/369,625, filed Feb. 11, 2009 Non-Final Office Action dated Jul. 20, 2011.
U.S. Appl. No. 12/426,175, filed Apr. 17, 2009 Advisory Action dated Nov. 26, 2013.
U.S. Appl. No. 12/426,175, filed Apr. 17, 2009 Final Office Action dated Aug. 2, 2013.
U.S. Appl. No. 12/426,175, filed Apr. 17, 2009 Final Office Action dated Jan. 31, 2014.
U.S. Appl. No. 12/426,175, filed Apr. 17, 2009 Non-Final Office Action dated Dec. 3, 2012.
U.S. Appl. No. 12/427,244, filed Apr. 21, 2009 Non-Final Office Action dated Jan. 19, 2012.
U.S. Appl. No. 12/545,762, filed Aug. 21, 2009 Final Office Action dated Mar. 7, 2013.
U.S. Appl. No. 12/545,762, filed Aug. 21, 2009 Non-Final Office Action dated Aug. 1, 2012.
U.S. Appl. No. 12/545,762, filed Aug. 21, 2009 Non-Final Office Action dated Dec. 13, 2013.
U.S. Appl. No. 12/557,401, filed Sep. 10, 2009 Non-Final Office Action dated Apr. 24, 2012.
U.S. Appl. No. 12/557,401, filed Sep. 10, 2009 Non-Final Office Action dated Jan. 6, 2014.
U.S. Appl. No. 12/575,456, filed Oct. 7, 2009 Non-Final Office Action dated Oct. 5, 2012.
U.S. Appl. No. 12/715,556, filed Mar. 2, 2010 Final Office Action dated Oct. 2, 2013.
U.S. Appl. No. 12/715,556, filed Mar. 2, 2010 Non-Final Office Action dated Sep. 13, 2012.
U.S. Appl. No. 12/815,331, filed Jun. 14, 2010 Advisory Action dated Oct. 4, 2013.
U.S. Appl. No. 12/815,331, filed Jun. 14, 2010 Final Office Action dated Jul. 26, 2013.
U.S. Appl. No. 12/815,331, filed Jun. 14, 2010 Non-Final Office Action dated Jan. 22, 2013.
U.S. Appl. No. 12/854,083, filed Aug. 10, 2010 Final Office Action dated Aug. 15, 2013.
U.S. Appl. No. 12/854,083, filed Aug. 10, 2010 Non-Final Office Action dated Jan. 29, 2013.
U.S. Appl. No. 12/854,083, filed Aug. 10, 2010 Non-Final Office Action dated Jan. 29, 2014.
U.S. Appl. No. 12/878,915, filed Sep. 9, 2010 Final Office Action dated Sep. 26, 2012.
U.S. Appl. No. 12/878,915, filed Sep. 9, 2010 Non-Final Office Action dated Mar. 15, 2012.
U.S. Appl. No. 12/878,915, filed Sep. 9, 2010 Notice of Allowance dated Jan. 8, 2013.
U.S. Appl. No. 12/893,916, filed Sep. 29, 2010 Non-Final Office Action dated Dec. 24, 2013.
U.S. Appl. No. 12/900,750, filed Oct. 8, 2010 Non-Final Office Action dated Jun. 3, 2013.

(56) References Cited

OTHER PUBLICATIONS

U.S. Appl. No. 13/019,939, filed Feb. 2, 2011 Final Office Action dated Apr. 2, 2014.
U.S. Appl. No. 13/019,939, filed Feb. 2, 2011 Non-Final Office Action dated Oct. 11, 2013.
U.S. Appl. No. 13/118,033, filed May 27, 2011 Non-Final Office Action dated Aug. 1, 2013.
U.S. Appl. No. 13/118,033, filed May 27, 2011 Non-Final Office Action dated May 22, 2014.
U.S. Appl. No. 13/118,138, filed May 27, 2011 Final Office Action dated Apr. 3, 2013.
U.S. Appl. No. 13/118,138, filed May 27, 2011 Non-Final Office Action dated Oct. 3, 2012.
U.S. Appl. No. 13/213,622, filed Aug. 19, 2011 Final Office Action dated Feb. 19, 2013.
U.S. Appl. No. 13/213,622, filed Aug. 19, 2011 Non-Final Office Action dated Jul. 31, 2012.
U.S. Appl. No. 13/213,622, filed Aug. 19, 2011 Non-Final Office Action dated May 22, 2014.
U.S. Appl. No. 13/283,395, filed Oct. 27, 2011 Non-Final Office Action dated Apr. 23, 2013.
U.S. Appl. No. 13/336,919, filed Dec. 23, 2011 Advisory Action dated May 23, 2013.
"Ascension to Launch New 3D Guidance™ Tracker at TCT 2006." Press Releases from Ascension website: www.ascension-tech.com/news/press_101106.php, last accessed Dec. 1, 2006.
Acuson—The Value of Vision, AcuNav Diagnostic Ultrasound Catheter, 2000.
Advertising flyer for GAVECELT—The Italian Group for Long Term Venous Access Devices, for program on International Meeting on PICC's, Midline Catheters and Long Term Venous Access Devices in Catholic University, Rome, Italy on Dec. 3, 4, 5, 2008.
Alexander, GD et al, The Role of Nitrous Oxide in Postoperative Nausea and Vomiting, Collection of Abstracts Presented at the International Anesthesia Research Society by various speakers, 58th Congress, Mar. 12-14, 1984, Anesthesia and Analgesia, pp. 175-284, vol. 63, 1984.
Allan, P.L. et al, Role of Ultrsound in the Assessment of Chronic Venous Insufficiency, Ultrasound Quarterly, vol. 17, No. 1, pp. 3-10, 2001.
Andropoulos, et al. "A Controlled Study of the Transesophageal Echocardiography to Guide Central Venous Catheter Placement in Congetital Heart Surgery Patients." The International Anesthesia Research Society, vol. 89, pp. 65-70, 1999.
Anonymous author, Correct Catheter Placement with a low-impact, reliable and economical method, <http://www.cvc-partner.com/index.cfm?103A955CC6844BF58ACFE3C9C1471959>, last accessed Dec. 22, 2011.
Arai, J et al, Detection of Peripherally Inserted Central Catheter Occlusion by in-line Pressure Monitoring, Paediatr Anaesth, pp. 621-624, vol. 12 No. 7, Sep. 2002.
Arrow International, Inc., The Arrow-Johans RAECG Adapter-Making Proper Central Venous Catheter Placement More Reliable (Modle No. EG-04900), Technical Report 1987, USA.
Aslamy, et al. "MRI of Central Venous Anatomy: Implications for Central Venous Catheter Insertion." American College of Chest Physicians, Jun. 8, 2009.
AU 2006283022 filed Aug. 24, 2006 Office Action dated Dec. 22, 2010.
AU 2008329807 exam requested Aug. 13, 2012 Examination Report No. 1 dated Feb. 15, 2013.
AU 2008329807 exam requested Aug. 13, 2012 Notice of Acceptance dated Feb. 14, 2014.
AU 2010300677 filed Mar. 12, 2012 First Examination Report dated Mar. 9, 2014.
AU 2011289513 filed Jan. 21, 2013 Examiner's Report dated Jul. 5, 2013.
AU 2012202293 filed Apr. 19, 2012 Examination Report No. 1 dated Apr. 24, 2013.
AU 2013201648 filed Mar. 19, 2013 Examiner's Report dated Mar. 5, 2014.
AU 2013201648 filed Mar. 19, 2013 Examiner's Report dated Oct. 14, 2013.
AU 2013202824 filed Apr. 6, 2013 First Examiner's Report dated Mar. 10, 2014.
AU 2013204243 filed Apr. 12, 2013 Examiner's Report dated Jun. 5, 2013.
AURORA® System Technical Specifications, Oct. 2003.
B. Braun Website, "The Optimal Position of the Central Venous Catheter." http://www.cvcpartner.com/index.cfm18F1BDEA1310466194960A39F4E90968 (2009).
B. Braun, Certofix Central Venous Catheter for Placement Using the Seldinger Technique with Simultaneous ECG Lead Option, Feb. 2010.
Bailey, SH et al, Is Immediate Chest Radiograph Necessary after Central Venous Catheter Placement in a Surgical Intensive Care Unit?, Am J Surg, pp. 517-522, vol. 180 No. 6, Dec. 2000.
Bankier, Alexander A., Azygos Arch Cannulation by Central Venous Catheters: Radiographic Detection of Malposition and Subsequent Complications, Journal of Thoracic Imaging 12:64-69 (1997).
Barber, JM et al, A Nurse led Peripherally Inserted Central Catheter Line Insertion Service is Effective with Radiological Support, Clin Radiol, pp. 352-354, vol. 57 No. 5, May 2002.
Bard Access Systems, Sherlock Tip Location System, 5 pages, 2006.
Bard Access Systems, Site Rite Vascular Acess Ultrasound System, 4 pages, 2005.
Benchimol, Alberto at al, Right Atrium and Superior Vena Cava Flow Velocity in Man Measured with the Doppler-Catheter Flowmeter-Telemetry System, The Amer Journal of Medicine, pp. 303-309, vol. 48, Mar. 1970.
Benzadon, M. N. et al: "Comparison of the Amplitude of the P-Wave from Intracardiac Electrocardiogram Obtained by Means of a Central Venous Catheter Filled With Saline Solution to That Obtained Via Esophageal Electrocardiogram", American Journal of Cardiology, Canners Publishing Co., Newton, MA, US, vol. 98, No. 7, Oct. 1, 2006 (Oct. 1, 2006), pp. 978-981.
BioAdvance Lumen Vu, Greenhouse Fund Feb. 2004 Recipient, www.bioadvance.com <http://www.bioadvance.com>, 2005.
Borgobello, Bridget, App allows users to view electrocardiograms on smartphones dated Oct. 15, 2010; printed from http://www.gizmag.com/app-to-view-electrocardiograms-on-smartphones/16664/ on Feb. 4, 2011.
Buehrle, Douglas, PICC Placement in Humans using Electromagnetic Detection, <http://www.corpakmedsystems.com/supplement_material/supplementpages/navigator/navarticle.html>, 2008.
C.R. R Bard, CathTrack™ Catheter Location System at www.bardaccess.com <http://www.bardaccess.com>, last accessed Apr. 28, 2011.
C.R. Bard, Inc., Bard Electrophysiology Product Catalogue, Bard Catheters, pp. 74-75 (2002), USA.
CA 2,619,909 filed Aug. 24, 2006 Examiner's Report dated Oct. 26, 2012.
Cadman, A et al, To Clot or Not to Clot? That is the question in Central Venous Catheters, Clinical Radiology, pp. 349-355, vol. 59 No. 4, Apr. 2004.
Calvert, N. et al, The Effectiveness and Cost-effectiveness of Ultrasound Locating Devices for Central Venous Access: A Systematic Review and Economic Evaluation, Health Technology Assessment, vol. 7, No. 12, 2003.
Cardella, John F. et al., Interventinal Radiologic Placement of Peripherally Inserted Central Catheters, Journal of Vascular and Interventional Radiology 1993; 4:653-660.
Carlon, R et al, Secondary Migration of a Central Venous Catheter—A Case Report, Minerva Anestesiol, pp. 927-931, vol. 69 No. 12, Dec. 2003.
Caruso, LJ et al, A Better Landmark for Positioning a Central Venous Catheter, J Clinical Monitoring and Computing, pp. 331-334, vol. 17 No. 6, Aug. 2002.

(56) References Cited

OTHER PUBLICATIONS

Cavatorta, et al., "Central Venous Catheter Placement in Hemodialysis: Evaluation of Electrocardiography Using a Guidewire." The Journal of Vascular Access, vol. 2, pp. 45-50, 2001.
Chalkiadis, GA et al, Depth of Central Venous Catheter Insertion in Adults: An Audit and Assessment of a Technique to Improve Tip Position, Anaesth Intensive Care, pp. 61-66, vol. 26 No. 1, Feb. 1998.
Chamsi-Pasha, Hassan et al, Cardiac Complications of Total Parenteral Nutrition: The Role of Two-Dimensional Echocardiography in Diagnosis, Annals of the Royal College of Surgeons of England, pp. 120-123, vol. 71, 1989.
Chang, Thomas C. et al., Are Routine Ch Ladiographs Necessary After Image-Guided Placement of Internal Jugular Central Venous Access Devices?, AJR Feb. 1998;170:335-337.
Chaturvedi et al., "Catheter Malplacement During Central Venous Cannulation Through Arm Veins in Pediatric Patients." Journal of Neurosurgical Anesthesiology, vol. 15, No. 3 pp. 170-175, Jan. 2003.
Chen, Zhongping et al, Optical Doppler Tomography: Imaging in vivo Blood Flow Dynamics Following Pharmacological Intervention and Photodynamic Therapy, 7 pages, vol. 67, Photochemistry and Photobiology, 1998.
Cheng, Ki et al, A Novel Approach of Intravenous Electrocardiograph Technique in Correct Position the Long-Term Central Venous Catheter, Kaohsiung J Med Sci, pp. 241-247, vol. 16 No. 5, May 2000 (Abstract only).
Cheung, P., et al., The Effect of a Disposable Probe Cover on Pulse Oximetry, Anaesth Intensive Care 2002; 30: 211-214.
Chu, et al., "Accurate Central Venous Port-A Catheter Placement: Intravenous Electrocardiography and Surface Landmark Techniques Compared by Using Transesophageal Echocardiography." The International Anesthesia Research Society, vol. 98, pp. 910-914, 2004.
Claasz, Antonia et al, A Study of the Relationship of the Superior Vena Cava to the Bony Landmarks of the Sternum in the Supine Adult: Implications for Magnetic Guidance Systems, Journal, vol. 12 No. 3, JAVA, Jul. 24, 2007.
Clifford, et al. "Assessment of Hepatic Motion Secondary to Respiration for Computer Assisted Interventions" Computer Aided Surgery, vol. 7, pp. 291-299, 2002.
CN 200880012117.4 filed Apr. 16, 2008 First Office Action dated Dec. 23, 2011.
CN 200880012117.4 filed Apr. 16, 2008 Second Office Action dated Oct. 8, 2012.
CN 200880012117.4 filed Apr. 16, 2008 Third Office Action dated Apr. 27, 2013.
CN 200880125528.4 filed Nov. 25, 2008 First Office Action dated Jun. 5, 2012.
CN 200880125528.4 filed Nov. 25, 2008 Second Office Action dated Mar. 6, 2013.
CN 200880125528.4 filed Nov. 25, 2008 Third Office Action dated Jul. 1, 2013.
CN 200980123021.X filed Dec. 17, 2010 First Office Action dated Nov. 19, 2012.
CN 200980123021.X filed Dec. 17, 2010 Second Office Action dated Aug. 13, 2013.
CN 200980123021.X filed Dec. 17, 2010 Third Office Action dated Apr. 22, 2014.
CN 200980144663.8 filed May 9, 2011 First Office Action dated Dec. 5, 2012.
CN 200980144663.8 filed May 9, 2011 Second Office Action dated Aug. 22, 2013.
CN 200980144663.8 filed May 9, 2011 Third Office Action dated May 4, 2014.
CN 201080035659.0 filed Feb. 10, 2012 First Office Action dated Jan. 26, 2014.
CN 201080053838.7 filed May 28, 2012 First Office Action dated Jan. 6, 2014.
CN 201180016462.7 filed Sep. 27, 2012 First Office Action dated Mar. 21, 2014.
Colley, Peter S et al, ECG-Guided Placement of Sorenson CVP Catheters via Arm Veins, Anesthesia and Analgesia, pp. 953-956, vol. 63, 1984.
Collier, PE et al, Cardiac Tamponade from Central Venous Catheters, Am J Surg, pp. 212-214, vol. 176 No. 2, Aug. 1998.
ComboWire® Pressure/Flow Guide Wire Ref 9500 Series, Instructions for Use, Apr. 2011.
Corsten, et al., "Central Placement Catheter Placement Using the ECG-Guided Cavafix-Certodyn SD Catheter." Journal of Clinical Anesthesiology, vol. 6, Nov./Dec. 1994.
Cucchiara, Roy et al, Time Required and Success Rate of Percantaneous Right Atrial Catherization: Description of a Technique, Canad. Anaesth. Soc. J., pp. 572-573, vol. 27, No. 6, Nov. 1980.
Cullinane, DC et al, The Futility of Chest Roentgenograms Following Routine Central Venous Line Changes, Am J Surg, pp. 283-285, vol. 176 No. 3, Sep. 1998.
Curet, Myriam J. et al., University and Practice-based Physicians' Input on the Content of a Surgical Curriculum, The American Journal of Surgery® vol. 178 Jul. 1999, 78-84.
David, et al., "Is ECG-Guidance a Helpful Method to Correctly Position a Central Venous Catheter During Prehospital Emergency Care?" ACTA Anaesthesiologica Scandinavica, vol. 49, pp. 1010-1014, 2005.
DELTEC Cath-Finder® Tracking System Operation Manual, 1994.
Egelhof, Petra, Effects of Somatostatin on Portal Blood Flow and Portal Vein Pressure in Patients with Portal Hypertension due to Liver Cirrhosis Invasive Monitoring during TIPSS Procedures, Dissertation submitted to: Technical University of Munich, Faculty of Medicine, May 13, 2002; Date of examination: Feb. 26, 2003.
Engelhardt, W et al, ECG-Controlled Placement of Central Venous Catheters in Patients with Atrial Fibrallation, Anaesthesist, pp. 476-479, vol. 38 No. 9, Sep. 1989 (Abstract only).
EP 08855396.1 filed Jun. 15, 2010 European Search Report dated Jul. 31, 2012.
EP 08855396.1 filed Jun. 15, 2010 Intent to Grant dated Jul. 5, 2013.
EP 09707467.8 supplemental European search report dated Jun. 18, 2013.
EP 09808901.4 filed Aug. 21, 2009 European Search Report dated May 23, 2012.
EP 09808901.4 filed Aug. 21, 2009 Examination Report dated May 10, 2013.
EP 09813632.8 filed Apr. 5, 2011 European Search Report dated Jul. 4, 2012.
EP 09813632.8 filed Apr. 5, 2011 Office Action dated Apr. 30, 2013.
EP 09813632.8 filed Apr. 5, 2011 Summons to Attend Oral Proceedings dated Apr. 16, 2014.
EP 10 808 660.4 filed Feb. 15, 2012 Extended European Search Report dated Mar. 4, 2014.
EP 10786978.6 filed Dec. 19, 2011 Extended European Search Report dated Mar. 7, 2014.
EP 12177438.4 filed Jul. 23, 2012 Communication dated Jan. 13, 2014.
EP 12177438.4 filed Jul. 23, 2012 European Search Report dated Dec. 4, 2012.
EP 12177438.4 filed Jul. 23, 2012 extended European Search Report dated Mar. 25, 2013.
EP 13194818.4 filed Nov. 28, 2013 extended European search report dated Feb. 28, 2014.
EP 14151268.1 filed Jan. 15, 2014 European Search Report dated Feb. 21, 2014.
Fearon, William F et al, Evaluating Intermediate Coronary Lesions in the Cardiac Catheterization Laboratory, vol. 4, No. 1, 7 pages, Reviews in Cardiovascular Medicine, 2003.
Felleiter P et al, Use of Electrocardiographic Placement Control of Central Venous Catheters in Austria, Acta Med Austriaca, pp. 109-113, vol. 26 No. 3, 1999 (Abstract only).
Forauer, AR et al, Change in Peripherally Inserted Central Catheter Tip Location with Abduction and Adduction of the Upper Extremity, J Vasc Intery Radiol, pp. 1315-1318, vol. 11 No. 10, Nov.-Dec. 2000.

(56) References Cited

OTHER PUBLICATIONS

Frassinelli, P et al, Utility of Chest Radiographs after Guidewire Exchanges of Central Venous Catheters, Crit Care Med, pp. 611-615, vol. 26 No. 3, Mar. 1998.
Frazin L et al, A Doppler Guided Retrograde Catheterization System, Cathet. Cardiovasc Diagn, pp. 41-50, May 1992.
French, PJ et al, Sensors for Catheter Applications, Sensors Update, vol. 13 Issue 1 pp. 107-153, Dec. 2003.
GB Application 0800474.9 filed Aug. 24, 2006 Office Action dated Aug. 9, 2010.
Neurometer® CPT, Products Page. Neurotron, Inc. website: www.neurotron.com/products.html, last accessed Oct. 23, 2006.
Neurometer® Electrodiagnostic Neuroselective Sensory Nerve Evaluation: Charts, Tables, Documents & Downloads. Neurotron, Inc. website: www.neurotron.com/downloads.html, last accessed Oct. 23, 2006.
Odd, De et al, Does Radio-opaque Contrast Improve Radiographic localisation of Percutaneous Central Venous Lines?, Arch Dis Child Fetal Neonatal Ed, pp. 41-43, vol. 89 No. 1, Jan. 2004.
Palesty, JA et al, Routine Chest Radiographs Following Central Venous Recatherization over a Wire are not Justified, Am J Surg, pp. 618-621, vol. 176 No. 6, Dec. 1998.
Paliotti, Roberta P. et al, Intravascular Doppler Technique for Monitoring Renal Venous Blood Flow in Man, J Nephrol, pp. 57-62, 2003.
Parker, K.H. et al, Cardiovascular Fluid Dynamics, Department of Bioengineering, National Heart and Lung Institute, Imperial College of Science, Technology and Medicine, Cardiovascular Haemodynamics, pp. 1-28, Sep. 26, 2005.
Pawlik, et al., "Central Venous Catheter Placement: Comparison of the Intravascular Guidewire and the Fluid Column Electrocardiograms." European Journal of Anaesthesiology, vol. 41, pp. 594-599, 2004.
PCT/US13/62409 filed Sep. 27, 2013 International Search Report and Written Opinion dated Feb. 24, 2014.
PCT/US2006/033079 filed Aug. 24, 2006 International Preliminary Report on Patentability dated Feb. 26, 2008.
PCT/US2006/033079 filed Aug. 24, 2006 Search Report dated Dec. 19, 2006.
PCT/US2006/033079 filed Aug. 24, 2006 Written Opinion dated Dec. 19, 2006.
PCT/US2008/060502 filed Apr. 16, 2008 International Search Report and Written Opinion dated Oct. 16, 2008.
PCT/US2008/084751 filed Nov. 25, 2008 International Preliminary Report on Patentability dated Jun. 1, 2010.
PCT/US2008/084751 filed Nov. 25, 2008 Search Report dated May 20, 2009.
PCT/US2008/084751 filed Nov. 25, 2008 Written Opinion dated May 20, 2009.
PCT/US2009/033116 filed Feb. 4, 2009 International Preliminary Report on Patentability dated Aug. 10, 2010.
PCT/US2009/033116 filed Feb. 4, 2009 Search Report dated Mar. 13, 2009.
PCT/US2009/033116 filed Feb. 4, 2009 Written Opinion dated Mar. 13, 2009.
PCT/US2009/041051 filed Apr. 17, 2009 International Preliminary Report on Patentability dated Apr. 8, 2014.
PCT/US2009/041051 filed Apr. 17, 2009 Search Report dated Jul. 28, 2009.
PCT/US2009/041051 filed Apr. 17, 2009 Written Opinion dated Jul. 28, 2009.
PCT/US2009/054687 filed Aug. 21, 2009 International Preliminary Report on Patentability dated Feb. 22, 2011.
PCT/US2009/054687 filed Aug. 21, 2009 Search Report dated Oct. 6, 2009.
PCT/US2009/054687 filed Aug. 21, 2009 Written Opinion dated Oct. 6, 2009.
PCT/US2009/056567 filed Sep. 10, 2009 International Preliminary Report on Patentability dated Mar. 15, 2011.
PCT/US2009/056567 filed Sep. 10, 2009 Search Report dated Nov. 6, 2009.
PCT/US2009/056567 filed Sep. 10, 2009 Written Opinion dated Nov. 6, 2009.
PCT/US2010/038555 filed Jun. 14, 2010 Search Report dated Oct. 5, 2010.
PCT/US2010/038555 filed Jun. 14, 2010 Written Opinion dated Oct. 5, 2010.
PCT/US2010/045084 filed Aug. 10, 2010 International Preliminary Report on Patentability dated Feb. 23, 2012.
PCT/US2010/045084 filed Aug. 10, 2010 Search Report dated Apr. 14, 2011.
PCT/US2010/045084 filed Aug. 10, 2010 Written Opinion dated Apr. 14, 2011.
PCT/US2010/050773 filed Sep. 29, 2010 Search Report dated Jan. 24, 2011.
PCT/US2010/050773 filed Sep. 29, 2010 Written Opinion dated Jan. 24, 2011.
PCT/US2010/051917 filed Oct. 8, 2010 Search Report dated Nov. 29, 2010.
PCT/US2010/051917 filed Oct. 8, 2010 Written Opinion dated Nov. 29, 2010.
PCT/US2011/023497 filed Feb. 2, 2011 Search Report dated Jun. 6, 2011.
PCT/US2011/023497 filed Feb. 2, 2011 Written Opinion dated Jun. 6, 2011.
PCT/US2011/038391 filed May 27, 2011 International Preliminary Report on Patentability and Written Opinion dated Dec. 4, 2012.
PCT/US2011/038391 filed May 27, 2011 International Search Report dated Sep. 21, 2011.
PCT/US2011/038415 filed May 27, 2011 International Preliminary Report on Patentability dated Dec. 13, 2012.
PCT/US2011/038415 filed May 27, 2011 International Search Report dated Sep. 28, 2011.
PCT/US2011/038415 filed May 27, 2011 Written Opinion dated Sep. 28, 2011.
PCT/US2011/047127 filed Aug. 9, 2011 International Preliminary Report on Patentability dated Apr. 18, 2013.
PCT/US2011/047127 filed Aug. 9, 2011 International Search Report dated Feb. 29, 2012.
PCT/US2011/047127 filed Aug. 9, 2011 Written Opinion dated Feb. 29, 2012.
PCT/US2011/048403 filed Aug. 19, 2011 International Preliminary Report on Patentability dated Jul. 30, 2013.
PCT/US2011/048403 filed Aug. 19, 2011 International Search Report dated Dec. 15, 2011.
PCT/US2011/048403 filed Aug. 19, 2011 Written Opinion dated Dec. 15, 2011.
PCT/US2011/052793 filed Sep. 22, 2011 International Preliminary Report on Patentability dated Apr. 4, 2013.
U.S. Appl. No. 13/336,919, filed Dec. 23, 2011 Final Office Action dated Mar. 1, 2013.
U.S. Appl. No. 13/336,919, filed Dec. 23, 2011 Non-Final Office Action dated Dec. 27, 2013.
U.S. Appl. No. 13/336,919, filed Dec. 23, 2011 Non-Final Office Action dated Oct. 16, 2012.
U.S. Appl. No. 13/337,987, filed Dec. 27, 2011 Non-Final Office Action dated Mar. 15, 2013.
U.S. Appl. No. 13/469,932, filed May 11, 2012 Non-Final Office Action dated Jan. 3, 2014.
U.S. Appl. No. 13/665,420, filed Oct. 31, 2012 Non-Final Office Action dated Jan. 6, 2014.
U.S. Appl. No. 13/737,806, filed Jan. 9, 2013 Notice of Allowance dated Oct. 31, 2013.
U.S. Appl. No. 13/887,166, filed May 3, 2013 Non-Final Office Action dated Jan. 7, 2014.
U.S. Appl. No. 13/969,265, filed Aug. 16, 2013 Non-Final Office Action dated Dec. 19, 2013.
U.S. Appl. No. 29/428,649, filed Aug. 1, 2012 Notice of Allowance dated Jul. 5, 2013.

(56) References Cited

OTHER PUBLICATIONS

Valdivieso, J.R. Perez, et al., Evaluation of a formula for optimal positioning of a central venous catheter inserted through the right internal jugular vein, Rev. Esp. Anestesiol. Reanim. 2003; 50: 77-79.

VasoNova Inc, Vascular navigation system for accurate placement of PICCs, Start-Up Emerging Medical Ventures, pp. 44-45, vol. 14 No. 7, Jul.-Aug. 2009.

Vesely, Thomas M. et al., Central Venous Catheter Tip Position: A Continuing Controversy, J Vasc Intery Radiol 2003; 14:527-534.

VIASYS Health Care Inc. Cortrak © Fact Sheet, 2005.

VIASYS Healthcare MedSystems, Navigator® Benefits, 2008.

VIASYS Healthcare MedSystems, Navigator® Research in Cost Justification, 2008.

VIASYS MedSystems, Cortrak™ Systems Brochure, 2005.

Volcano ComboMap Features and Benefits/Technical Specifications, 2 pages, 2011.

Watters, et al. "Use of Electrocardiogram to Position Right Atrial Catheters During Surgery." Annals of Surgery, vol. 225, No. 2, pp. 165-171, 1997.

Welch Allyn Cardioperfect® PC-Based Resting ECG, 2003.

Wilson, R. G. et al, Right Atrial Electrocardiography in Placement of Central Venous Catheters, The Lancet, pp. 462-463, Feb. 27, 1988.

Wong, Jeffrey J. et al., Azygos Tip Placement for Hemodialysis Catheters in Patients with Superior Vena Cava Occlusion, Cardiovasc Intervent Radiol (2006) 29:143-146.

Worley, Seth J. "Use of a Real-Time Three-Dimensional Magenetic Navigation System for Radiofrequency Ablation of Accessory Pathways." PACE, vol. 21 pp. 1636-1643, Aug. 1998.

Yilmazlar A et al, Complications of 1303 Central Venous Cannulations, J R Soc Med, pp. 319-321, vol. 90 No. 6, Jun. 1997 (Abstract only).

Yoon, SZ et al, Usefulness of the Carina as a Radiographic Landmark for Central Venous Catheter Placement in Paediatric Patients, Br J Anaesth, Jul. 2005.

Yoshida, Teruhisa et al, Detection of Concealed Left Sided Accessory Atrioventricular Pathway by P Wave Signal Averaged Electrocardiogram, J Am Coll Cardiol, pp. 55-62, 1999.

Zaaroor, et al. "Novel Magnetic Technology for Intraoperative Intracranial Frameless Navigation: In Vivo and in Vitro Results." Neurosurgery, vol. 48, No. 5. pp. 1100-1107, May 2001.

Zachariou, Zacharias et al., Intra-atrial ECG recording: a new and safe method for implantation of Broviac catheters in children, Pediatr Surg Int (1994) 9: 457-458.

CN 201080035659.0 filed Feb. 10, 2012 Second Office Action dated Oct. 9, 2014.

CN 201080053838.7 filed May 28, 2012 Second Office Action dated Jun. 17, 2014.

CN 201180037065.8 filed Jan. 28, 2013 First Office Action dated Sep. 28, 2014.

CN 201180037068.1 filed Jan. 28, 2013 First Office Action dated Sep. 9, 2014.

CN 201180043512.0 filed Mar. 8, 2013 First Office Action dated Jul. 31, 2014.

CN 201180068309.9 filed Aug. 22, 2013 First Office Action dated Oct. 16, 2014.

EP 11 818 828.3 filed Mar. 18, 2013 Extended European Search Report dated Dec. 10, 2014.

EP 12177438.4 filed Jul. 23, 2012 Examination Report dated Dec. 5, 2014.

JP 2012-552060 filed Aug. 1, 2012 Office Action dated Nov. 12, 2014.

MX/a/2012/013858 filed Nov. 28, 2012 First Office Action dated Sep. 26, 2014.

RU 2011150917 filed Dec. 15, 2011 Second Office Action dated Aug. 28, 2014.

U.S. Appl. No. 12/426,175, filed Apr. 17, 2009 Examiners Answer dated Oct. 7, 2014.

U.S. Appl. No. 12/545,762, filed Aug. 21, 2009 Non-Final Office Action dated Nov. 7, 2014.

U.S. Appl. No. 12/815,331, filed Jun. 14, 2010 Final Office Action dated Dec. 23, 2014.

U.S. Appl. No. 12/815,331, filed Jun. 14, 2010 Non-Final Office Action dated Jul. 2, 2014.

U.S. Appl. No. 12/854,083, filed Aug. 10, 2010 Advisory Action dated Sep. 8, 2014.

U.S. Appl. No. 12/854,083, filed Aug. 10, 2010 Final Office Action dated Jul. 1, 2014.

U.S. Appl. No. 12/893,916, filed Sep. 29, 2010 Advisory Action dated Aug. 15, 2014.

U.S. Appl. No. 12/893,916, filed Sep. 29, 2010 Final Office Action dated Jun. 18, 2014.

U.S. Appl. No. 12/893,916, filed Sep. 29, 2010 Non-Final Office Action dated Sep. 25, 2014.

U.S. Appl. No. 13/118,138, filed May 27, 2011 Non-Final Office Action dated Oct. 9, 2014.

U.S. Appl. No. 13/240,171, filed Sep. 22, 2011 Non-Final Office Action dated Dec. 26, 2014.

U.S. Appl. No. 13/336,919, filed Dec. 23, 2011 Final Office Action dated Dec. 19, 2014.

U.S. Appl. No. 13/469,932, filed May 11, 2012 Non-Final Office Action dated Jul. 31, 2014.

U.S. Appl. No. 13/665,420, filed Oct. 31, 2012 Non-Final Office Action dated Oct. 9, 2014.

U.S. Appl. No. 13/887,166, filed May 3, 2013 Advisory Action dated Aug. 27, 2014.

U.S. Appl. No. 13/887,166, filed May 3, 2013 Final Office Action dated Jun. 23, 2014.

U.S. Appl. No. 13/890,158, filed May 8, 2013 Non-Final Office Action dated Aug. 15, 2014.

U.S. Appl. No. 13/969,265, filed Aug. 16, 2013 Notice of Allowance dated Jun. 23, 2014.

U.S. Appl. No. 14/141,046, filed Dec. 26, 2013 Non-Final Office Action dated Jun. 20, 2014.

CN 200980144663.8 filed May 9, 2011 Fourth Office Action dated Nov. 15, 2014.

CN 201080035659.0 filed Feb. 10, 2012 Third Office Action dated Mar. 19, 2015.

CN 201080053838.7 filed May 28, 2012 Third Office Action dated Dec. 4, 2014.

CN 201180016462.7 filed Sep. 27, 2012 Second Office Action dated Dec. 9, 2014.

CN 201180040151.4 filed Feb. 19, 2013 First Office Action dated Oct. 28, 2014.

CN 201180043512.0 filed Mar. 8, 2013 Second Office Action dated Apr. 14, 2015.

EP 12807886.2 filed Jan. 15, 2014 Extended European Search Report dated Feb. 6, 2015.

JP 2012-515222 filed Dec. 9, 2011 Office Action dated Feb. 23, 2015.

JP 2013-512046 filed Nov. 26, 2012 First Office Action dated Mar. 23, 2015.

JP 2013-512051 filed Nov. 26, 2012 First Office Action dated Mar. 23, 2015.

Moureau, Nancy L. et al., "Electrocardiogram (EKG) Guided Peripherally Inserted Central Catheter Placement and Tip Position: Results of a Trial to Replace Radiological Confirmation," Journal of the Association for Vascular Access, pp. 8-14, vol. 15, No. 1, 2010.

Pittiruti, et al, "The intracavitary ECG method for positioning the tip of central venous catheters: results of an Italian multicenter study," J Vasc Access, pp. 1-9, Nov. 21, 2011.

Pittiruti, et al. "The electrocardiographic method for positioning the tip of central venous catheters." JAVA, pp. 1-12, Feb. 12, 2011.

U.S. Appl. No. 12/815,331, filed Jun. 14, 2010 Advisory Action dated Mar. 5, 2015.

U.S. Appl. No. 12/854,083, filed Aug. 10, 2010 Non-Final Office Action dated Mar. 16, 2015.

U.S. Appl. No. 12/893,916, filed Sep. 29, 2010 Final Office Action dated Jan. 15, 2015.

U.S. Appl. No. 13/019,939, filed Feb. 2, 2011 Non-Final Office Action dated Feb. 9. 2015.

(56) References Cited

OTHER PUBLICATIONS

U.S. Appl. No. 13/118,033, filed May 27, 2011 Non-Final Office Action dated Feb. 3, 2015.
U.S. Appl. No. 14/141,046, filed Dec. 26, 2013 Non-Final Office Action dated Feb. 11, 2015.
U.S. Appl. No. 14/270,241, filed May 5, 2014 Non-Final Office Action dated Apr. 23, 2015.
CN 201180052587.5 filed Apr. 28, 2013 Second Office Action dated Aug. 19, 2015.
U.S. Appl. No. 12/854,083, filed Aug. 10, 2010 Final Office Action dated Aug. 21, 2015.
U.S. Appl. No. 12/893,916, filed Sep. 29, 2010 Non-Final Office Action dated Sep. 10, 2015.
U.S. Appl. No. 13/240,171, filed Sep. 22, 2011 Advisory Action dated Aug. 18, 2015.
U.S. Appl. No. 13/469,932, filed May 11, 2012 Non-Final Office Action dated Sep. 4, 2015.
U.S. Appl. No. 13/665,420, filed Oct. 31, 2012 Non-Final Office Action dated Jul. 9, 2015.
U.S. Appl. No. 13/890,158, filed May 8, 2013 Non-Final Office Action dated Jul. 9, 2015.
CA 2,721,715 filed Apr. 17, 2009 Examiner's Report dated Aug. 18, 2015.
CN 200980144663.8 filed May 9, 2011 Fifth Office Action dated May 26, 2015.
CN 201080053838.7 filed May 28, 2012 Fourth Office Action dated Jun. 2, 2015.
CN 201180016462.7 filed Sep. 27, 2012 Third Office Action dated Jun. 10, 2015.
CN 201180037065.8 filed Jan. 28, 2013 First Office Action dated Jun. 2, 2015.
CN 201180040151.4 filed Feb. 19, 2013 Second Office Action dated Jun. 19, 2015.
CN 201180068309.9 filed Aug. 22, 2013 Second Office Action dated May 6, 2015.
EP 11787515.3 filed Dec. 12, 2012 partial European search report dated Jun. 23, 2015.
EP 12177438.4 filed Jul. 23, 2012 European Search Report dated Jun. 7, 2015.
EP14197136.6 filed Dec. 10, 2014 Extended European Search Report dated May 26, 2015.
JP 2013-524999 filed Jan. 22, 2013 First Office Action dated Jun. 1, 2015.
MX/a/2012/013672 filed Nov. 23, 2012 First Office Action dated Aug. 10, 2015.
MX/a/2012/013858 filed Nov. 28, 2012 Second Office Action dated Jun. 10, 2015.
U.S. Appl. No. 1/118,033, filed May 27, 2011 Non-Final Office Action dated Jul. 8, 2015.
U.S. Appl. No. 12/815,331, filed Jun. 14, 2010 Non-Final Office Action dated Jun. 1, 2015.
U.S. Appl. No. 13/118,138, filed May 27, 2011 Non-Final Office Action dated Jul. 15, 2015.
U.S. Appl. No. 13/240,171, filed Sep. 22, 2011 Final Office Action dated Jun. 10, 2015.
U.S. Appl. No. 13/336,919, filed Dec. 23, 2011 Non-Final Office Action dated Jul. 9, 2015.
U.S. Appl. No. 13/887,166, filed May 3, 2013 Examiners Answer dated Jul. 16, 2015.
U.S. Appl. No. 14/548,151, filed Nov. 19, 2014 Non-Final Office Action dated Jun. 5, 2015.
CN 201180052587.5 filed Apr. 28, 2013 Office Action dated Feb. 24, 2016.
JP 2013-512046 filed Nov. 26, 2012 Office Action dated May 16, 2016.
U.S. Appl. No. 12/893,916, filed Sep. 29, 2010 Final Office Action dated Mar. 25, 2016.
U.S. Appl. No. 13/118,033, filed May 27, 2011 Final Office Action dated Apr. 1, 2016.
U.S. Appl. No. 13/118,138, filed May 27, 2011 Final Office Action dated Apr. 1, 2016.
U.S. Appl. No. 13/240,171, filed Sep. 22, 2011 Final Office Action dated May 6, 2016.
U.S. Appl. No. 13/469,932, filed May 11, 2012 Final Office Action dated Apr. 7, 2016.
U.S. Appl. No. 13/665,420, filed Oct. 31, 2012 Final Office Action dated Apr. 8, 2016.
U.S. Appl. No. 14/040,205, filed Sep. 27, 2013 Non-Final Office Action dated Mar. 10, 2016.
U.S. Appl. No. 14/201,300, filed Mar. 7, 2014 Final Office Action dated May 5, 2016.
U.S. Appl. No. 14/449,061, filed Jul. 31, 2014 Notice of Allowance dated Apr. 13, 2016.
U.S. Appl. No. 14/498,887, filed Sep. 26, 2014 Non-Final Office Action dated Feb. 19, 2016.
CN 201510144728.6 filed Apr. 17, 2015 Office Action dated Jan. 23, 2017.
CO 15110530 filed May 14, 2015 Office Action dated Nov. 25, 2016.
U.S. Appl. No. 12/426,175, filed Apr. 17, 2009 Notice of Allowance dated Dec. 13, 2016.
U.S. Appl. No. 14/040,205, filed Sep. 27, 2013 Advisory Action dated Dec. 15, 2016.
U.S. Appl. No. 14/054,700, filed Oct. 15, 2013 Advisory Action dated Dec. 15, 2016.
U.S. Appl. No. 14/201,300, filed Mar. 7, 2014 Final Office Action dated Dec. 19, 2016.
U.S. Appl. No. 14/615,932, filed Feb. 6, 2015 Non-Final Office Action dated Dec. 29, 2016.
U.S. Appl. No. 14/846,496, filed Sep. 4, 2015 Non-Final Office Action dated Nov. 25, 2016.
U.S. Appl. No. 15/160,958, filed May 20, 2016 Non-Final Office Action dated Dec. 15, 2016.
CA 2800810 filed Nov. 26, 2012 Office Action dated Mar. 30, 2017.
CN 200980144663.8 filed May 9, 2011 Decision of Re-Examination dated Feb. 21, 2017.
CN 201380065663.5 filed Jun. 15, 2015 Office Action dated Mar. 15, 2017.
EP 09743249.6 filed Oct. 18, 2010 Intention to Grant dated Mar. 2, 2017.
EP 13840356.3 filed Apr. 27, 2015 Extended European Search Report dated Mar. 22, 2017.
JP 2013-530322 filed Mar. 18, 2013, Office Action dated Mar. 2, 2017.
U.S. Appl. No. 12/545,762, filed Aug. 21, 2009 Final Office Action dated Apr. 10, 2017.
U.S. Appl. No. 13/665,420, filed Oct. 31, 2012 Non-Final Office Action dated Mar. 15, 2017.
U.S. Appl. No. 13/890,158 filed May 8, 2013 Non-Final Office Action dated Apr. 7, 2017.
U.S. Appl. No. 14/141,046, filed Dec. 26, 2013 Non-Final Office Action dated Apr. 7, 2017.
U.S. Appl. No. 14/201,300, filed Mar. 7, 2014 Advisory Action dated Mar. 2, 2017.
U.S. Appl. No. 14/201,300, filed Mar. 7, 2014 Non-Final Office Action dated Mar. 30, 2017.
U.S. Appl. No. 14/548,151, filed Nov. 19, 2014 Final Office Action dated Apr. 19, 2017.
U.S. Appl. No. 15/160,958, filed May 20, 2016 Final Office Action dated Apr. 21, 2017.
U.S. Appl. No. 15/284,355, filed Oct. 3, 2016 Non-Final Office Action dated Apr. 24, 2017.
CO 15110530 filed May 14, 2015 Office Action dated May 8, 2017.
EP 11850625.2 filed Jul. 22, 2013 Extended European Search Report dated Jun. 21, 2017.
EP 15746326.6 filed Jul. 1, 2016 Extended European Search Report dated Jun. 9, 2017.
EP 17157118.5 filed Feb. 21, 2017 Extended European Search Report Jun. 8, 2017.
JP 2015-534770 filed Mar. 26, 2015 Office Action dated Jun. 12, 2017.

(56) References Cited

OTHER PUBLICATIONS

U.S. Appl. No. 12/545,762, filed Aug. 21, 2009 Notice of Panel Decision dated Jul. 14, 2017.
U.S. Appl. No. 14/040,205, filed Sep. 27, 2013 Examiner's Answer dated Jul. 20, 2017.
U.S. Appl. No. 14/054,700, filed Oct. 15, 2013 Examiner's Answer dated Jul. 3, 2017.
U.S. Appl. No. 14/201,300, filed Mar. 7, 2014 Final Office Action dated Jul. 10, 2017.
U.S. Appl. No. 15/160,958, filed May 20, 2016 Advisory Action dated Jul. 10, 2017.
U.S. Appl. No. 15/160,958, filed May 20, 2016 Notice of Allowance dated Jul. 26, 2017.
U.S. Appl. No. 15/585,051, filed May 2, 2017 Non-Final Office Action dated Jul. 14, 2017.
CN 201610166569.4 filed Dec. 23, 2010, Office Action dated Nov. 1, 2017.
JP 2013-530322 filed Mar. 18, 2013, Office Action dated Nov. 6, 2017.
U.S. Appl. No. 13/887,166, filed May 3, 2013 Notice of Allowance dated Nov. 6, 2017.
U.S. Appl. No. 13/890,158, filed May 8, 2013 Final Office Action dated Nov. 21, 2017.
U.S. Appl. No. 14/141,046, filed Dec. 26, 2013 Final Office Action dated Dec. 11, 2017.
U.S. Appl. No. 14/788,305, filed Jun. 30, 2015 Non-Final Office Action dated Jan. 10, 2018.
U.S. Appl. No. 15/284,355, filed Oct. 3, 2016 Non-Final Office Action dated Nov. 17, 2017.
U.S. Appl. No. 15/365,698, filed Nov. 30, 2016 Non-Final Office Action dated Dec. 14, 2017.
U.S. Appl. No. 15/365,752, filed Nov. 30, 2016 Non-Final Office Action dated Dec. 13, 2017.
CN 201380065663.5 filed Jun. 15, 2015 Office Action dated Oct. 10, 2017.
CN 201510144728.6 filed Apr. 17, 2015 Office Action dated Aug. 29, 2017.
EP 10786978.6 filed Dec. 19, 2011 Office Action dated Aug. 11, 2017.
EP 11827551.0 filed Feb. 7, 2013 Extended European Search Report dated Sep. 19, 2017.
EP 14197137.4 filed Dec. 10, 2014 Office Action dated, Sep. 20, 2017.
EP 14761249.3 Filed Sep. 3, 2015 Office Action dated Sep. 28, 2017.
KR 10- 2013-7006933 filed Mar. 19, 2013 Office Action dated Aug. 7, 2017.
RU 2015111669 filed Apr. 1, 2015 Office Action dated Sep. 5, 2017.
U.S. Appl. No. 13/887,166, filed May 3, 2013 Appeal Decision dated Aug. 17, 2017.
U.S. Appl. No. 14/548,151, filed Nov. 19, 2014 Advisory Action dated Aug. 1, 2017.
U.S. Appl. No. 14/548,151, filed Nov. 19, 2014 Non-Final Office Action dated Sep. 21, 2017.
U.S. Appl. No. 14/788,305, filed Jun. 30, 2015 Restriction Requirement dated Aug. 25, 2017.
AU 2012278809 filed Nov. 12, 2013 Notice of Acceptance dated Sep. 13, 2016.
CA 2,721,715 filed Apr. 17, 2009 Examiner's Report dated Oct. 25, 2016.
CN 201180037065.8 filed Jan. 28, 2013 Notice of Grant dated Aug. 30, 2016.
EP 13840356.3 filed Apr. 27, 2015 Partial European Search Report dated Oct. 19, 2016.
EP 13846380.7 filed May 15, 2015 Partial European Search Report dated Sep. 30, 2016.
EP 14761249.3 Filed Sep. 3, 2015 Extended European Search Report dated Sep. 19, 2016.
KR 10-2012-7000866 filed Jan. 11, 2012 Second Office Action dated Nov. 3, 2016.
PCT/US2016/039356 filed Jun. 24, 2016 International Search Report and Written Opinion dated Sep. 16, 2016.
U.S. Appl. No. 12/426,175, filed Apr. 17, 2009 Decision on Appeal dated Nov. 7, 2016.
U.S. Appl. No. 12/545,762, filed Aug. 21, 2009 Non-Final Office Action dated Sep. 26, 2016.
U.S. Appl. No. 12/893,916, filed Sep. 29, 2010 Non-Final Office Action dated Aug. 31, 2016.
U.S. Appl. No. 13/118,033, filed May 27, 2011 Notice of Allowance dated Sep. 2, 2016.
U.S. Appl. No. 14/040,205, filed Sep. 27, 2013 Final Office Action dated Oct. 19, 2016.
U.S. Appl. No. 14/054,700, filed Oct. 15, 2013 Final Office Action dated Oct. 19, 2016.
U.S. Appl. No. 14/201,300, filed Mar. 7, 2014 Non-Final Office Action dated Aug. 24, 2016.
U.S. Appl. No. 14/548,151, filed Nov. 19, 2014 Non-Final Office Action dated Sep. 28, 2016.
CN 201410009216.4 filed Jan. 8, 2014 Office Action dated Jun. 15, 2016.
KR 10-2012-7000866 filed Jan. 11, 2012 First Office Action dated Jun. 16, 2016.
RU 2013158008 filed Dec. 26, 2013 First Office Action dated May 27, 2016.
U.S. Appl. No. 12/893,916, filed Sep. 29, 2010 Advisory Action dated Jun. 2, 2016.
U.S. Appl. No. 13/240,171, filed Sep. 22, 2011 Advisory Action dated Jul. 22, 2016.
U.S. Appl. No. 13/336,919, filed Dec. 23, 2011 Notice of Allowance dated Jul. 26, 2016.
U.S. Appl. No. 13/469,932, filed May 11, 2012 Advisory Action dated Jun. 27, 2016.
U.S. Appl. No. 13/890,158, filed May 8, 2013 Advisory Action dated Jul. 26, 2016.
U.S. Appl. No. 14/141,046, filed Dec. 26, 2013 Advisory Action dated Aug. 4, 2016.
U.S. Appl. No. 14/201,300, filed Mar. 7, 2014 Advisory Action dated Jul. 18, 2016.
U.S. Appl. No. 14/309,511, filed Jun. 19, 2014 Notice of Allowance, dated Jul. 26, 2016.
U.S. Appl. No. 14/498,887 filed Sep. 26, 2014 Advisory Action dated Aug. 22, 2016.
U.S. Appl. No. 14/498,887 filed Sep. 26, 2014 Final Office Action dated Jun. 15, 2016.
U.S. Appl. No. 14/548,151, filed Nov. 19, 2014 Advisory Action dated Jul. 22, 2016.
CN 201180037065.8 filed Jan. 28, 2013 Fourth Office Action dated May 5, 2016.
JP 2014-519081 filed Dec. 27, 2013 First Office Action dated Apr. 26, 2016.
JP2013-530322 filed Mar. 18, 2013, Office Action dated May 2, 2016.
U.S. Appl. No. 14/141,046, filed Dec. 26, 2013 Final Office Action dated May 11, 2016.
CN 201380051172.5 filed Mar. 30, 2015 Office Action dated Jan. 16, 2018.
CN 201480010988.8 filed Aug. 27, 2015 Office Action dated Dec. 13, 2017.
CN 201610127217.8 filed Mar. 7, 2016 Office Action dated Dec. 28, 2017.
EP 15179061.5 filed Jul. 30, 2015 Partial European Search Report dated Jan. 17, 2018.
EP 17186624.7 filed Aug. 17, 2017 Partial European Search Report dated Jan. 17, 2018.
MX/a/2015/004864 filed Apr. 16, 2015 Office Action dated Dec. 18, 2017.
RU 2015111669 filed Apr. 1, 2015 Office Action dated Jan. 25, 2018.
U.S. Appl. No. 13/665,420, filed Oct. 31, 2012 Notice of Allowance dated Feb. 7, 2018.
U.S. Appl. No. 13/890,158, filed May 8, 2013 Advisory Action dated Feb. 13, 2018.

(56) References Cited

OTHER PUBLICATIONS

U.S. Appl. No. 15/365,734, filed Nov. 30, 2016 Non-Final Office Action dated Feb. 23, 2018.
U.S. Appl. No. 15/585,051, filed May 2, 2017 Final Office Action dated Feb. 28, 2018.
CA 2800810 filed Nov. 26, 2012 Office Action dated Mar. 13, 2018.
EP 14197137.4 filed Dec. 10, 2014 Office Action dated Apr. 5, 2018.
JP 2015-534770 filed Mar. 26, 2015 Office Action dated Feb. 21, 2018.
MX/a/2015/004864 filed Apr. 16, 2015 Office Action dated Apr. 24, 2018.
PCT/US2017/066503 filed Dec. 14, 2017 International Search Report and Written Opinion dated Feb. 20, 2018.
AZoMaterials. Nickel-Based Super Alloy Inconel 625—Properties and Applications by United Performance Alloys. Oct. 27, 2015. Last accessed Mar. 23, 2018. <URL:https://web.archive.org/web/20151027202821/https://www.azom.com/article.aspx?ArticleID=4461>.
NOT Resource Center. Magnetic Permeability. Oct. 18, 2014. Last accessed Mar. 23, 2018. <URL:https://web.archive.org/web/20141018213902/https://www.nde-ed.org/EducationResources/CommunityCollege/Materials/Physical_Chemical/Permeability.htm>.
U.S. Appl. No. 14/201,300, filed Mar. 7, 2014 Examiner's Answer dated Apr. 19, 2018.
U.S. Appl. No. 15/192,561, filed Jun. 24, 2016 Non-Final Office Action dated Apr. 6, 2018.
U.S. Appl. No. 15/365,872, filed Nov. 30, 2016 Restriction Requirement dated Apr. 5, 2018.
U.S. Appl. No. 15/585,051, filed May 2, 2017 Final Office Action dated Mar. 15, 2018.

* cited by examiner

STYLET APPARATUSES AND METHODS OF MANUFACTURE

PRIORITY

This application is a division of U.S. patent application Ser. No. 11/466,602, filed Aug. 23, 2006, now U.S. Pat. No. 8,784,336, which claims the benefit of U.S. Provisional Application No. 60/710,760, filed Aug. 24, 2005, and U.S. Provisional Application No. 60/745,109, filed Apr. 19, 2006, the disclosure of each of which is incorporated, in its entirety, by this reference.

BACKGROUND

One function of a stylet is to facilitate the navigation of a catheter, cannula, hollow needle, or the like within a select portion of a patient, such as within a patient's vasculature, by providing (i.e., imparting) rigidity or stiffness to the catheter. For example, a stylet may comprise a slender, solid, and/or hollow metal member that, when positioned within a lumen of a catheter, stiffens the catheter sufficiently to allow for placement of the catheter within the patient.

BRIEF SUMMARY

In at least one embodiment, a stylet capable of being at least partially disposed within a lumen of a device may comprise an elongated body comprising a proximal end, a distal end, and at least one magnetic material. The elongated body may also further comprise at least one core element, a tubular member circumferentially disposed about at least a portion of the core element, and/or a support member circumferentially disposed about at least a portion of the core element. A matrix material may also be disposed between the core element and the tubular member to retain the magnetic material within the elongated body.

In certain embodiments, the core element may comprise a first region, a second region having a diameter that is less than a diameter of the first region, and a transition region coupling the second region to the first region. The magnetic material may be circumferentially disposed about at least a portion of the second region of the core element, disposed within the tubular member, positioned proximate the distal end of the elongated body of the stylet, or otherwise positioned within the elongated body of the stylet. For example, in certain embodiments, at least one of the core element, the tubular member, and the support member may comprise a magnetic region and a non-magnetic region. In addition, the magnetic material may comprise at least one permanent magnet coupled to the elongated body of the stylet.

According to certain embodiments, the tubular member may be circumferentially disposed about at least a portion of the support member. In an additional embodiment, the support member may be circumferentially disposed about at least a portion of the tubular member. In addition, the tubular member may comprise a reinforcing element and/or a groove defined within the tubular member. The elongated body may also comprise at least one core element and a coating circumferentially disposed about at least a portion of the core element and at least a portion of the magnetic material.

In certain embodiments, a method of manufacturing a stylet may comprise forming an elongated body comprising a proximal end, a distal end, and at least one magnetic material. In at least one embodiment, the step of forming the elongated body may comprise magnetizing at least a portion of the elongated body. The step of forming the elongated body may also further comprise disposing a support member about at least a portion of the core element and/or disposing a matrix material between the core element and the tubular member to retain the magnetic material within the elongated body. In addition, the step of forming the elongated body may comprise providing at least one core element, disposing a tubular member about at least a portion of the core element, and disposing the magnetic material within the tubular member.

In at least one embodiment, a catheter assembly may comprise a catheter defining a lumen and at least one stylet at least partially disposed within the lumen of the catheter. In certain embodiments, the at least one stylet may comprise an elongated body comprising a proximal end, a distal end, and at least one magnetic material.

Features from any of the above mentioned embodiments may be used in combination with one another in accordance with the instant disclosure. In addition, other features and advantages of the instant disclosure will become apparent to those of ordinary skill in the art through consideration of the ensuing description, the accompanying drawings, and the appended claims.

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

Figure 1:
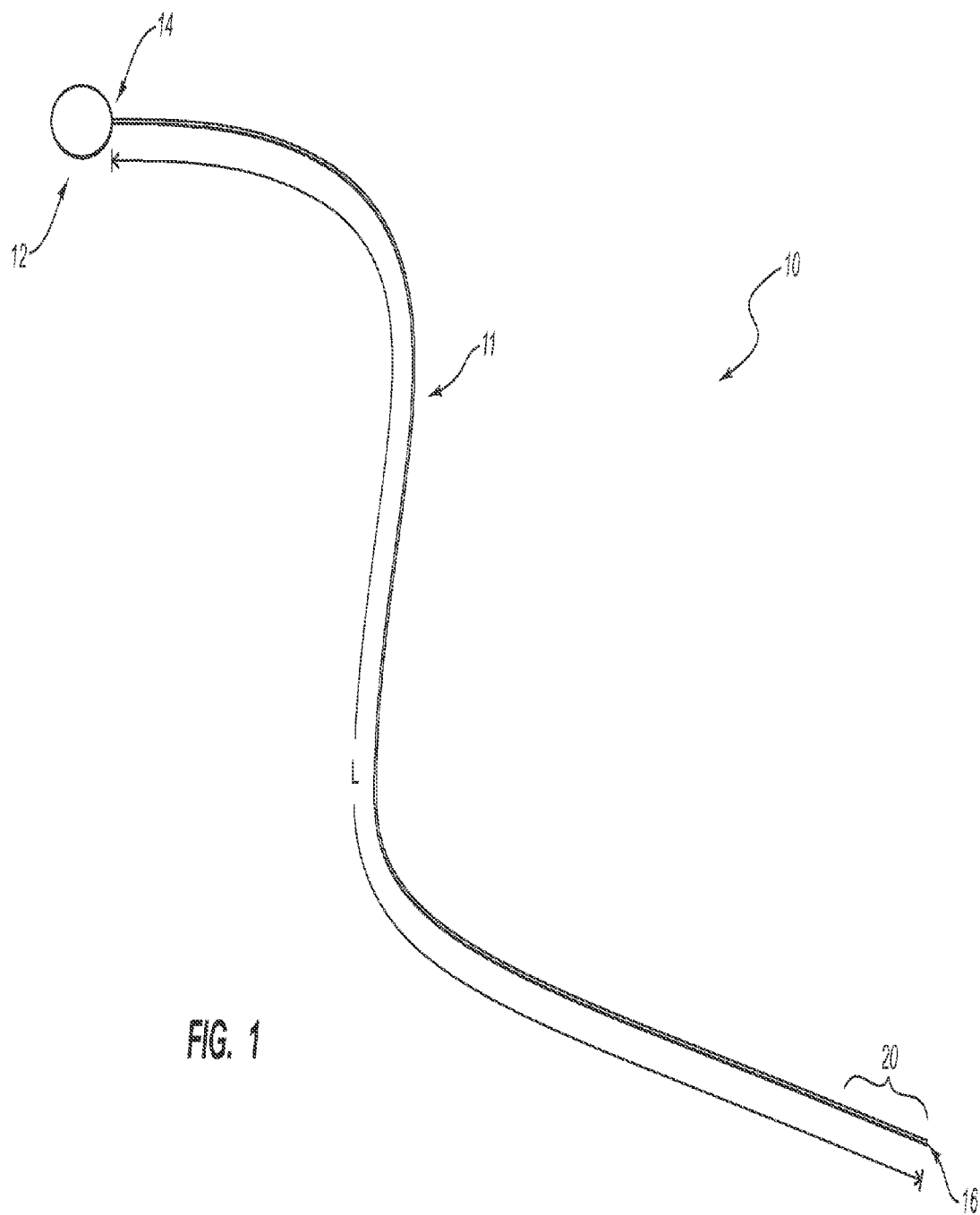
FIG. 1 is a schematic view of an exemplary stylet according to at least one embodiment.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, one of skill in the art will understand that the exemplary embodiments described herein are not intended to be limited to the particular forms disclosed. Rather, the instant disclosure covers all modifications, equivalents, and alternatives falling within the scope of the appended claims.

DETAILED DESCRIPTION

FIG. 1 is a schematic view of an exemplary stylet 10 according to at least one embodiment. For purposes of this disclosure, the term "stylet" shall be broadly construed to include any form or type of structure capable of being at least partially positioned or disposed within a lumen of a catheter, cannula, hollow needle, or other suitable device to provide (i.e., impart) increased stiffness or rigidity to the device. As seen in FIG. 1, in at least one embodiment, stylet 10 may comprise an elongated body 11 extending between a proximal end 14 and a distal end 16. Elongated body 11 may be formed in any number of shapes and sizes. For example, in certain embodiments, elongated body 11 may have a substantially constant cross-sectional size, taken transverse to the longitudinal axis of elongated body 11. Elongated body 11 may also have a length L extending from proximal end 14 to distal end 16, as shown in FIG. 1. In certain embodiments, a tab element 12 may also be provided at the proximate end 14 of elongated body 11 to provide a convenient and easily graspable structure for a user to grasp when manipulating stylet 10.

Elongated body 11 of stylet 10 may comprise any number or combination of materials. For example, in at least one embodiment, and as discussed in greater detail below, at least a portion of elongated body 11 may comprise at least one magnetic material. In general, this magnetic material may comprise any type or form of magnetic material, including both permanent magnetic materials and electromagnetic materials. For example, in one embodiment, elongated body 11 of stylet 10 may comprise a rare-earth magnet (e.g., samarium cobalt and/or neodymium iron boron). In another embodiment, elongated body 11 of stylet 10 may comprise an AlNiCo magnetic material, a plastic magnetic material (e.g., PANiCNQ), or a ceramic magnetic material, such as barium ferrite ($BaO_6Fe_2O_3$) or strontium ferrite ($SrO_6Fe_2O_3$) and iron oxide ($Fe_3O_4$). Elongated body 11 of stylet 10 may also comprise, in certain embodiments, an electromagnetic material, such as a solenoid, that generates a magnetic field upon application of an electric current.

As discussed in greater detail below, elongated body 11 of stylet 10 may comprise both solid (including both pliant and rigid solids) or non-solid magnetic materials. For example, elongated body 11 of stylet 10 may comprise a magnetic material having a plurality of magnetic particles dispersed within a pliable material, such as a putty, polymer, silicone, highly viscous liquid, or any other suitable material. In additional embodiments, elongated body 11 of stylet 10 may comprise a magnetic material having a plurality of magnetic particles contained within a matrix, suspension, or slurry. This exemplary magnetic suspension or slurry may comprise any liquid (e.g., oil, water, glycerin, alcohol, polymers, or the like) in combination with any type of magnetic material, such as particulate magnetic materials.

In at least one embodiment, exemplary stylet 10 may comprise a magnetic material that exhibits an observable dipole (e.g., an individual magnetic dipole or a collective magnetic dipole exhibited by a plurality of magnets), which may provide an indication of the position and/or orientation of the magnetic material and, therefore, the position and/or orientation of at least a portion of exemplary stylet 10. For example, stylet 10 may comprise a magnetic material having a magnetic dipole that, when stylet 10 is inserted into a patient, may be detected from outside of the patient's body using detection technology (discussed in greater detail below) to indicate the position and/or orientation of stylet 10 within the patient's body. In many embodiments, the magnetic material of stylet 10 may exhibit a relatively high field strength for a given volume so that the orientation of its magnetic dipole may be easily detected.

Generally speaking, the poles of the magnetic material of stylet 10 may be positioned or oriented in any number of ways. For example, the dipole of the magnetic material of exemplary stylet 10 may either be oriented substantially parallel to the longitudinal axis of stylet 10 (i.e., the axis extending from proximal end 14 to distal end 16 of stylet 10) or substantially perpendicular to the longitudinal axis of stylet 10. In addition, the north pole of the magnetic material of stylet 10 may be positioned proximate to the distal end 16 of stylet 10, with the south pole of the magnetic material facing the proximate end 14 of stylet 10.

In general, any type or form of detection system may be used to detect the dipole of the magnetic material of stylet 10 to provide an indication of the position and/or orientation of the magnetic material and, therefore, the position and/or orientation of at least a portion of exemplary stylet 10 positioned within a patient's body. Examples of suitable detection apparatuses include, without limitation, the various detection apparatuses disclosed in U.S. Pat. Nos. 5,879,297; 6,129,668; 6,216,028; and 6,263,230 to Haynor et al. ("the Haynor Patents"), the entirety of each of which is incorporated, in its entirety, by this reference. For example, an exemplary detection apparatus may comprise a plurality of magnetic sensors oriented in a known direction to generate a set of signals based on the strength and direction of the magnetic field generated by the magnetic material (or plurality of magnetic materials) of stylet 10. A processor may then calculate an estimated position of the magnetic material of stylet 10 in a three-dimensional space based on the predicted and actual magnetic field strength of the magnetic material derived from the set of signals generated by the magnetic sensors. For example, the location and/or orientation of the magnetic material of stylet 10 may be calculated by comparing the difference between the predicted magnetic field strength and the actual measured magnetic field strength of the magnetic material. In certain embodiments, a display connected to the processor may display the position of the magnetic material of the stylet 10 in a three-dimensional space. Accordingly, a detection apparatus, such as the exemplary detection apparatus described herein, may detect the magnetic field generated by the magnetic material of stylet 10 positioned within a patient's body in order to determine the position and/or orientation of at least a portion of stylet 10.

Figure 2:
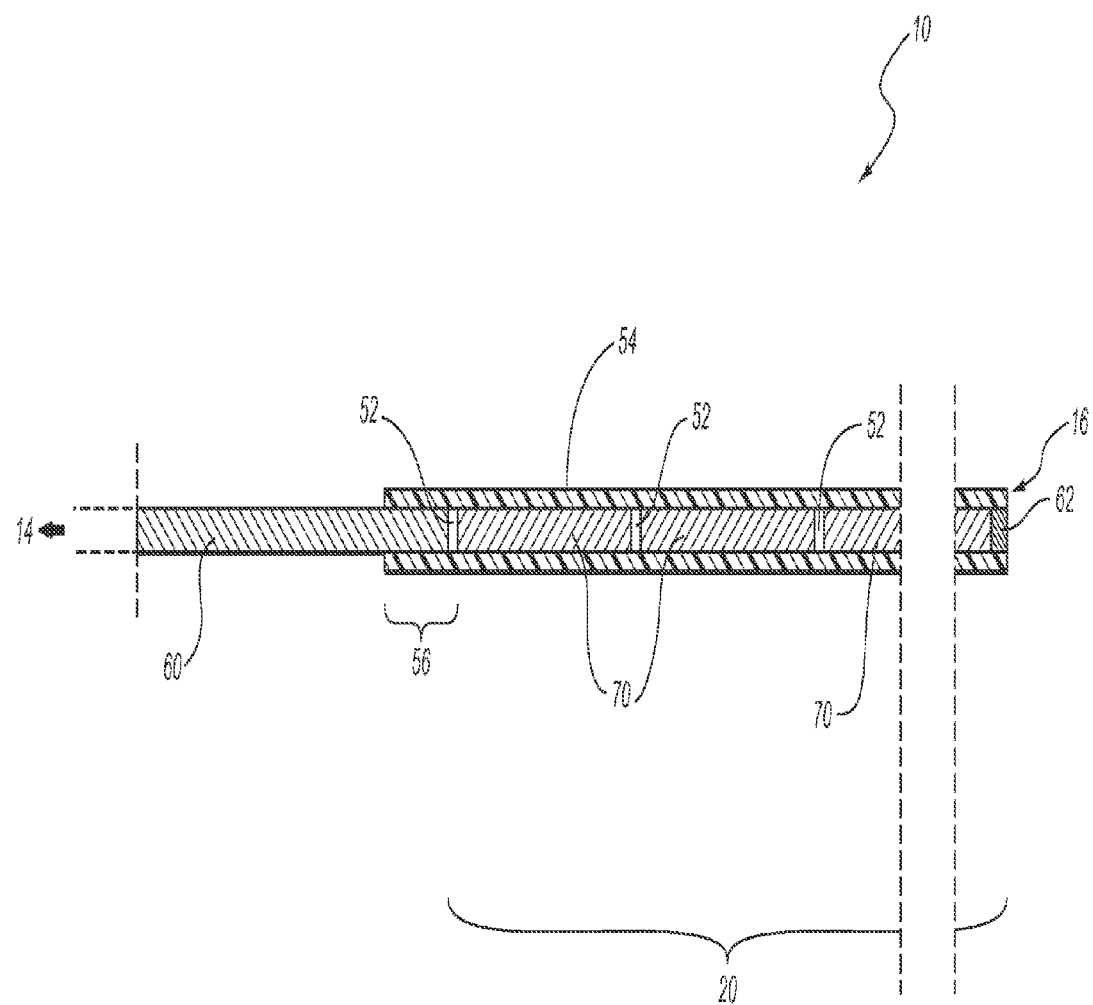
FIG. 2 is a partial cross-sectional side view of an exemplary stylet comprising a plurality of magnetic elements according to at least one embodiment.

FIG. 2 is a partial cross-sectional side view of an exemplary stylet 10 according to at least one embodiment. As seen in this figure, exemplary stylet 10 may comprise a tubular member 54 circumferentially disposed about at least a portion of an elongated core element 60. Core element 60 may be formed in any number of shapes and sizes and of any number or combination of suitable materials; including, for example, conventional stylet materials such as stainless steel. Similarly, tubular member 54, which generally represents any structure capable of at least partially surrounding at least a portion of core element 60, may be formed of any number or combination of materials; including, for example, polymers (such as polyimide, silicone, or so-called heat shrink tubing), metal, or other suitable materials. Tubular member 54 may be positioned so as to surround all or merely a portion of the length of core element 60. For example, in the exemplary embodiment illustrated in FIG. 2, tubular member 54 may be coupled to, and at least partially surround, a distal region 56 of core element 60. In additional embodiments, described and illustrated below, tubular member 54 may extend along the entire length of core element 60; i.e., from distal end 16 to proximate end 14. Tubular member 54 may also be coupled or affixed to at least a portion of core element 60 in any number of ways; including, for example, by adhering, melting, or otherwise affixing tubular member 54 to the outer surface of core element 60.

In at least one embodiment, exemplary stylet 10 may comprise one or more magnetic elements 70. As detailed above, magnetic elements 70 may comprise any type or form or magnetic material, such as, for example, a rare-earth magnet or a ceramic magnetic material. In general, magnetic elements 70 may be positioned within either a select region of, or throughout the entirety of, elongated body 11. For example, in the exemplary embodiment illustrated in FIG. 2, magnetic elements 70 may be positioned within a distal region 20 of stylet 10. In certain embodiments, magnetic elements 70 may be housed within tubular member 54. In general, magnetic elements 70 may be retained within tubular member 54 in any number of ways; including, for example, by a closure element 62 provided at the distal end 16 of stylet 10. In additional embodiments, magnetic elements 70 may be coupled to tubular member 54 by an adhesive, polymer, gel, epoxy, or other suitable material.

In at least one embodiment, one or more gaps 52 may be provided between longitudinally adjacent magnetic elements 70. In certain embodiments, gaps 52 may increase the flexibility of distal region 20 of stylet 10 and may allow tubular member 54 to be bent without bringing longitudinally adjacent magnetic elements 70 into contact with one another. The size and configuration of gaps 52 may also be modified as needed to impart a desired level of stiffness or flexibility to distal region 20 of stylet 10. In addition, gaps 52 may be filled with a pliant filling material, such as, for example, silicone, rubber, or any other suitable material. In certain embodiments, gaps 52 may enable exemplary stylet 10, in combination with a catheter, to traverse an arcuate subcutaneous path within a patient.

As detailed above, tubular member 54 may be formed of any number or combination of materials. For example, in at least one embodiment, tubular member 54 may comprise a metal or metallic material that exhibits a desired level of stiffness. In this exemplary embodiment, the stiffness or flexibility of tubular member 54 may be adjusted by modifying the thickness of the outer wall of metallic tubular member 54 and/or by defining a plurality of grooves, holes, notches, or other features within the outer wall of tubular member 54, as discussed in greater detail below.

Figure 3:
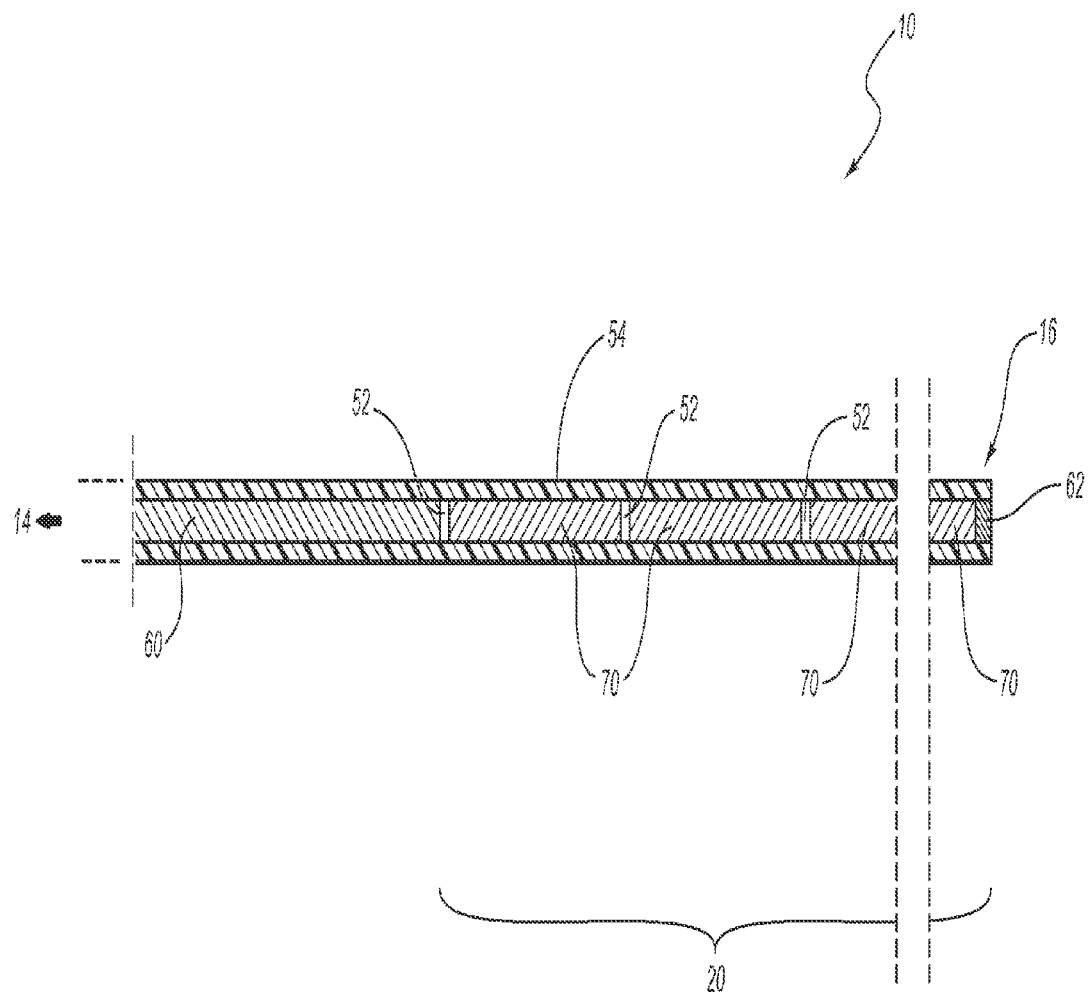
FIG. 3 is a partial cross-sectional side view of an exemplary stylet according to an additional embodiment.

FIG. 3 is a partial cross-sectional side view of an exemplary stylet 10 according to an additional embodiment. As seen in this exemplary embodiment, exemplary stylet 10 may comprise a tubular member 54 circumferentially disposed about an elongated core element 60 and a plurality of magnetic elements 70. In contrast to the exemplary embodiment illustrated in FIG. 2, tubular member 54 may extend along, and be circumferentially disposed about, substantially the entire length of core element 60. In other words, tubular member 54 may extend substantially between proximal end 14 and distal end 16 of exemplary stylet 10. In certain embodiments, this configuration may help resist movement of core element 60 relative to tubular member 54.

Figure 4:
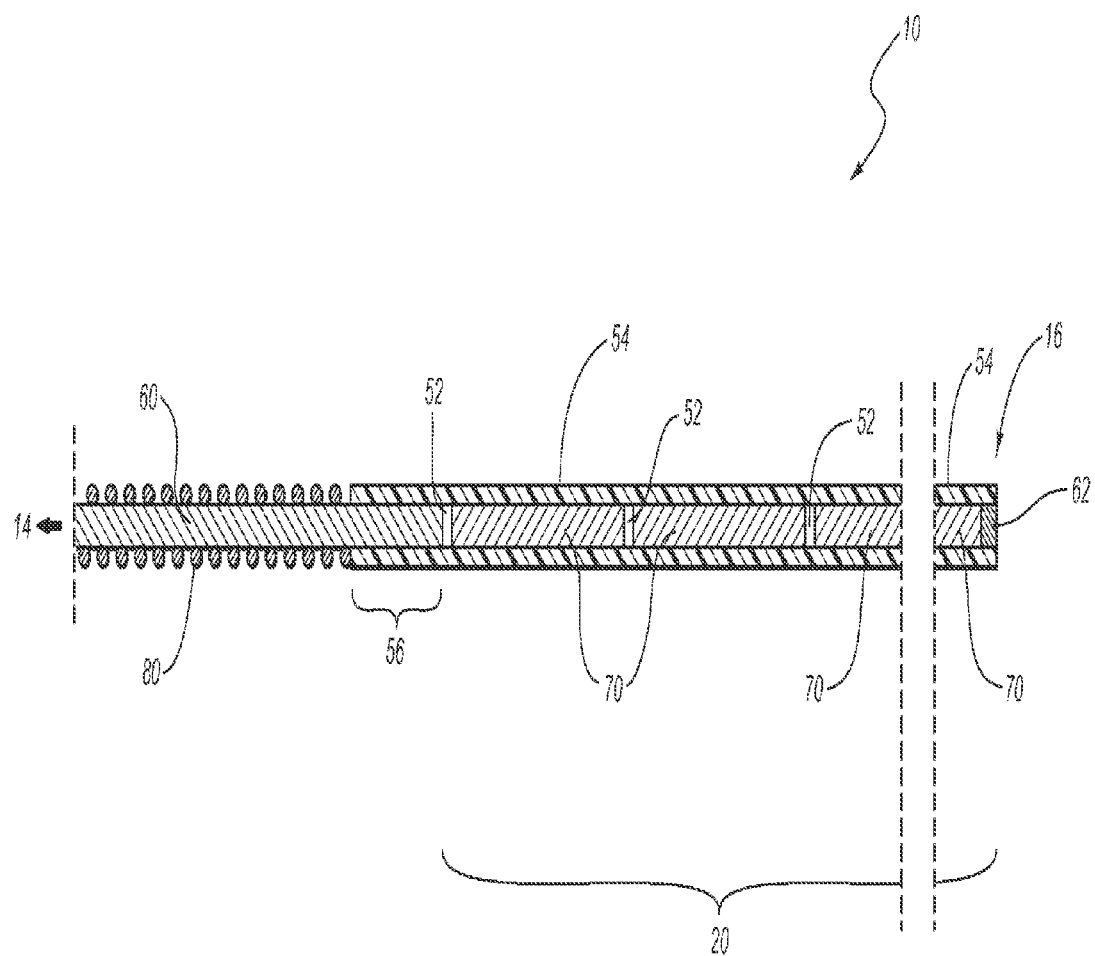
FIG. 4 is a partial cross-sectional side view of an exemplary stylet according to an additional embodiment.

FIG. 4 is a partial cross-sectional side view of an exemplary stylet 10 according to an additional embodiment. As seen in this figure, exemplary stylet 10 may comprise an elongated core element 60, a tubular member 54 circumferentially disposed about a distal region 56 of core element 60, and a plurality of magnetic elements 70 housed within tubular member 54 proximate distal region 20. In at least one embodiment, exemplary stylet 10 may also comprise at least one support element 80 circumferentially disposed about at least a portion of core element 60. Support element 80 generally represents any form or type of structure or element capable of providing a select level of flexibility or rigidity to core element 60 and/or exemplary stylet 10. Examples of support element 80 include support coils, wires, or the like. In certain embodiments, support element 80 may be affixed or bonded to at least a portion of the outer surface of core element 60, which may allow for select tailoring of the amount of rigidity or stiffness provided by support element 80. Optionally, support element 80 may be integrally formed with, or disposed within, at least a portion of core element 60. In certain embodiments, and as illustrated in FIG. 4, the distal end of support element 80 may be positioned proximate or adjacent to the proximal end of tubular member 54.

Figure 5:
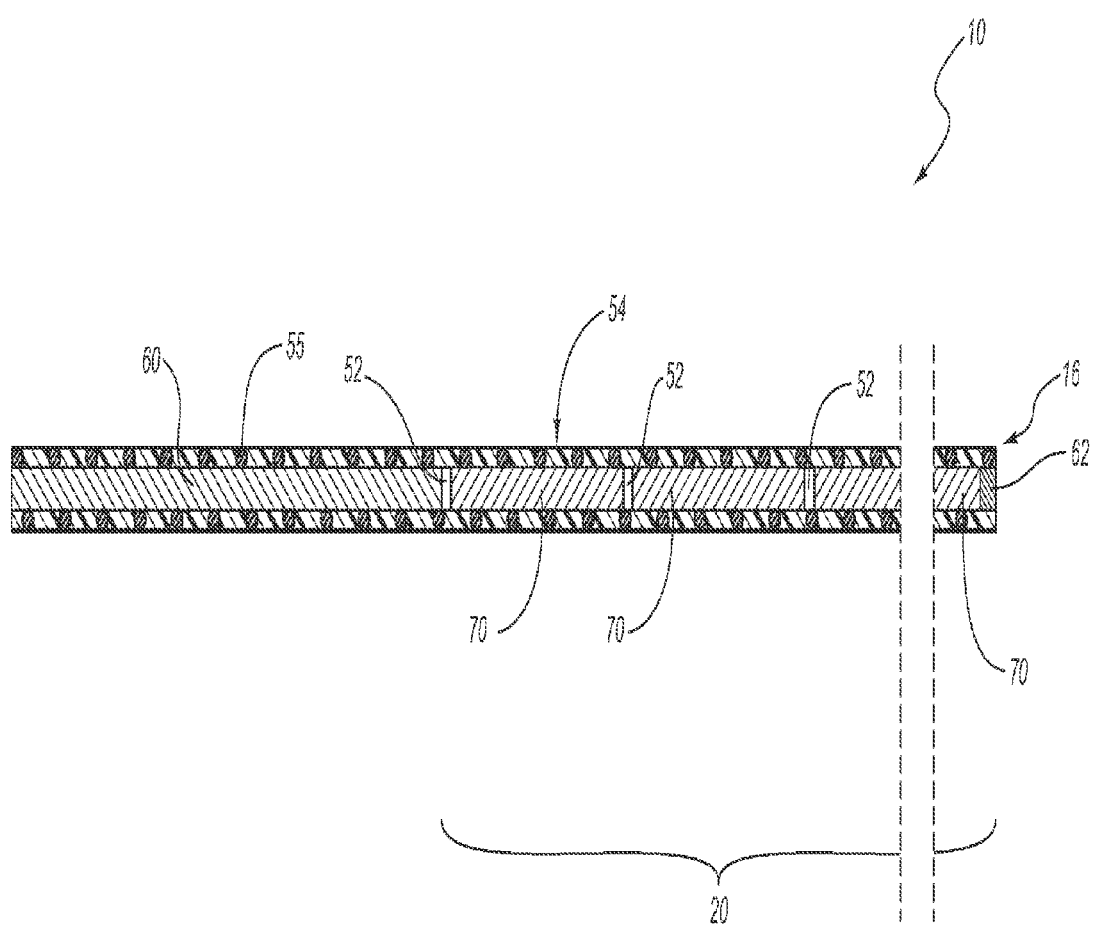
FIG. 5 is a partial cross-sectional side view of an exemplary stylet according to an additional embodiment.

FIG. 5 is a partial cross-sectional side view of an exemplary stylet 10 according to an additional embodiment. As seen in this figure, exemplary stylet 10 may comprise an elongated core element 60, a tubular member 54 circumferentially disposed about substantially the entire length of core element 60, and a plurality of magnetic elements 70 housed within tubular member 54 proximate distal region 20. In at least one embodiment, tubular member 54 of exemplary stylet 10 may also comprise a reinforcing element 55. Reinforcing element 55 generally represents any type or form of structure capable of providing a desired level of flexibility or stiffness to tubular member 54 and/or exemplary stylet 10. Examples of reinforcing element 55 include a reinforcing coil or braid, a flexible reinforcing wire, or the like. Reinforcing element 55 may be positioned within, integrally formed with, adhered to, or otherwise attached to tubular member 54 in any number of ways. Reinforcing element 55 may also be oriented relative to exemplary stylet 10 in any number of ways; including, for example, longitudinally along at least a portion of the length of stylet 10 (i.e., longitudinally along an elongation axis of stylet 10) or radially about portions of stylet 10 (e.g., radially, helically, or otherwise wrapped about portions of stylet 10). In addition, reinforcing element 55 may or may not be coupled to tubular member 54. As with tubular member 54, reinforcing member 55 may extend along a portion of core element 60 within a region 56, or may extend along substantially the entire length of core element 60 (i.e., from the proximal end 14 to the distal end 16 of stylet 10). In certain embodiments, the size, length, or stiffness of, and/or the material used to form reinforcement element 55 may be selected based on a desired level of flexibility or rigidity for stylet 10.

Figure 6:
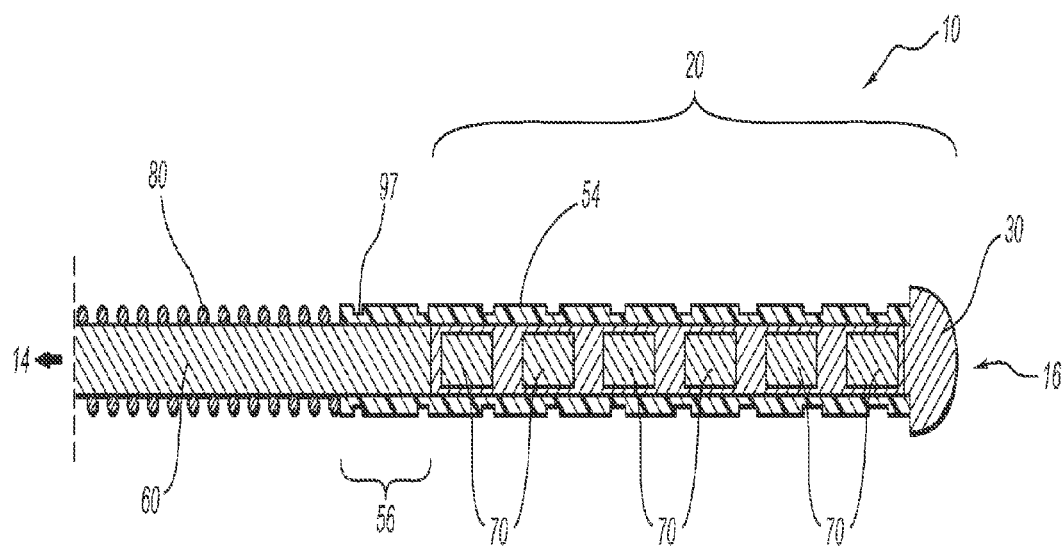
FIG. 6 is a partial cross-sectional side view of an exemplary stylet according to an additional embodiment.

FIG. 6 is a partial cross-sectional side view of an exemplary stylet 10 according to an additional embodiment. As seen in this exemplary embodiment, exemplary stylet 10 may comprise an elongated core element 60, a tubular member 54 circumferentially disposed about a distal region 56 of core element 60, and a plurality of magnetic elements 70 housed within tubular member 54 proximate distal region 20. As mentioned above, tubular member 54 may also comprise features that influence its flexibility or stiffness. For example, as shown in FIG. 6, one or more grooves 97 may be defined along the outer surface of tubular member 54 to provide a desired level of flexibility to tubular member 54. Grooves 97, which may be formed in any number of shapes and sizes, generally represent any form of groove, indentation, hole, aperture, or notch defined into or through one or more portions of tubular member 54. Examples of grooves 97 include, without limitation, circumferential grooves, longitudinally extending grooves, helical grooves, holes, or other suitable features. Grooves 97 may be defined along or through tubular member 54 by any number of processes known in the art; including, for example, laser machining, electrode discharge machining, etching, grinding, or sawing (e.g., with a diamond-coated wafer dicing saw). Similar to the exemplary embodiment illustrated in FIG. 5, and as shown in FIG. 6, tubular member 54 may be closed at the distal end 16 of stylet 10 by a weld element 30. As with closure element 62, weld element 30 generally represents any form or type of structure used to retain magnetic elements 70 within tubular member 54.

Figure 7:
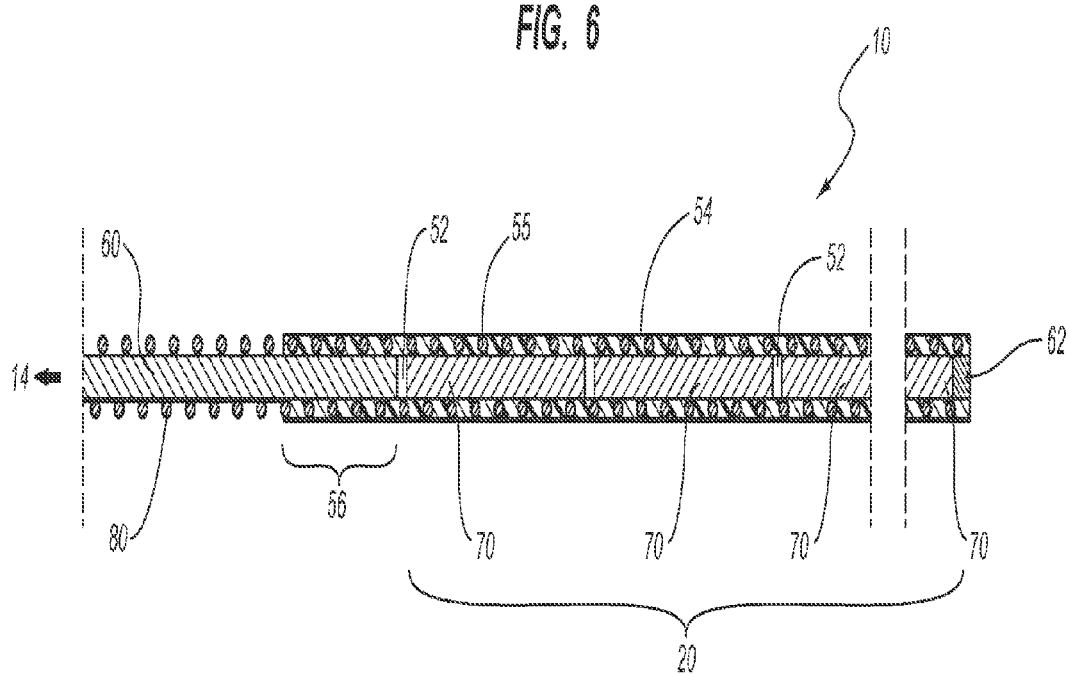
FIG. 7 is a partial cross-sectional side view of an exemplary stylet according to an additional embodiment.

FIG. 7 is a partial cross-sectional side view of an exemplary stylet 10 according to an additional embodiment. As seen in this figure, exemplary stylet 10 may comprise an elongated core element 60, a support element 80 circumferentially disposed about at least a portion of core element 60, a tubular member 54 comprising a reinforcing element 55 circumferentially disposed about a distal region 56 of core element 60, and a plurality of magnetic elements 70 housed within tubular member 54 proximate distal region 20. As detailed above, the stiffness or rigidity of exemplary stylet 10 may be modified or tailored as desired by adding or removing support element 80, tubular member 54, and/or reinforcing element 55. In the exemplary embodiment illustrated in FIG. 7, each of these elements may be used in combination to impart a greater amount of stiffness or rigidity to stylet 10.

Figure 8:
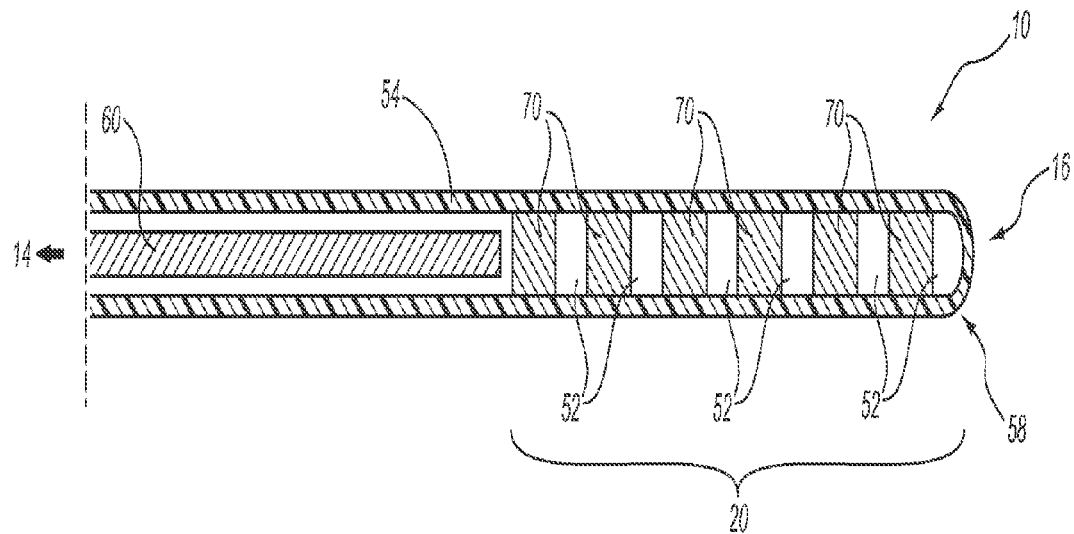
FIG. 8 is a partial cross-sectional side view of an exemplary stylet according to an additional embodiment.

FIG. 8 is a partial cross-sectional side view of an exemplary stylet 10 according to an additional embodiment. As seen in this figure, exemplary stylet 10 may comprise an elongated core element 60, a tubular member 54 circumferentially disposed about core element 60, and a plurality of magnetic elements 70 housed within tubular member 54 proximate distal region 20. In addition, as opposed to comprising a weld element 30 or a closure element 62, tubular member 54 may comprise a closed end 58. Because tubular member 54 may comprise a closed end 58, as opposed to comprising a weld element 30 or a closure element 62, additional processes for forming either weld element 30 or closure element 62 may be avoided.

Figure 9:
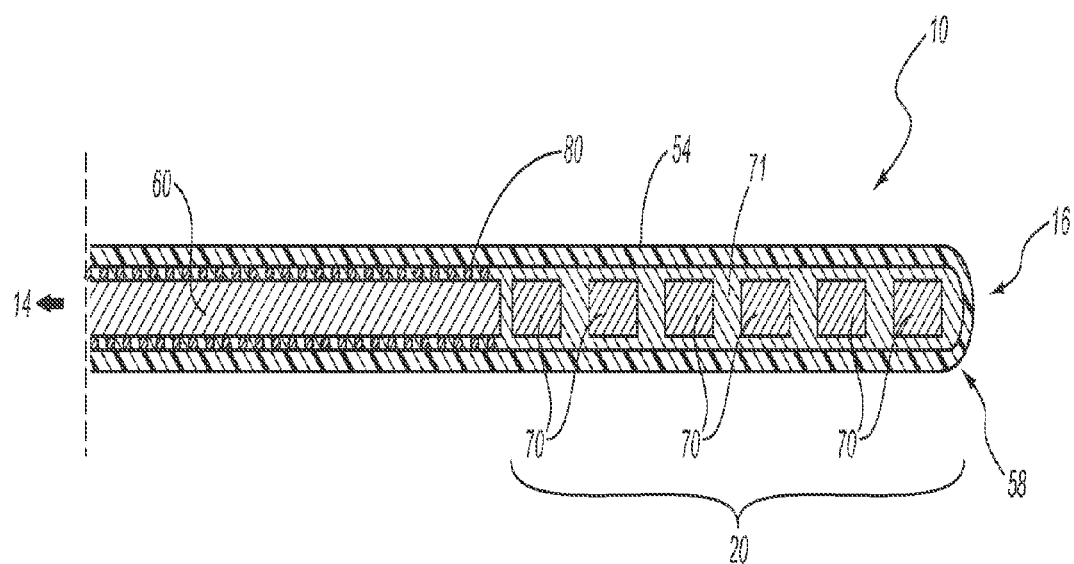
FIG. 9 is a partial cross-sectional side view of an exemplary stylet according to an additional embodiment.

FIG. 9 is a partial cross-sectional side view of an exemplary stylet 10 according to an additional embodiment. As seen in this exemplary embodiment, exemplary stylet 10 may comprise an elongated core element 60, a support element 80 circumferentially disposed about at least a portion of core element 60, a tubular member 54 circumferentially disposed about core element 60, and a plurality of magnetic elements 70 housed within tubular member 54 proximate distal region 20. As illustrated in FIG. 9, tubular member 54 may be circumferentially disposed about substantially the entire length of both support element 80 and core element 60 (i.e., from the distal end 16 of stylet 10 to proximate end 14). In addition, as with the exemplary embodiment illustrated in FIG. 8, tubular member 54 may comprise a closed end 58. As with previous embodiments, a filling material 71 may also be disposed between magnetic elements 70 within tubular member 54. As detailed above, filling material 71 may comprise any number of suitable pliant materials to maintain or facilitate separation of adjacent magnetic elements 70, thereby providing a desired level of flexibility to distal region 20 of stylet 10. In additional embodiments, in place of filling material 71, spacing elements (such as spacing elements 92, described in connection with FIG. 23 below) may be positioned between longitudinally adjacent magnetic elements 70.

Figure 10:
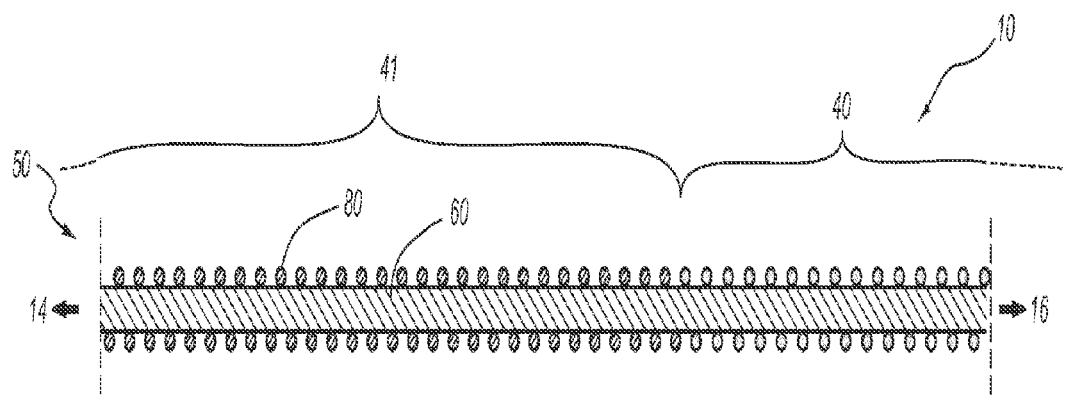
FIG. 10 is a partial cross-sectional side view of an exemplary stylet according to an additional embodiment.

FIG. 10 is a partial cross-sectional side view of an exemplary stylet 10 according to an additional embodiment. As seen in this exemplary embodiment, exemplary stylet 10 may comprise an elongated core element 60 and a support element 80 circumferentially disposed about substantially the entire length of core element 60. In at least one embodiment, at least a portion of support element 80, core element 60, or both, may comprise a magnetic material. For example, as shown in FIG. 10, support element 80 may comprise a magnetic material within a magnetic region 40, while comprising a non-magnetic material within a non-magnetic region 41. In certain embodiments, support element 80 may be manufactured by first forming support element 80 of a non-magnetized material and then magnetizing a select portion (e.g., magnetic region 40) of support element 80. In another embodiment, support element 80 may be formed to initially include a magnetic material within region 40. Magnetization of magnetic region 40 may be accomplished by utilizing any known material or process for magnetization as known in the art, without limitation.

Figure 11:
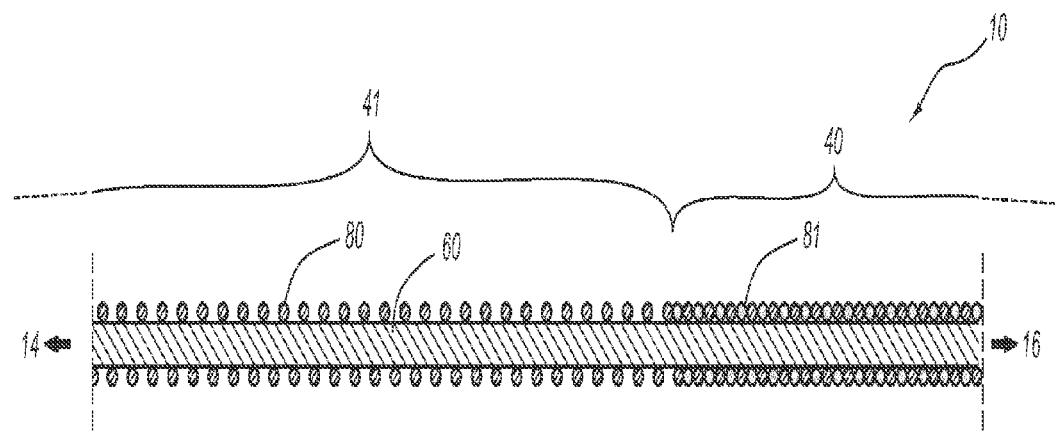
FIG. 11 is a partial cross-sectional side view of an exemplary stylet according to an additional embodiment.

FIG. 11 is a partial cross-sectional side view of an exemplary stylet 10 according to an additional embodiment. As seen in this exemplary embodiment, exemplary stylet 10 may comprise an elongated core element 60 and a support element 80 circumferentially disposed about substantially the entire length of core element 60. In at least one embodiment, stylet 10 may also comprise a magnetic coil 81 circumferentially disposed about a select portion of core element 60. For example, as illustrated in FIG. 11, magnetic coil 81 may be circumferentially disposed about a distal region of core element 60 to form a magnetic region 40. In certain embodiments, magnetic coil 81 may be longitudinally disposed between portions (e.g., coils) of support element 80. Optionally, magnetic coil 81 may be circumferentially disposed about (i.e., radially surround) support element 80.

Figure 12:
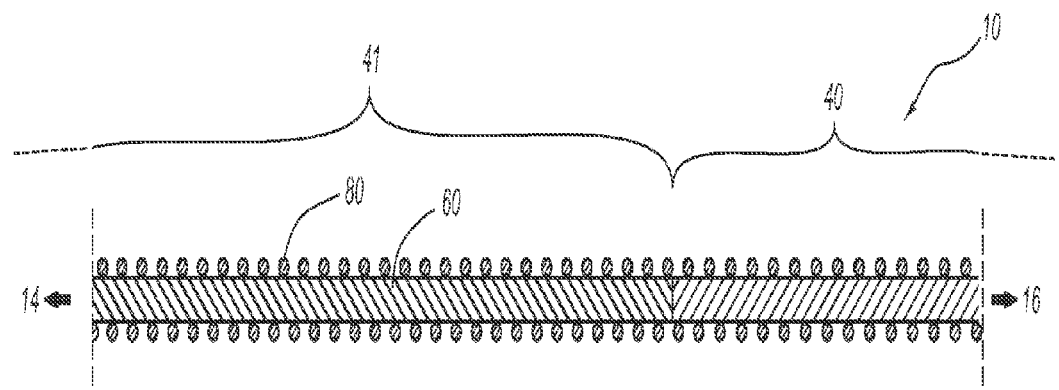
FIG. 12 is a partial cross-sectional side view of an exemplary stylet according to an additional embodiment.

FIG. 12 is a partial cross-sectional side view of an exemplary stylet 10 according to an additional embodiment. As seen in this exemplary embodiment, exemplary stylet 10 may comprise an elongated core element 60 and a support element 80 circumferentially disposed about substantially the entire length of core element 60. In at least one embodiment, at least a portion of core element 60 may comprise a magnetic material. For example, as shown in FIG. 12, core element 60 may comprise a non-magnetic portion within non-magnetic region 41 of stylet 10 and a magnetic portion within magnetic region 40 of stylet 10. In certain embodiments, core element 60 may be formed by initially including a magnetic material within core element 60 in magnetic region 40. Optionally, core element 60 may be formed by magnetizing a select portion (i.e., magnetic region 40) of core element 60. Advantageously, magnetizing a select portion of exemplary stylet 10 (e.g., support element 80, core element 60, or both), as opposed to housing a plurality of magnetic elements 70 within a tubular member, may provide a greater amount of flexibility to exemplary stylet 10.

Figure 13:
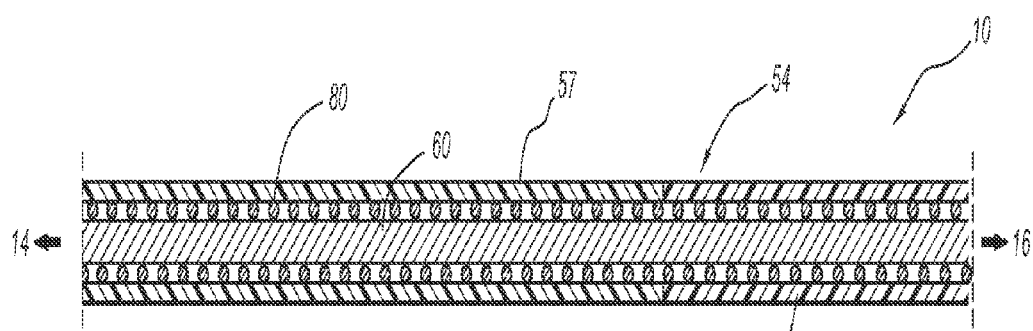
FIG. 13 is a partial cross-sectional side view of an exemplary stylet according to an additional embodiment.

FIG. 13 is a partial cross-sectional side view of an exemplary stylet 10 according to an additional embodiment. As seen in this figure, exemplary stylet 10 may comprise an elongated core element 60, a support element 80 circumferentially disposed about at least a portion of core element 60, and a tubular member 54 circumferentially disposed about at least a portion of both support element 80 and core element 60. In at least one embodiment, at least a portion of tubular member 54 may be magnetic. For example, as illustrated in FIG. 13, tubular member 54 may comprise a non-magnetic portion 57 and a magnetic portion 59. As with core element 60, the magnetic portion 59 of tubular member 54 may be formed of any type or form of magnetic material.

Figure 14:
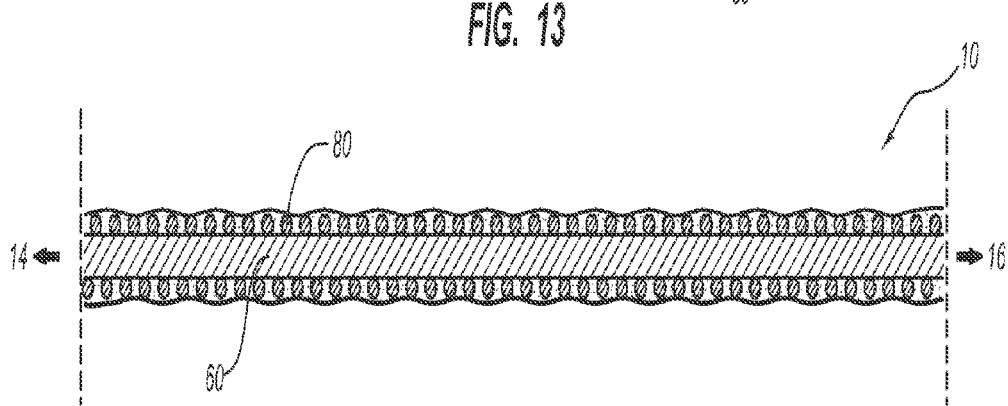
FIG. 14 is a partial cross-sectional side view of an exemplary stylet according to an additional embodiment.

FIG. 14 is a partial cross-sectional side view of an exemplary stylet 10 according to an additional embodiment. As seen in this figure, exemplary stylet 10 may comprise an elongated core element 60, a support element 80 circumferentially disposed about at least a portion of core element 60, and a tubular member 54 circumferentially disposed about at least a portion of both support element 80 and core element 60. In at least one embodiment, and as illustrated in FIG. 14, at least a portion of tubular member 54 may be at least partially melted to flow between adjacent portions (e.g., coils) of support element 80. As used herein, the term "melt" broadly refers to any process or method in which the glass transition temperature of tubular member 54 is exceeded. In certain embodiments, tubular member 54, when at least partially melted, may be formed or shaped by a mold or mandrel.

Figure 15:
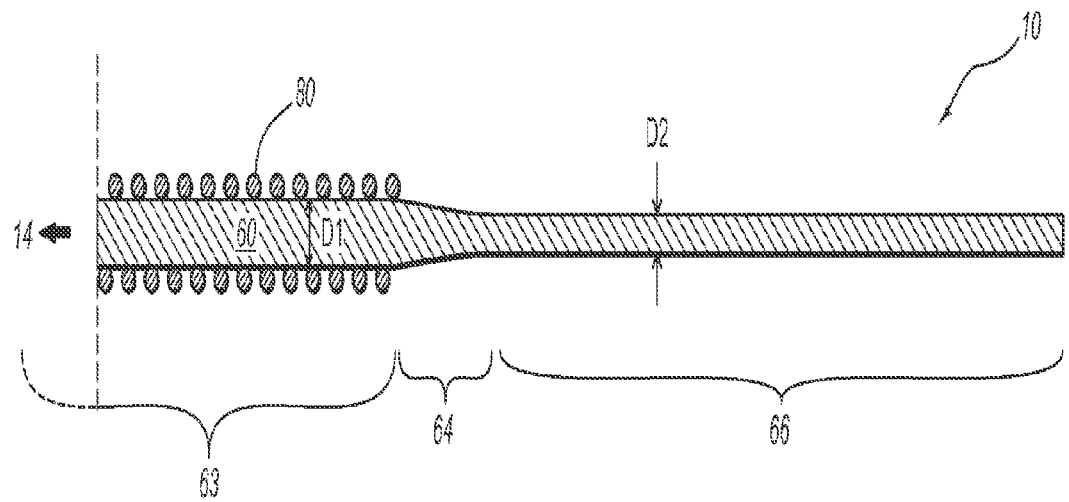
FIG. 15 is a partial cross-sectional side view of an exemplary stylet according to an additional embodiment.

FIG. 15 is a partial cross-sectional side view of an exemplary stylet 10 according to an additional embodiment. As seen in this figure, exemplary stylet 10 may comprise an elongated core element 60 and a support element 80 circumferentially disposed about at least a portion of core element 60. In at least one embodiment, core element 60 may comprise a first region 63, a second region 66, and a transition region 64 extending between first region 63 and second region 66. As seen in FIG. 15, second region 66 may have a second diameter D2 that is smaller than a first diameter D1 of first region 63. In certain embodiments, transition region 64, second region 66, or both may be formed by centerless grinding or any other processes known in the art. In another embodiment, first region 63 and second region 66 may be separate elements coupled or connected to one another. In addition, regions 63, 64, and 66 may each represent separate elements that may be coupled or connected to one another. Advantageously, the reduced diameter of second region 66, which may be provided proximate a distal region 20 of stylet 10, may exhibit increased flexibility to enable stylet 10 to traverse an arcuate subcutaneous path within a patient.

Figure 16:
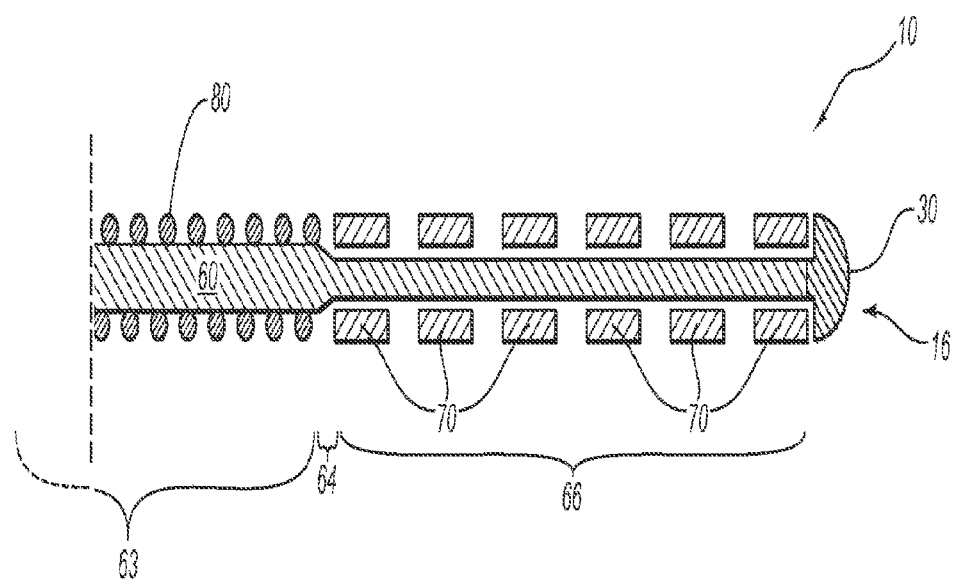
FIG. 16 is a partial cross-sectional side view of an exemplary stylet according to an additional embodiment.

FIG. 16 is a partial cross-sectional side view of an exemplary stylet 10 according to an additional embodiment. As seen in this figure, exemplary stylet 10 may comprise an elongated core element 60 and a support element 80 circumferentially disposed about at least a portion of core element 60. As with the exemplary embodiment illustrated in FIG. 15, core element 60 may comprise a first region 63, a second region 66 having a diameter that is less than the diameter of first region 63, and a transition region 64 extending between first region 63 and second region 66. In addition, exemplary stylet 10 may comprise one or more magnetic elements 70 circumferentially disposed about second region 66. In at least one embodiment, magnetic elements 70 may be generally cylindrical and/or toroidal in shape. Additionally, a weld element 30 may be provided at the distal end 16 of stylet 10 to position magnetic elements 70 around second region 66 of core element 60. In additional embodiments, magnetic elements 70 may be coupled to second region 66 by, for example, adhesives, threads, pins, or other suitable attachment means.

Figure 17:
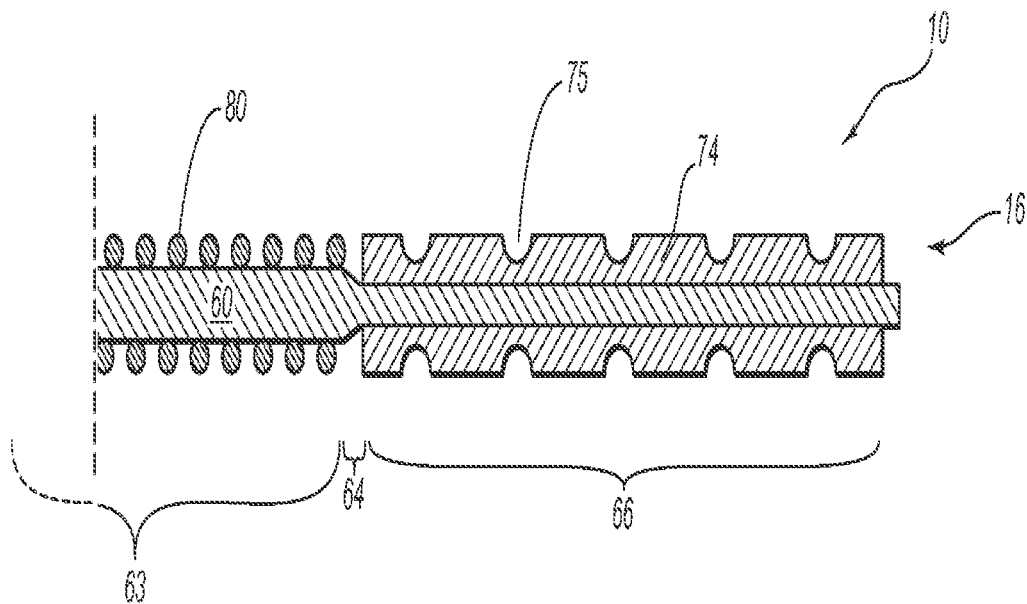
FIG. 17 is a partial cross-sectional side view of an exemplary stylet according to an additional embodiment.

FIG. 17 is a partial cross-sectional side view of an exemplary stylet 10 according to an additional embodiment. As seen in this figure, exemplary stylet 10 may comprise an elongated core element 60 and a support element 80 circumferentially disposed about at least a portion of core element 60. As with the exemplary embodiments illustrated in FIGS. 15 and 16, core element 60 may comprise a first region 63, a second region 66 having a diameter that is less than the diameter of first region 63, and a transition region 64 extending between first region 63 and second region 66. In at least one embodiment, a magnetic material may be press-fit or sintered to core element 60 about second region 66. For example, as illustrated in FIG. 17, a magnetic slug 74 may be press-fit or sintered to core element 60 in second region 66. In certain embodiments, one or more grooves 75 may be defined along the outer surface of magnetic slug 74 to provide a desired level of flexibility to magnetic slug 74. Similar to grooves 97, grooves 75 may be formed in any number of shapes and sizes. Examples of grooves 75 include, without limitation, circumferential grooves, longitudinally extending grooves, helical grooves, holes, or other suitable features.

Figure 18:
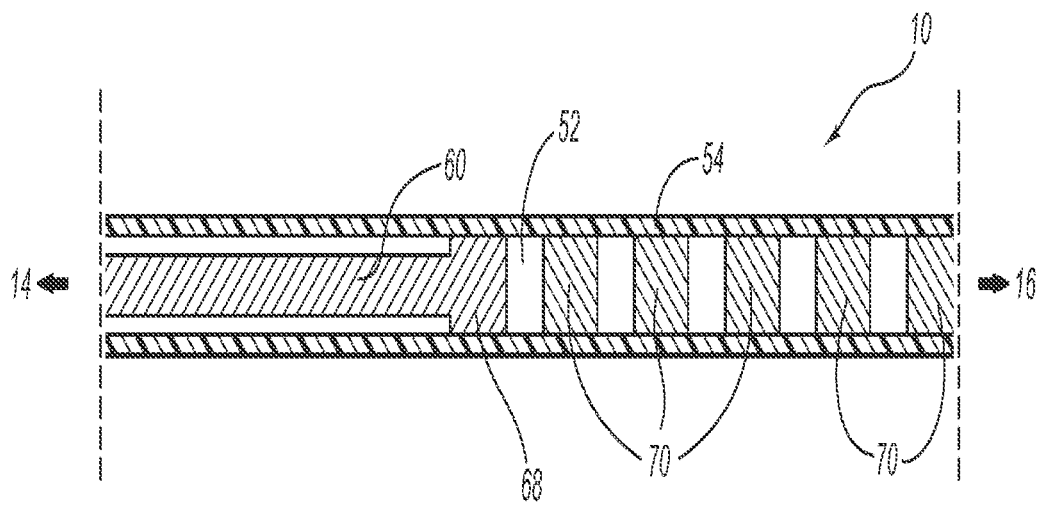
FIG. 18 is a partial cross-sectional side view of an exemplary stylet according to an additional embodiment.
Figure 19:
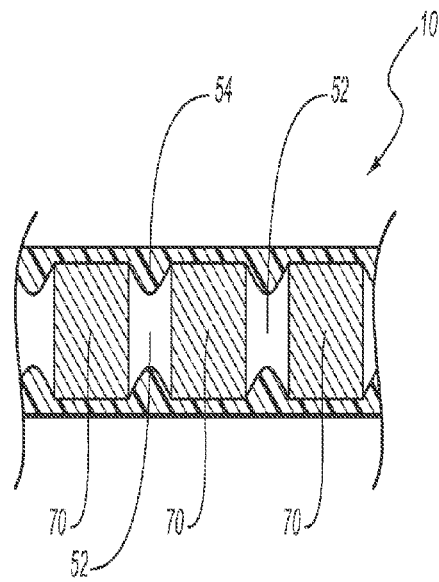
FIG. 19 is a partial cross-sectional side view of an exemplary stylet according to an additional embodiment.

FIGS. 18 and 19 are partial cross-sectional side views of an exemplary stylet 10 according to an additional embodiment. As seen in FIG. 18, exemplary stylet 10 may comprise an elongated core element 60, a tubular member 54 circumferentially disposed about at least a portion of core element 60, and a plurality of magnetic elements 70 housed within tubular member 54. In at least one embodiment, at least one magnetic element 70 may be coupled to core element 60 by deforming, pressing, sintering, melting, or otherwise attaching at least a portion of tubular member 54 to both core element 60 and magnetic element 70. In addition, as illustrated in FIG. 19, tubular member 54 may be positioned at least partially between adjacent magnetic elements 70 to maintain the longitudinal separation (i.e., gaps 52) between adjacent magnetic elements 70.

Figure 20:
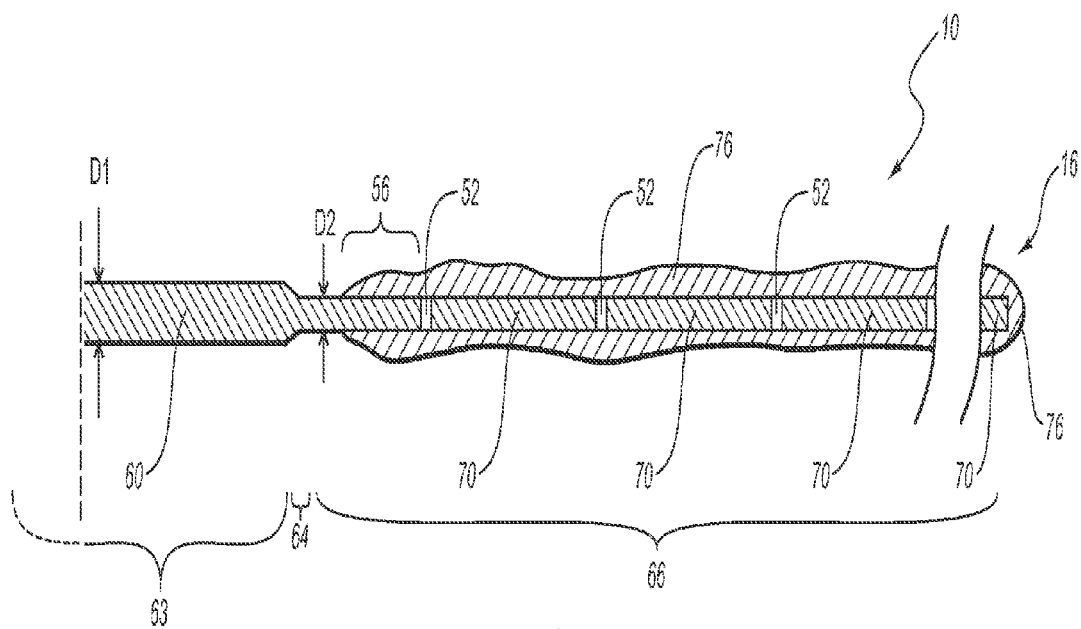
FIG. 20 is a partial cross-sectional side view of an exemplary stylet according to an additional embodiment.

FIG. 20 is a partial cross-sectional side view of an exemplary stylet 10 according to an additional embodiment. As seen in this figure, exemplary stylet 10 may comprise an elongated core element 60 comprising a first region 63, a second region 66 having a diameter that is less than the diameter of first region 63, and a transition region 64 extending between first region 63 and second region 66. In at least one embodiment, a coating 76 may be circumferentially disposed about at least a portion of core element 60 (e.g., distal region 56 of core element 60). Coating 76 may also be circumferentially disposed about one or more magnetic elements 70 to effectively couple magnetic elements 70 to core element 60. Coating 76, which generally represents any type or form of coating material, may be formed of any number or combination of materials; including, for example, polymers (such as polyimide, silicone, or so-called heat shrink tubing), metal, or other suitable materials. In general, coating 76 may be disposed about core element 60 and/or magnetic elements 70 by spraying, molding, dipping, or otherwise affixing coating 76 to core element 60 and/or magnetic elements 70. In certain embodiments, coating 76 may comprise a pliant material to impart a desired level of flexibility or rigidity to a distal region of stylet 10.

Figure 21:
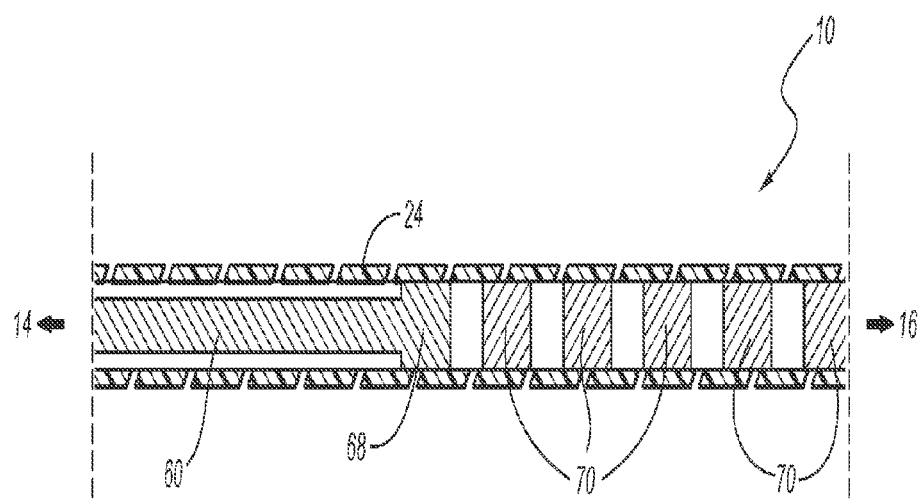
FIG. 21 is a partial cross-sectional side view of an exemplary stylet according to an additional embodiment.

FIG. 21 is a partial cross-sectional side view of an exemplary stylet 10 according to an additional embodiment. As seen in this exemplary embodiment, exemplary stylet 10 may comprise an elongated core element 60, a helical member 24 circumferentially disposed about at least a portion of core element 60, and a plurality of magnetic elements 70 housed within helical member 24. Generally speaking, helical member 24 represents any type or form of structure capable of helically surrounding at least a portion of core element 60 and/or magnetic elements 70. In at least one embodiment, helical member 24 may be affixed to core element 60, magnetic elements 70, or both. In certain embodiments, the helical configuration and material comprising helical member 24 may provide a desired level of flexibility to stylet 10. In addition, as illustrated in FIG. 21, core element 60 may also comprise a so-called mandrel having an enlarged distal end 68.

Figure 22:
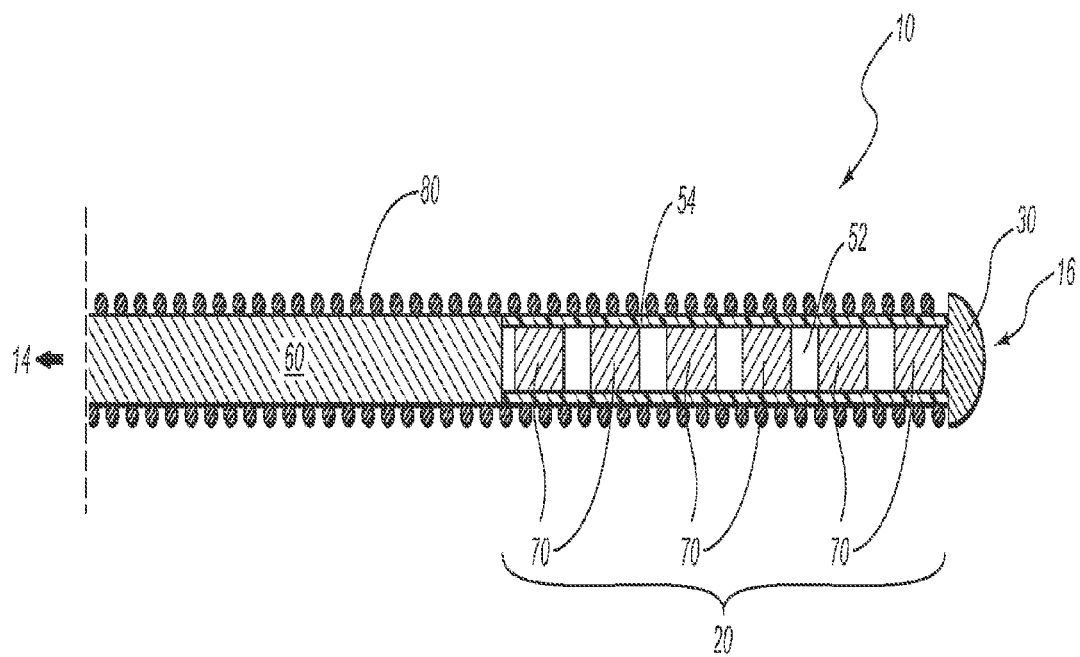
FIG. 22 is a partial cross-sectional side view of an exemplary stylet according to an additional embodiment.

FIG. 22 is a partial cross-sectional side view of an exemplary stylet 10 according to an additional embodiment. As seen in this figure, exemplary stylet 10 may comprise an elongated core element 60, a tubular member 54 positioned proximate a distal region 20 of stylet 10, and a plurality of magnetic elements 70 housed within tubular member 54. In at least one embodiment, a support element 80 may be circumferentially disposed about substantially the entire lengths of both core element 60 and tubular member 54 to effectively couple tubular member 54 (and magnetic elements 70 housed therein) to core element 60. A weld element 30 may also be provided proximate the distal end 16 of stylet 10 to effectively retain magnetic elements 70 within tubular member 54. In certain embodiments, support element 80 may be welded or otherwise affixed to weld element 30.

Figure 23:
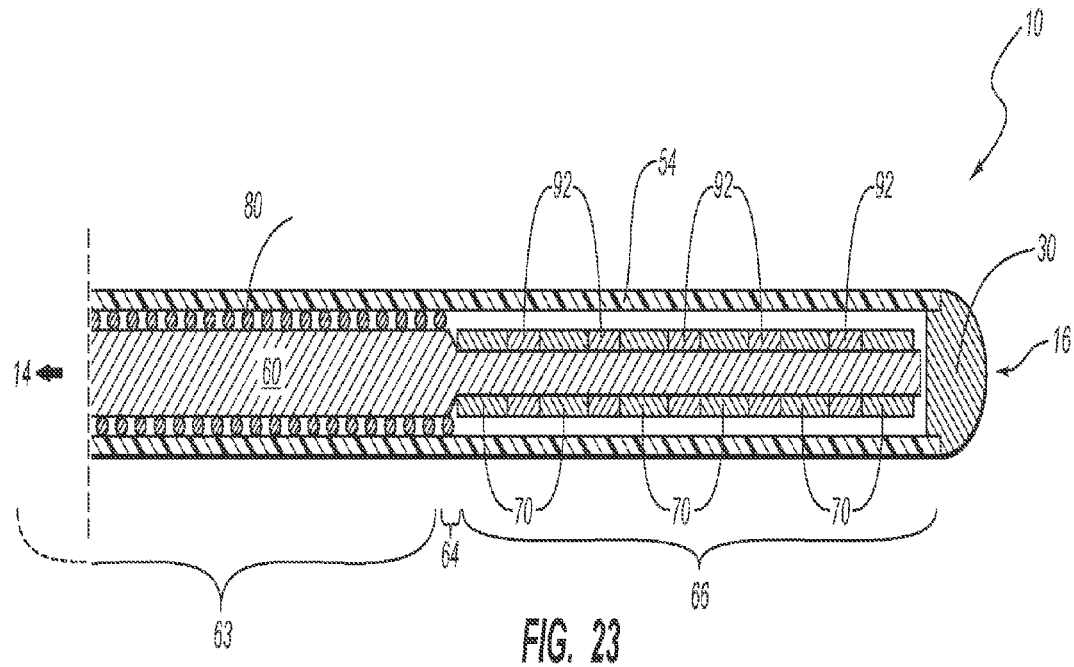
FIG. 23 is a partial cross-sectional side view of an exemplary stylet according to an additional embodiment.

FIG. 23 is a partial cross-sectional side view of an exemplary stylet 10 according to an additional embodiment. As seen in this figure, exemplary stylet 10 may comprise an elongated core element 60, a support member 80 circumferentially disposed about at least a portion of core element 60, a tubular member 54 circumferentially disposed about substantially the entire lengths of core element 60 and support member 80, and a plurality of magnetic elements 70 housed within tubular member 54 proximate a distal region of stylet 10. As with the exemplary embodiments illustrated in FIGS. 15-17, core element 60 may comprise a first region 63, a second region 66 having a diameter that is less than the diameter of first region 63, and a transition region 64 extending between first region 63 and second region 66. As with previous embodiments, magnetic elements 70 may be positioned about second region 66 of core element 60. In addition, in at least one embodiment, one or more spacing elements 92 may be positioned longitudinally between adjacent magnetic elements 70. Spacing elements 92, which may be formed of any number or combination of materials, generally represent any type or form of structure capable of separating longitudinally adjacent magnetic elements 70. In certain embodiments, a weld element 30 may be provided proximate distal end 16 to effectively retain magnetic elements 70 and spacing elements 92 within tubular member 54 and around second region 66 of core element 60.

Figure 24:
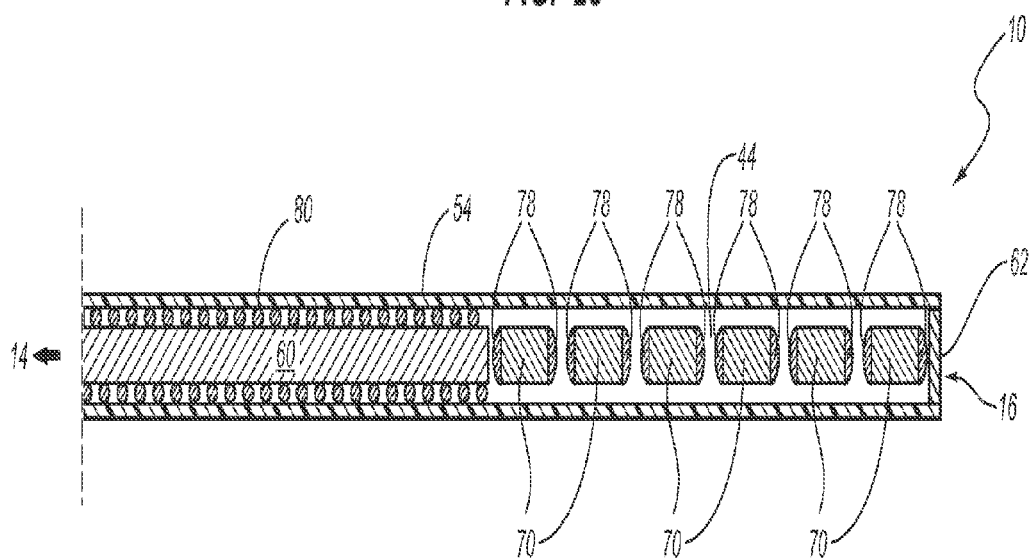
FIG. 24 is a partial cross-sectional side view of an exemplary stylet according to an additional embodiment.

FIG. 24 is a partial cross-sectional side view of an exemplary stylet 10 according to an additional embodiment. As seen in this figure, exemplary stylet 10 may comprise an elongated core element 60, a support member 80 circumferentially disposed about at least a portion of core element 60, a tubular member 54 circumferentially disposed about substantially the entire lengths of core element 60 and support member 80, and a plurality of magnetic elements 70 housed within tubular member 54 proximate a distal region of stylet 10. As with previous embodiments, a capture element 62 may be provided proximate distal end 16 to effectively retain magnetic elements 70 within tubular member 54. In at least one embodiment, a protective coating 78 may be applied the proximal and distal surfaces of each magnetic element 70. Protective coating 78, which may be formed of any number or combination of materials, generally represents any type of material capable of preventing direct contact between adjacent magnetic elements 70. In certain embodiments, protective coating 78 may be applied to magnetic elements 70 so as to form an arcuate shape on the proximal and distal ends of magnetic elements 70 to facilitate the bending of a distal region of stylet 10. As with previous embodiments, and as discussed in greater detail above, interstitial space 44 may be filled with a filler material, such as silicone, rubber, fluid, or other suitable material.

Figure 25:
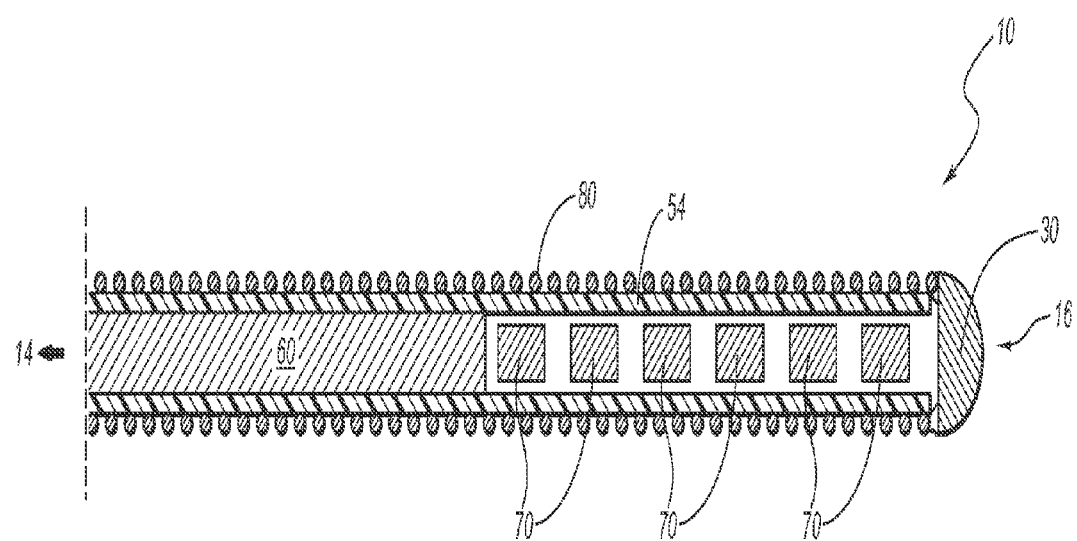
FIG. 25 is a partial cross-sectional side view of an exemplary stylet according to an additional embodiment.

FIG. 25 is a partial cross-sectional side view of an exemplary stylet 10 according to an additional embodiment. As seen in this figure, exemplary stylet 10 may comprise an elongated core element 60, a tubular member 54 circumferentially disposed about core element 60 and extending from proximate end 14 to distal end 16 of stylet 10, a plurality of magnetic elements 70 housed within tubular member 54 proximate a distal region of stylet 10, and a support member 80 circumferentially disposed about substantially the entire lengths of both tubular member 54 and core element 60. As with previous embodiments, a weld element 30 may be provided proximate distal end 16 of stylet 10 to effectively retain magnetic elements 70 within tubular member 54.

Figure 26:
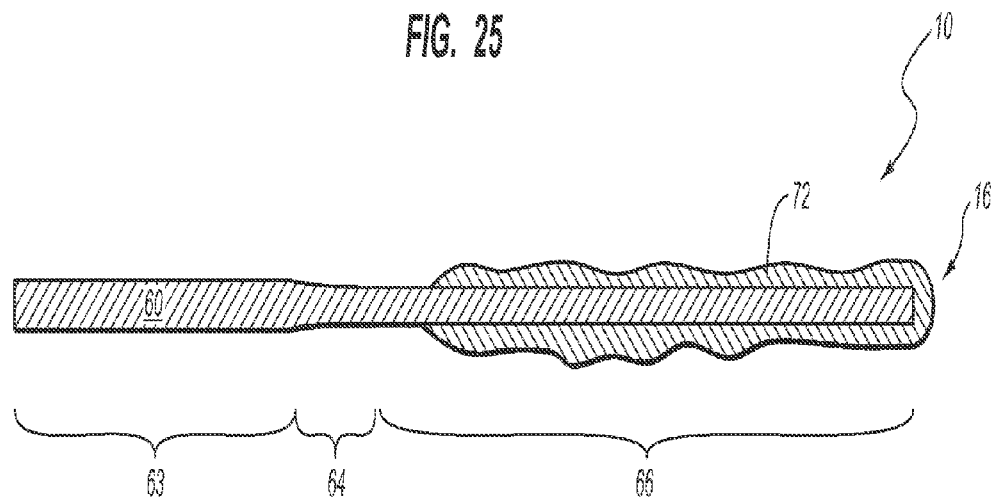
FIG. 26 is a partial cross-sectional side view of an exemplary stylet according to an additional embodiment.

FIG. 26 is a partial cross-sectional side view of an exemplary stylet 10 according to an additional embodiment. As seen in this figure, exemplary stylet 10 may comprise an elongated core element 60 having a first region 63, a second region 66 having a diameter that is less than the diameter of first region 63, and a transition region 64 extending between first region 63 and second region 66. In at least one embodiment, a magnetic coating 72 may be disposed about at least a portion of core element 60. For example, as illustrated in FIG. 26, magnetic coating 72 may be disposed over second region 66 of core element 60. In additional embodiments, magnetic coating 72 may extend over any portion of core element 60, including its entire length, without limitation.

Figure 27:
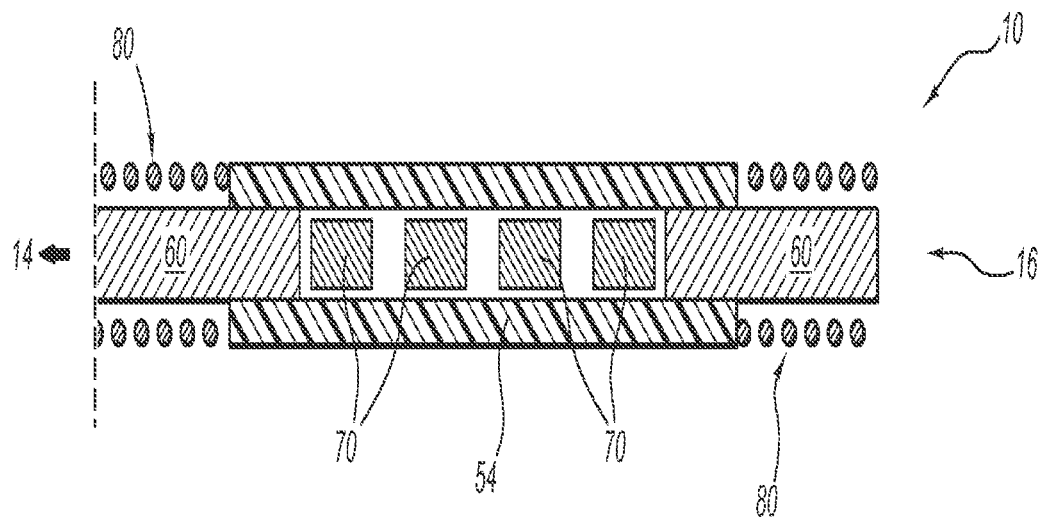
FIG. 27 is a partial cross-sectional side view of an exemplary stylet according to an additional embodiment.

FIG. 27 is a partial cross-sectional side view of an exemplary stylet 10 according to an additional embodiment. As seen in this figure, exemplary stylet 10 may comprise first and second elongated core element portions 60 and one or more magnetic elements 70 and disposed between these core element portions 60. In at least one embodiment, a tubular member 54 may be circumferentially disposed about magnetic elements 70 and at least a portion of each core element portion 60 to effectively retain magnetic elements 70 within stylet 10. In certain embodiments, a support member 80 may also be circumferentially disposed about at least a portion of each core element portion 60.

Figure 28:
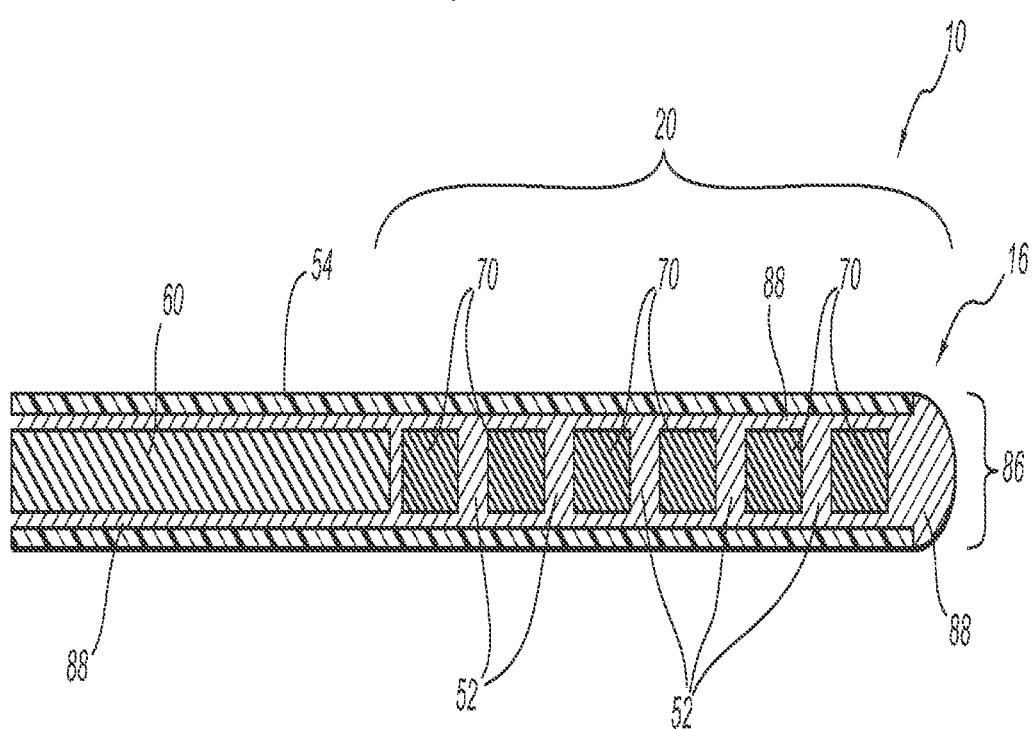
FIG. 28 is a partial cross-sectional side view of an exemplary stylet according to an additional embodiment.

FIG. 28 is a partial cross-sectional side view of an exemplary stylet 10 according to an additional embodiment. As seen in this figure, exemplary stylet 10 may comprise an elongated core element 60, a tubular member 54 circumferentially disposed about core element 60 and extending substantially the entire length of stylet 10 (i.e., from proximate end 14 to distal end 16 of stylet 10), and a plurality of magnetic elements 70 housed within tubular member 54 proximate a distal region of stylet 10. In at least one embodiment, tubular member 54 may be adhered or otherwise affixed directly to at least a portion of core element 60 and magnetic elements 70 to effectively couple magnetic elements 70 to core element 60. In an additional embodiment, a matrix material 88 may be disposed between core element 60, tubular member 54, and/or adjacent magnetic elements 70. Matrix material 88 generally represents any type or form of material, such as a suspension or slurry, capable of being disposed between core element 60, tubular member 54, and/or adjacent magnetic elements 70. Matrix material 88 may be formed of any number or combination of materials; including, for example, cyanoacrylate, epoxy, polyurethane, urethane, photopolymers, heat-curable materials, silicone, rubber, or any other suitable material, without limitation. In at least one embodiment, matrix material 88 may act as a filler, stabilizer, adhesive, or the like. In addition, in certain embodiments, matrix material 88 may form a rounded end 86 proximate distal end 16 of stylet 10 to effectively retain magnetic elements 70 within tubular member 54.

Figure 29:
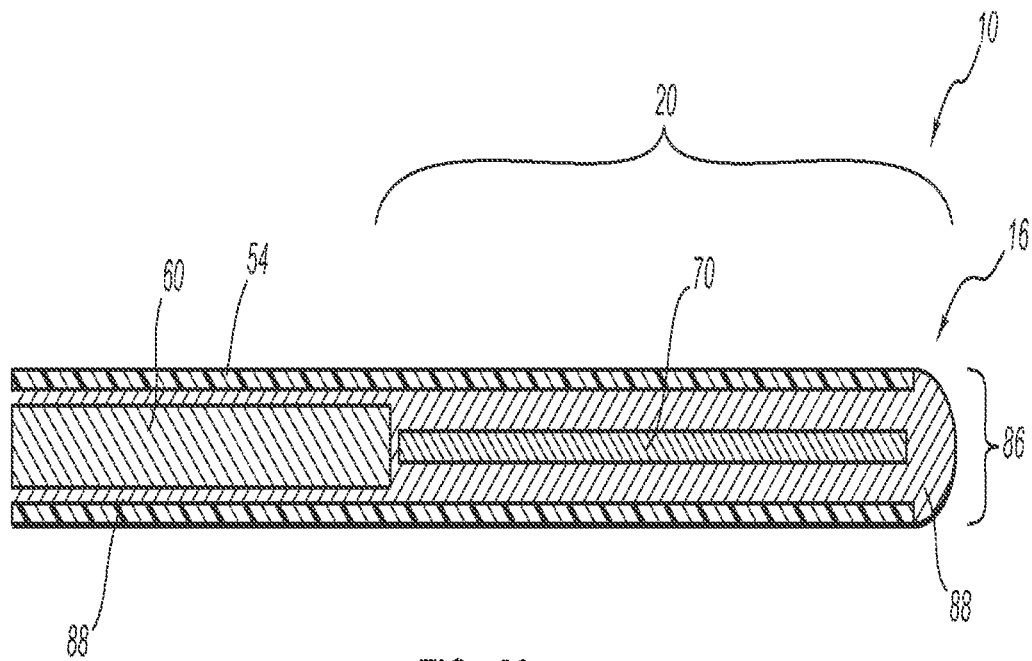
FIG. 29 is a partial cross-sectional side view of an exemplary stylet according to an additional embodiment.

FIG. 29 is a partial cross-sectional side view of an exemplary stylet 10 according to an additional embodiment. As seen in this figure, exemplary stylet 10 may comprise an elongated core element 60, a tubular member 54 circumferentially disposed about core element 60 and extending substantially the entire length of stylet 10 (i.e., from proximate end 14 to distal end 16 of stylet 10), and a single elongated magnetic element 70 housed within tubular member 54 proximate distal region 20 of stylet 10. As with tubular member 54, magnetic element 70 may be configured to exhibit a desired level of stiffness or flexibility. In certain embodiments, tubular member 54 may be adhered or otherwise affixed directly to at least a portion of core element 60 and/or magnetic element 70 to effectively couple magnetic element 70 to core element 60. In an additional embodiment, a matrix material 88 may be disposed between tubular member 54, core element 60, and/or magnetic element 70.

Figure 30:
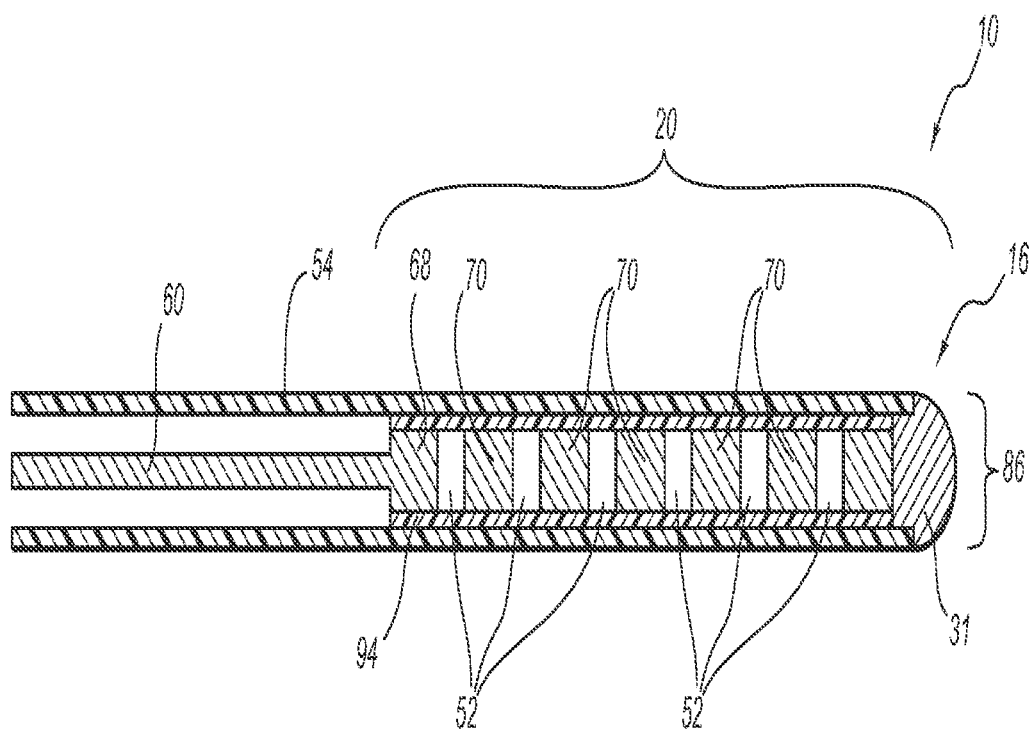
FIG. 30 is a partial cross-sectional side view of an exemplary stylet according to an additional embodiment.
Figure 31:
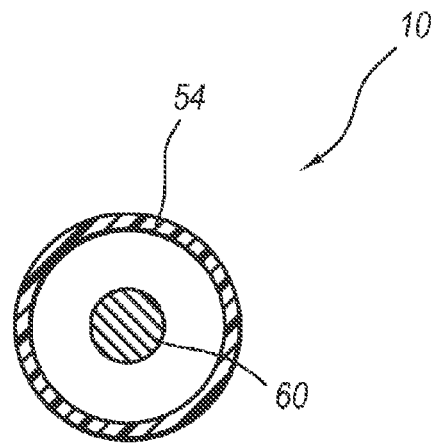
FIG. 31 is a partial cross-sectional end view of an exemplary stylet according to an additional embodiment.
Figure 32:
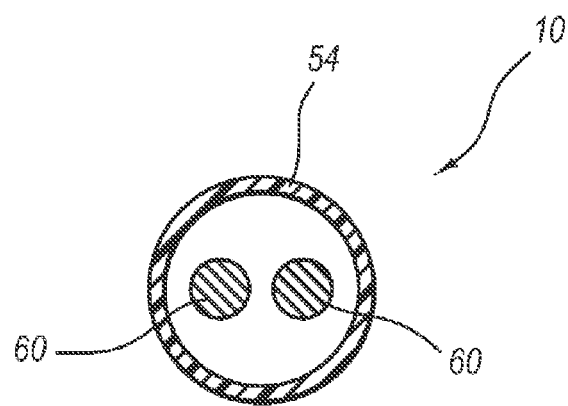
FIG. 32 is a partial cross-sectional end view of an exemplary stylet according to an additional embodiment.
Figure 33:
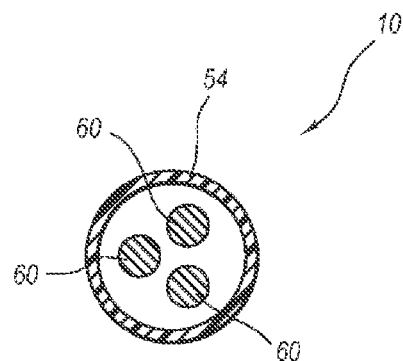
FIG. 33 is a partial cross-sectional end view of an exemplary stylet according to an additional embodiment.
Figure 34:
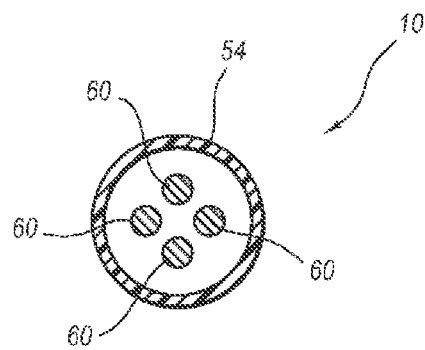
FIG. 34 is a partial cross-sectional end view of an exemplary stylet according to an additional embodiment.

FIG. 30 is a partial cross-sectional side view of an exemplary stylet 10 according to an additional embodiment. As seen in this figure, exemplary stylet 10 may comprise an elongated core element 60, a tubular member 54 circumferentially disposed about core element 60 and extending substantially the entire length of stylet 10 (i.e., from proximate end 14 to distal end 16 of stylet 10), and a plurality of magnetic elements 70 housed within tubular member 54 proximate distal region 20 of stylet 10. In at least one embodiment, core element 60 may comprise a so-called mandrel having an enlarged leading end 68. A closure element 31 forming a generally rounded end 86 may also be provided proximate the distal end 16 of stylet 10 to effectively retain magnetic elements 70 within tubular member 54. Closure element 31 may be affixed or otherwise attached to tubular member 54 in any number of ways; including, for example, by welding, bonding, adhering, or otherwise mechanically affixing closure element 31 to tubular member 54. Closure element 31 may also be formed of one or more adhesive materials, such as epoxy, and bonded to the tubular member 54.

In certain embodiments, a tubular sleeve 94 may be circumferentially disposed about and mechanically or chemically coupled to both the enlarged leading end 68 of core element 60 and at least one of magnetic elements 70 to effectively couple magnetic elements 70 to core element 60. Tubular sleeve 94 generally represents any type or form of material capable of being circumferentially disposed about core element 60 and/or at least one magnetic element 70. In certain embodiments, tubular sleeve may comprise a material that contracts or reduces in size (i.e., "shrinks") when heated to effectively couple one or more magnetic elements 70 to core element 60. In at least one embodiment, exemplary stylet 10 may be assembled by disposing tubular sleeve 94 about the enlarged leading end 68 of core element 60 and contracting (e.g., by applying heat to a select portion of tubular sleeve 94 using, for example, a heat gun) at least a portion of tubular sleeve 94 about enlarged leading end 68. In addition, magnetic elements 70 may be retained within tubular sleeve 94 by contracting at least a portion of tubular sleeve 94 (e.g., by applying heat to at least a portion of tubular sleeve 94) about magnetic elements 70. In additional embodiments, tubular sleeve 94 may be configured to contract about (i.e., circumferentially engage) at least a portion of closure element 31 without engaging magnetic elements 70.

FIGS. 31-34 are partial cross-sectional end views of exemplary stylets 10. As illustrated in these figures, stylet 10 may comprise one or more elongated core elements 60. For example, stylet 10 may comprise a single core element 60 (FIG. 31), two core elements 60 (FIG. 32), three core elements 60 (FIG. 33), four core elements 60 (FIG. 34), or more. In certain embodiments, each core element 60 in exemplary stylet 10 may be formed so as to be substantially identical to one another. In additional embodiments, each core element 60 in stylet 10 may be structurally unique. In addition, in any of the above-described exemplary embodiments, one or more than one core element 60 may comprise a magnetic portion. Advantageously, by employing a plurality of core elements 60 having unique magnetic configurations, a user may be able to precisely identify the location of distal region 20 of stylet 10 along select x, y, and z axes (i.e., pitch, yaw, and roll).

Figure 35:
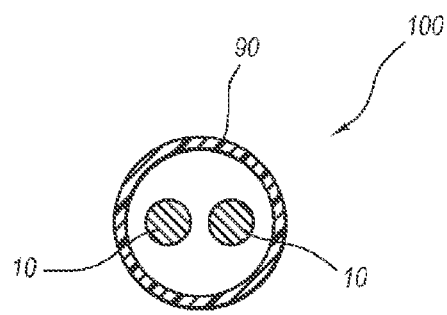
FIG. 35 is a partial cross-sectional end view of an exemplary catheter assembly according to at least one embodiment.

FIG. 35 is a partial cross-sectional end view of an exemplary catheter assembly 100 according to at least one embodiment. As illustrated in this figure, catheter assembly 100 may comprise a plurality of stylets 10 disposed within a catheter 90. Any number or configuration of stylets 10 may be disposed within catheter 90 of catheter assembly 100, without limitation. For example, catheter assembly 100 may comprise one, two, three, four, or more stylets 10 disposed within exemplary catheter 90. As with the exemplary embodiments illustrated in FIGS. 31-34, each stylet 10 disposed within catheter 90 may be substantially identical to one another, or structurally unique from each other. In addition, by employing a plurality of stylets 10 having unique magnetic element configurations, a user may be able to precisely identify the location of a distal region of catheter 90 along select x, y, and z axes (i.e., pitch, yaw, and roll).

Figure 36:
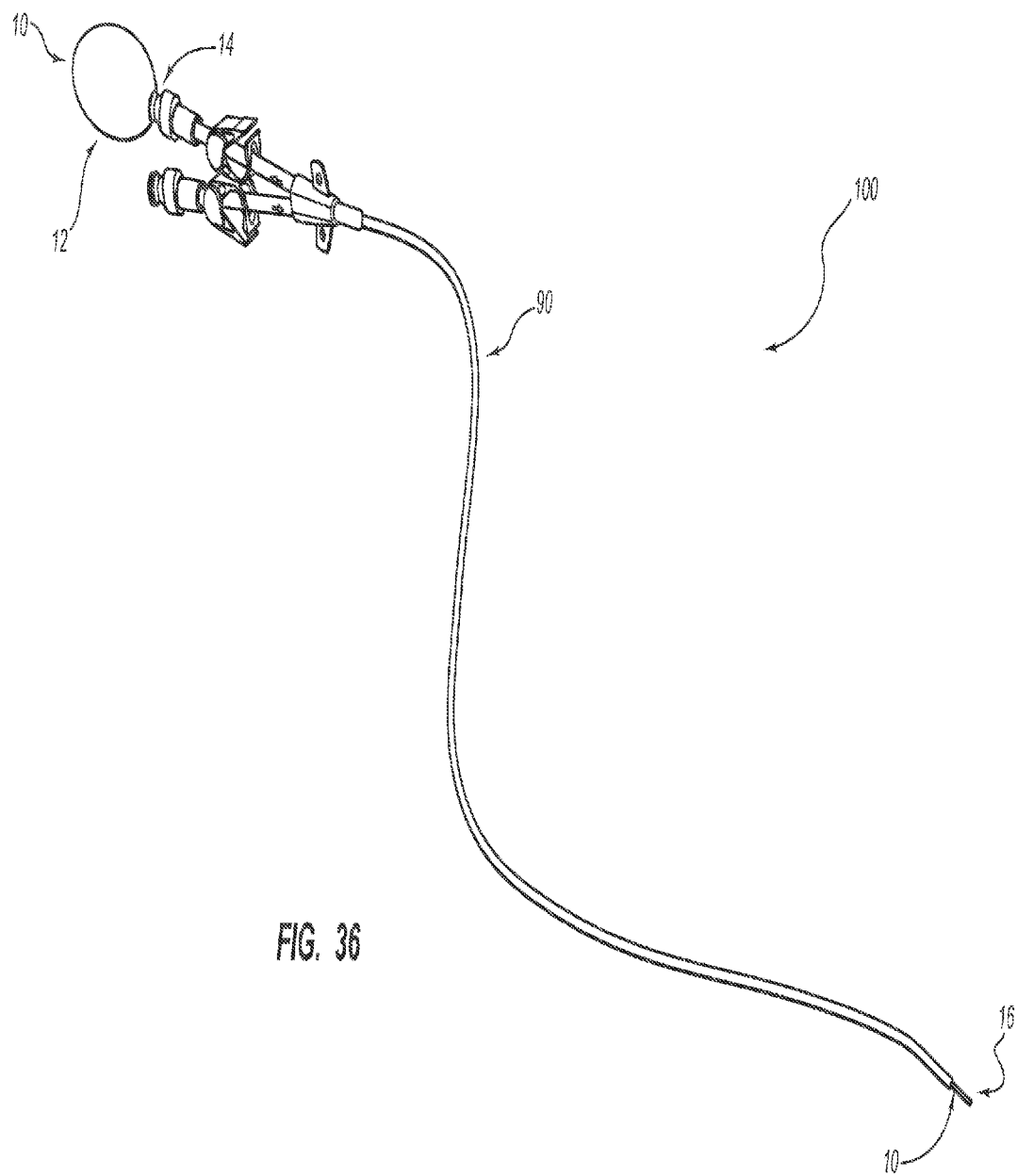
FIG. 36 is a perspective view of an exemplary catheter assembly according to at least one embodiment.

Although the above-described embodiments show particular configurations of exemplary stylets comprising magnetic materials, such embodiments are exemplary. Accordingly, many different embodiments are contemplated and encompassed by this disclosure. In addition, one or more of the exemplary stylet embodiments described and/or illustrated herein may be at least partially disposed within a lumen of a catheter, cannula, hollow needle, or other suitable device to provide (i.e., impart) increased stiffness or rigidity to the device. For example, as illustrated in FIG. 36, one or more stylets 10 may be positioned within a catheter 90 of a catheter assembly 100 to facilitate the navigation of the catheter 90 within a select portion of a patient. For example, at least one stylet 10 may be inserted into the lumen of a catheter 90, such as a peripherally inserted central catheter (PICC), to help guide catheter 90 into the superior vena cava (SVC) of a patient. Catheter assembly 100 may also be used in connection with other suitable applications, as desired.

The preceding description has been provided to enable others skilled in the art to best utilize various aspects of the exemplary embodiments described herein. This exemplary description is not intended to be exhaustive or to be limited to any precise form disclosed. Many modifications and variations are possible without departing from the spirit and scope of the instant disclosure. It is desired that the embodiments described herein be considered in all respects illustrative and not restrictive and that reference be made to the appended claims and their equivalents for determining the scope of the instant disclosure. In addition, for ease of use, the words "including" and "having," as used in the specification and claims, are interchangeable with and have the same meaning as the word "comprising."

What is claimed is:

1. An elongated medical device, comprising:
    a core element having a distal region including:
        a first region with a first diameter;
        a second region with a second diameter less than the first diameter, the second region distal of the first region and terminating at a core element distal end; and
        a transition region tapering from the first diameter to the second diameter, the second diameter of the second region extending from the transition region to the core element distal end;
    a support member circumferentially disposed about a length of the first region, the length of the first region having a constant diameter;
    a polymer member circumferentially disposed about an entire length of the core element and extending distal of the core element distal end;
    a closure element affixed to a distal end of the polymer member; and
    a permanent magnetic element disposed along the second region proximal to the core element distal end.

2. The elongated medical device according to claim 1, further comprising the support member circumferentially disposed about the first region, the polymer member disposed over the support member.

3. The elongated medical device according to claim 1, wherein the permanent magnetic element comprises a plurality of magnetic elements spaced apart along the second region.

4. The elongated medical device according to claim 3, further comprising a plurality of spacing elements, each of the plurality of spacing elements disposed between adjacent magnetic elements.

5. The elongated medical device according to claim 1, wherein the closure element comprises one or more adhesive materials bonded to the polymer member.

6. The elongated medical device according to claim 1, wherein the closure element comprises a weld member.

7. The elongated medical device according to claim 1, wherein the closure element includes a rounded distal end.

8. The elongated medical device according to claim 1, wherein the permanent magnetic element comprises a rare-earth magnetic element.

9. The elongated medical device according to claim 1, wherein the permanent magnetic element comprises an AlNiCo magnetic element.

10. The elongated medical device according to claim 1, wherein the permanent magnetic element comprises a PANiCNQ magnetic element.

11. The elongated medical device according to claim 1, wherein the permanent magnetic element comprises a ceramic magnetic element.

12. The elongated medical device according to claim 1, wherein the permanent magnetic element comprises a magnetic slug.

13. The elongated medical device according to claim 12, wherein the magnetic slug includes one or more grooves defined along an outer surface of the magnetic slug.

14. An elongated medical device, comprising:
    a core element having a distal region for insertion into a body of patient, the distal region including:
        a first region with a first diameter;
        a second region with a second diameter less than the first diameter, the second region distal of the first region and terminating at a core element distal end;
    a support member circumferentially disposed about a length of the first region, the length of the first region having a constant diameter;
    a polymer member circumferentially disposed about an entire length of the core element and extending distal of the core element distal end;
    a weld member affixed to a distal end of the polymer member; and
    a permanent magnetic element disposed along the second region proximate the core element distal end.

15. The elongated medical device according to claim 14, wherein the permanent magnetic element comprises a plurality of magnetic elements spaced apart along the second region.

16. The elongated medical device according to claim 15, further comprising a plurality of spacing elements, each of the plurality of spacing elements disposed between adjacent magnetic elements.

17. The elongated medical device according to claim 14, further comprising a transition region tapering from the first diameter to the second diameter, the second diameter of the second region extending from the transition region to the core element distal end.

18. The elongated medical device according to claim 1, wherein the second region has a straight unstressed configuration.

19. An elongated medical device, comprising:
- a core element having a distal region for insertion into a body of patient, the distal region including:
  - a first region with a constant first diameter;
  - a second region with a constant second diameter less than the first diameter, the second region distal of the first region and terminating at a core element distal end, the second region having a straight unstressed configuration;
- a polymer member circumferentially disposed about an entire length of the core element and extending distal of the core element distal end;
- a closure element affixed to a distal end of the polymer member; and
- a plurality of permanent magnetic elements disposed along the second region proximate the core element distal end.

* * * * *